United States Patent
Nordkild et al.

(10) Patent No.: US 11,413,328 B2
(45) Date of Patent: Aug. 16, 2022

(54) METHODS FOR TREATING INFLAMMATORY CONDITIONS OF THE LUNGS

(71) Applicant: Novozymes A/S, Copenhagen N (DK)

(72) Inventors: Peter Nordkild, Gentofte (DK); Søren Kjærulff, Holte (DK)

(73) Assignee: NOVOZYMES A/S, Bagsvaer (DK)

( * ) Notice: Subject to any disclaimer, the term of this patent is extended or adjusted under 35 U.S.C. 154(b) by 542 days.

(21) Appl. No.: 16/468,051

(22) PCT Filed: Dec. 13, 2017

(86) PCT No.: PCT/EP2017/082535
§ 371 (c)(1),
(2) Date: Jun. 10, 2019

(87) PCT Pub. No.: WO2018/108971
PCT Pub. Date: Jun. 21, 2018

(65) Prior Publication Data
US 2019/0336576 A1    Nov. 7, 2019

(30) Foreign Application Priority Data

Dec. 13, 2016    (DK) .......................... PA 2016 70991

(51) Int. Cl.
| | | |
|---|---|---|
| A61K 38/17 | (2006.01) | |
| A61P 11/06 | (2006.01) | |
| A61K 9/00 | (2006.01) | |
| A61K 38/38 | (2006.01) | |
| A61K 45/06 | (2006.01) | |

(52) U.S. Cl.
CPC .......... *A61K 38/1729* (2013.01); *A61K 9/007* (2013.01); *A61K 9/0053* (2013.01); *A61K 38/38* (2013.01); *A61K 45/06* (2013.01); *A61P 11/06* (2018.01)

(58) Field of Classification Search
None
See application file for complete search history.

(56) References Cited

U.S. PATENT DOCUMENTS

| | | | |
|---|---|---|---|
| 7,855,177 B1 | 12/2010 | Wahren et al. | |
| 9,279,010 B2* | 3/2016 | Kjaer ........................ | A61P 1/00 |
| 2004/0091498 A1 | 5/2004 | Zhang et al. | |
| 2004/0121343 A1* | 6/2004 | Buechler .............. | C12Q 1/6883 |
| | | | 435/6.14 |
| 2008/0051333 A1 | 2/2008 | Shi et al. | |
| 2012/0107336 A1* | 5/2012 | Moss ...................... | A61P 11/00 |
| | | | 424/185.1 |
| 2014/0341876 A1* | 11/2014 | Moss ...................... | A61P 11/00 |
| | | | 424/94.5 |
| 2015/0056253 A1 | 2/2015 | Bancel et al. | |

FOREIGN PATENT DOCUMENTS

| | | |
|---|---|---|
| EP | 2583684 A2 | 4/2013 |
| JP | 2005-514060 A | 5/2005 |
| JP | 2011-528332 A | 11/2011 |
| JP | 2015-3920 A | 1/2015 |
| WO | 03070176 A2 | 8/2003 |
| WO | 2008115390 A2 | 9/2008 |
| WO | 2010007165 A2 | 1/2010 |
| WO | 2010007166 A2 | 1/2010 |
| WO | 2011031713 A2 | 3/2011 |
| WO | 2012064601 A1 | 5/2012 |
| WO | 2013007596 A2 | 1/2013 |
| WO | 2013026794 A1 | 2/2013 |
| WO | 2014/089480 A1 | 6/2014 |
| WO | 2019/092201 A2 | 5/2019 |
| WO | 2019/092201 A3 | 6/2019 |

OTHER PUBLICATIONS

Liao, Z. et al. Enhanced Expression of Human Beta Defensin 2 in Peripheral Lungs of Patients with Chronic Obstructive Pulmonary Disease Peptides 38:350-356 2012. (Year: 2012).*
Pace, E. et al. Beta Defensin-2 is Reduced in Central but Not in Distal Airways of Smoker COPD Patients. PLoS One 7(3)33601 Mar. 1-8, 2012. (Year: 2012).*
Proud D. The Role of Defensins in Virus Induced Asthma. Current Allergy and Asthma Reports 6:81-85, 2006. (Year: 2006).*
Salzman, et al.; Paneth cell Defensins and the Regulation of the Microbiome, Gut Microbes, 2010, 1(6), 401-406. Year: 2010.
Harada, et al., Hepatology, vol. 40, pp. 925-932; Year 2004.
Bouloukaki, I. et al.; BMC Pulmonary Medicine, 11, 35: 1-8, 2011.
Charlson, E.S. et al.; American Journal of Respiratory and Critical Care Medicine, 184: 957-963, 2011.
Cosmi, L. et al.; Allergy, 66: 989-998, 2011.
Donia, M.S. and Fishback, M.A.; Science. 2015; 349(6246): 1254766. doi:10.1126/science.1254766.
Dorrestein, P.C. et al.; Immunity. 2014; 40(6): 824-832. doi:10.1016/j.immuni.2014.05.015.
Ege, M.J. et al.;The New England Journal of Medicine, 364, 8: 701-709, 2011.
Essilfie, A-T. et al.; Thorax, 70: 458-167, 2015.
Fletcher, C. and Peto, R.; British Medical Journal,1: 1645-1648, 1977.

(Continued)

*Primary Examiner* — Ralph J Gitomer
(74) *Attorney, Agent, or Firm* — Dinsmore & Shohl

(57) ABSTRACT

The present invention relates to methods for treatment or prevention of asthma, mild intermittent asthma, mild persistent asthma, moderate persistent asthma, severe persistent asthma, eosinophilic asthma, neutrophilic asthma, steroid refractory asthma, status asthmaticus, pneumonia, bronchiectasis, COPD, sarcoidosis, and lung cancer based on reducing airway hyper responsiveness, increasing pulmonary compliance, reducing lung inflammation, reducing inflammatory cell count in bronchoalveolar fluid and reducing cytokine production by administration of a mammalian α- and/or β-defensin.

14 Claims, 35 Drawing Sheets
Specification includes a Sequence Listing.

(56) References Cited

OTHER PUBLICATIONS

Hansbro, P.M. et al.; British Journal of Pharmacology; 163: 81-95, 2011.
Hansbro, P.M. et al.; Pharmacology & Therapeutics, 101: 193-210, 2004.
Hawkins, G.A. et al., "Analysis of the defensin gene family for DNA sequence variants", American Journal of Human Genetics, 71,4: 462, 2002.
Hilty, M. et al.; PLoS ONE, 5, 1, e8578, 2010.
Hogg, J.C. et al.; The New England Journal of Medicine, 350, 26: 2645-2653, 2004.
Jakobsson, H.E. et al.; Gut, 63: 559-566, 2014.
Marra, F. et al.; Pediatrics, 123, 3: 1003-1010, 2009.
Marsland, B.J. et al.; Ann Am Thorac Soc vol. 12, Supplement 2, pp. S150-S156, Nov. 2015.
Penders, J. et al.; Allergy, 62:1223-1236, 2007.
Salzman, N.H. et al.; Seminars in Immunology, 19: 70-83, 2007.
Schirmer, M. et al.; Cell. 2016; 167(4): 1125-1136.e8. doi:10.1016/j.cell.2016.10.020.
Shen, Z. et al.; International Journal of Molecular Sciences, 15: 13372-13387, 2014.
Lee, et al.; International Journal of Nanomedicine, 10 :5423-5434, 2015.
Trompette, A. et al.; Nature Medicine, 20, 2: 159-168, 2014.
Wehkamp, J. et al.; Digestive Diseases and Sciences, 47, 6: 1349-1355, 2002.
Wills-Karp, M. et al.; Nature Reviews, Immunology, 1: 69-75, 2001.
Wohlford-Lenane, C.L. et al.; Journal of Virology, 83, 21: 11385-11390, 2009.
Hanaoka, Y., et al., In Vitro and In Vivo Anticancer Activity of Human β-Defensin-3 and Its Mouse Homolog, Anticancer Research, 36: 5999-6004, 2016.
Carding, S. et al., Dysbiosis of the gut microbiota in disease, Microbial Ecology in Health & Disease, 26:26191, 9 pages, Feb. 2, 2015.
Allin et al., Gut microbiota in patients with type 2 diabetes mellitus, European Society of Endocrinology, vol. 172(4):167-177 (Feb. 2015) (Year: 2015).
Belizario et al., Human microbiomes and their roles in dysbiosis, common diseases, and novel therapeutic approaches, Front Microbial., vol. 6:1050 (Published online Oct. 6, 2015) doi: 10.3389/fmicb.2015.01050 (Year: 2015).
Hansen et al., The gut microbiome in cardio-metabolic health, Genome Med., vol. 7(1):33, 16 pages (online Mar. 31, 2015) (Year: 2015).
Larsen et al., Gut microbiota in human adults with type 2 diabetes differs from non-diabetic adults, PLoS One, vol. 5(2):e9085 (Feb. 5, 2010) (Year: 2010).
Moreno-Indias et al., Impact of the gut microbiota on the development of obesity and type 2 diabetes mellitus, Front. Microbial., vol. 5:190 (2014) (Year: 2014).
Portela-Cidade et al., Systematic Review of the Relation Between Intestinal Microbiota and Toll-Like Receptors in the Metabolic Syndrome: What Do We Know So Far?, GE PortJ. Gastroenterol., vol. 22(6):240-258 (Aug. 2015) (Year: 2015).
Tilg et al., Gut Microbiome, obesity, and metabolic dysfunction, J Clin Invest., vol. 121 (6): 2126-2132 (Jun. 1, 2011); (Year: 2011).
Fonseca, et al., Clinical Cornerstone, vol. 7(2/3):61-72; Year 2005.
Incani, et al., Journal of Diabetes Investigation, vol. 6(1):44-50; Year 2014.
Egli, D. et al., Prevention of Allergy and Allergic Asthma, Based on the WHO/WAO Meeting on the Prevention of Allergy and Allergic Asthma, Geneva, Jan. 8-9, 2002.
Niyonsaba, F. et al., Protective roles of the skin against infection: Implication of naturally occurring human antimicrobial agents β-defensins, cathelicidin LL-37 and lysozyme, Journal of Dermatological Science, 40: 157-168, 2005.
Nam, H. et al., Diesel exhaust particles increase IL-Iβ-induced human β-defensin expression via NF-KB-mediated pathway in human lung epithelial cells, Particle and Fibre Toxicology, 3: 1-9, May 25, 2006.
Beisswenger, C. et al., Allergic Airway Inflammation Inhibits Pulmonary Antibacterial Host Defense, Journal of Immunology, 177: 1833-1837, 2006.
Lehrer et al, Interaction of human defensins with *Eschericia coli*. Mechanism of bactericidal activity, J. Clin. Invest., 84(2): 553-561, 1989.
Sullivan, S. et al., An Exclusively Human Milk-Based Diet Is Associated with a Lower Rate of Necrotizing Enterocolitis than a Diet of Human Milk and Bovine Milk-Based Products, The Journal of Pediatrics, 156(4): 562-567, Apr. 2010.
Anand, S. et al., Diet, Microbiota and Gut-Lung Connection, Frontiers in Microbiology, 9(2147), pp. 1-12, Sep. 2018.
Wang, X. et al., Concentration characteristics of bovine[beta]-defensin 1 and 2 in fresh bovine milk and infant formula, International Journal of Dairy Technology, 68(2): 299-301, May 1, 2015; DOI: 10.1111/1471-0307.12214.
Caplan, M. et al., Role of Asphyxia and Feeding in a Neonatal Rat Model of Necrotizing Enterocolitis, Pediatric Pathology, 14(6): 1017-1028, Jan. 9, 1994; DOI: 0.3109/15513819409037698.
Schibli, D. et al., The solution structures of the human beta-defensins lead to a better understanding of the potent bactericidal activity of HBD3 against *Staphylococcus aureus*, J Biol Chem., 77(10): 8279-89, Mar. 8, 2002, doi: 10.1074/jbc.M108830200. Epub Dec. 11, 2001. PMID: 11741980.
Jensen, M. et al., Similar efficacy of human banked milk and bovine colostrum to decrease incidence of necrotizing enterocolitis in preterm piglets, Am J Physiol Regul Integr Comp Physiol., 305(1), Jul. 1, 2013, :R4-R12. doi: 10.1152/ajpregu.00094.2013. Epub May 8, 2013. PMID: 23657639.

\* cited by examiner

| Group # | N | Sensitization s.c. (day 0) | Challenge i.n./mouse Day 14 | Treatment Day 14 Dosing regimen and route to be agreed | Measurements and sampling 48hrs following challenge (day 16) |
|---|---|---|---|---|---|
| 1 | 14 | 100 μL of CFA in saline | 50 μL saline | - | • Blood for plasma (N=14) • Lungs for histopathology (N=8) • Lungs frozen for cytokine determination (N=6) |
| 2 | 14 | 100 μg HDM/0.2 mL saline+CFA/ mouse | 25μg HDM/50μL saline | Vehicle | |
| 3 | 14 | | | hbD2 p.o. 1.2 mg/kg/day (0.4 mg/kg TID) | |
| 4 | 14 | | | hbD2 i.n. 1.2 mg/kg/day (0.4 mg/kg TID) | |

Fig. 2

```
HBD1    ------DHYNCVSSGGQCLYSACPIFTKIQGTCYRGKAKCCK---
HBD2    ---GIGDPVTCLKSGAICHPVFCPRRYKQIGTCGLPGTKCCKKP-
HBD3    GIINTLQKYYCRVRGGRCAVLSCLPKEEQIGKCSTRGRKCCRRKK
HBD4    -----ELDRICGYGTARCR-KKCRSQEYRIGRCPN-TYACCLRK-
              *    . *      *        * *       **
```

```
HD5     -ATCYCRTGRCATRESLSGVCEISGRLYRLCCR
HD6     AFTCHCRR-SCYSTEYSYGTCTVMGINHRFCCL
         **:**    *  :  *    *.*  :  *  :*:**
```

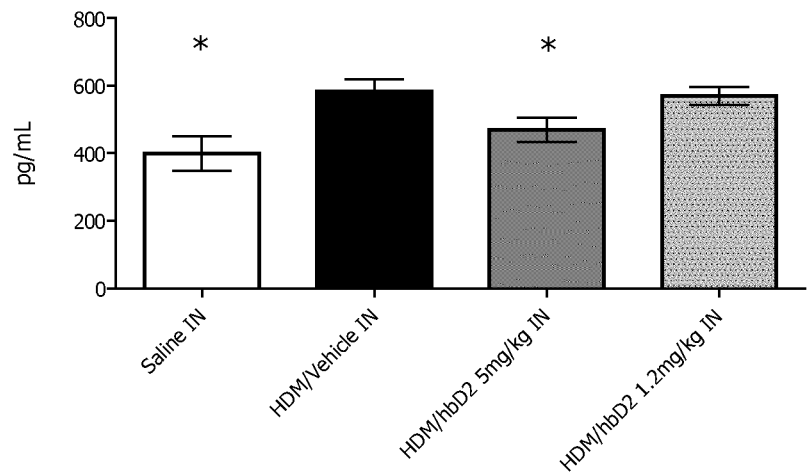
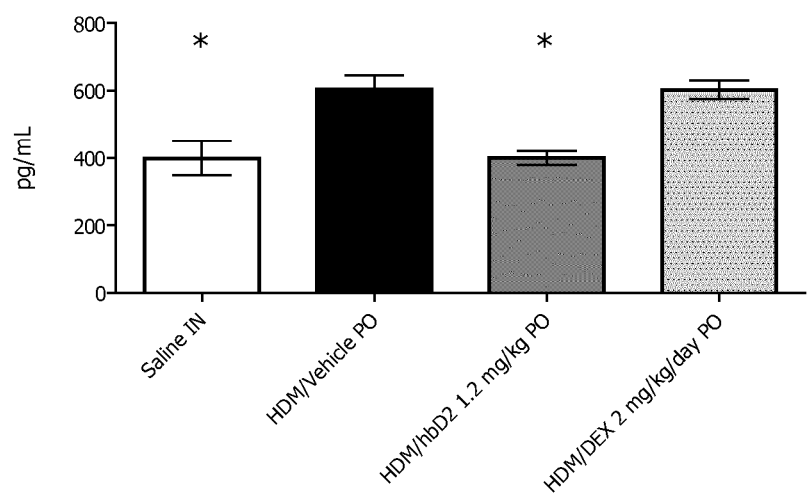
Fig. 17

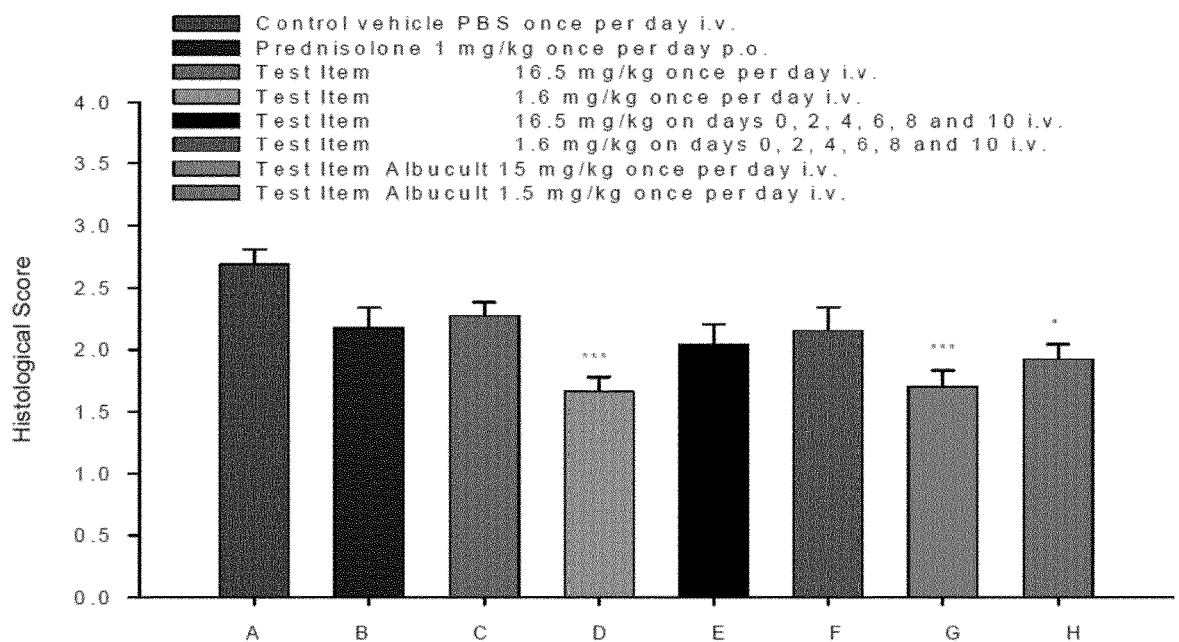

Fig. 27

| Group # | N | Sensitization s.c. (day 0) | Challenge i.n./mouse Day 14 | Treatment Days 11, 12 and 13 | Measurements and sampling 48hrs following challenge (day 16) |
|---|---|---|---|---|---|
| 1 | 12 | 100 μL of CFA dissolved in saline | 50 μL saline | - | • AHR (resistance and compliance; Buxco) N=6/group |
| 2 | 12 | 100 μg HDM/0.2 mL saline+CFA/ mouse | 25μg HDM/50μL saline | Vehicle i.n. | • BALF (total and differential cell counts) N=12/group |
| 3 | 12 | | | Vehicle p.o. | |
| 4 | 12 | | | hbD2 i.n. 1.2 mg/kg/day (0.4 mg/kg TID) | • Lungs (frozen for cytokine concentration) N=12/group |
| 5 | 12 | | | hbD2 p.o. 1.2 mg/kg/day (0.4 mg/kg TID) | |

Fig. 28

METHODS FOR TREATING INFLAMMATORY CONDITIONS OF THE LUNGS

FIELD OF THE INVENTION

The present invention relates to methods for treatment or prevention of inflammatory conditions of the lungs including asthma, mild intermittent asthma, mild persistent asthma, moderate persistent asthma, severe persistent asthma, eosinophilic asthma, neutrophilic asthma, steroid refractory asthma, status asthmaticus, pneumonia, bronchiectasis, COPD and lung cancer based on reducing airway hyper responsiveness, increasing pulmonary compliance, reducing lung inflammation, reducing perivascular or peribronchial inflammation, reducing inflammatory cell count in bronchoalveolar fluid as well as rebalancing the immune system with normalization of cytokine production and prevention of a cytokine storm by administration of a mammalian α- and/or β-defensin.

BACKGROUND

Asthma is a heterogenous inflammatory disorder of the airways characterized by chronic inflammation, airway hyper responsiveness, and by symptoms of recurrent wheezing, coughing, and shortness of breath. Asthma is a major public health problem affecting 300 million people worldwide, and has increased considerably in prevalence over the past three decades, particularly in the western world (Cosmi et al., 2011). The mechanisms of pathogenesis however, remain elusive. Steroids and combination therapies with long-acting β-agonists are the mainstay of asthma treatment. These therapies effectively suppress acute inflammatory symptoms and cytokine release but there are no preventions or cure of disease to date.

Mild to moderate allergic asthma is generally characterized by acute or chronic airway inflammation consisting of activated Th2 lymphocytes and eosinophil infiltrates in association with IgE production, mucus secreting cells, hyperplasia and metaplasia, remodeling of the airway wall and airway hyper responsiveness (AHR). The AHR is characterized by enhanced responsiveness and constriction of the airways to non-specific spasmogenic stimuli, such as methacholine (Hansbro et al., 2011). Th2 cells, through the secretion of their cytokines IL-3, IL-4, IL-5, IL-9, IL-13, amongst others, contribute to various pathological features of the disease.

Severe, neutrophilic or steroid refractory asthma has different pathological features to mild to moderate allergic asthma and is characterized by a mixed Th2/Th1 phenotype with a possible contribution of Th17 cells. Tumor necrosis factor (TNF)-α, Interferon (IFN)-γ, IL-17 and IL-27 are elevated and may induce the influx of neutrophils (rather than eosinophils) or a mixed granulocytic airway infiltrate that is characteristic for this subtype of asthma. Patients with this subtype of asthma are refractory to glucocorticoid treatment and both bacterial and viral infections are implicated in the induction and progression of disease (Hansbro et al., 2004). Also, asthmatic patients and patients with atopic dermatitis are more likely to develop infections e.g. pneumonia compared with non-atopic individuals.

The concept of treating asthma by targeting a single cytokine e.g. anti IL-4; anti IL-5; anti TNF-α has had limited success. Indeed, steroid therapy, which is currently the mainstay therapy, is thought to act by suppressing a range of pro-inflammatory pathways (Hansbro et al, 2011).

Chronic obstructive pulmonary disease (COPD). COPD is a major public health problem projected to be the fourth leading cause of death worldwide by 2020. Although persistent inhalation of toxic particles and gases are the major risk factors, with tobacco smoking being the best example of this type of risk, only 15% of smokers develop COPD (Fletcher and Peto, 1977). Although smokers have a dysfunctional immune system (Bouloukaki et al., 2011), the development and increasing disease severity of COPD progressively worsens the inflammatory cell burden (Hogg et al., 2004).

Microbiome. Infant microbiota is initially uniform across various body sites, differing in subsequent days and weeks into site-specific communities. The lung microbiome of healthy adults is dominated by the phylae Bacteroidetes, Firmicutes, and Proteobacteria with the core microbiota consisting of *Pseudomonas, Streptococcus, Prevotella, Fusobacteria, Veillonella, Haemophilus, Neisseria* and *Porphyromonas* (Charlson et al, 2011). Among asthmatics an increased frequency of Proteobacteria (in particular *Haemophilus, Moraxella* and *Neisseria*) and Firmicutes (in particular *Lactobacillus* spp.) and decreased frequency of Bacteroidetes (in particular *Prevotella*) compared with controls has been observed (Hilty et al., 2010). Similarly epidemiological data show that gut microbiota differs between asthmatic and non-asthmatic infants (Penders et al., 2007).

Defensins

Defensins represent one of the dominant innate host defences that serve to maintain a healthy microbiome and ward off potential pathogens (Wehkamp et al, 2002 and Salzman et al, 2007). Defensins are peptides possessing antimicrobial activity against Gram positive and negative bacteria, fungi and archaea as well as anti-inflammatory activity. Defensins, and in particular hBD2 have shown therapeutic potential in the treatment of Inflammatory Bowel Disease (WO 2010/007166; WO 2013/007596).

In conclusion, there is a need for new treatments of subjects suffering from inflammatory conditions of the lung. There is a particular need for treatments that can be administered through the airways for patients that can themselves administer, e.g. inhale, the drugs, and there is a need for treatment via other administration routes to patients that are unable to inhale drugs efficiently.

SUMMARY

The inventors have surprisingly demonstrated that mammalian defensins have the ability to reduce airway hyperresponsiveness (AHR) and increase airway compliance (Cdyn); reduce lung inflammation; reduce neutrophil-, eosinophil- and macrophage count in bronchio-alveolar-lavage-fluid (BALF) as well as decrease IFN-γ, TNF-α, IL-4, IL-5, IL-6, IL-8, IL-9, IL-10 and IL-13 in lung cells. The inventors have also demonstrated efficacy in reduction of histological inflammation parameters in an asthma model, for example a reduction in perivascular inflammation and peribronchial inflammation.

The data indicate that administration of mammalian defensins results in normalization or reduction of the cardinal characteristics of asthma, COPD and sarcoidosis and therefore are useful in treatment or prevention of inflammatory conditions of the lung including asthma, mild intermittent asthma, mild persistent asthma, moderate persistent asthma, severe persistent asthma, eosinophilic asthma, neutrophilic asthma, steroid refractory asthma, status asthmaticus, pneumonia, bronchiectasis, Chronic Obstructive Pulmonary Disease (COPD) and sarcoidosis.

Surprisingly it has been demonstrated in a mouse model of house dust mite allergy that oral and intranasal administration of defensins are equally efficacious at least for some of the parameters tested. This opens possibilities for treatment of inflammatory lung conditions by oral administration to subjects that have difficulty inhaling drugs. As demonstrated in the examples, a dosage of human beta-defensin 2 (hBD-2) is capable of reducing AHR, increasing Cdyn, reducing histological lung inflammation, inflammatory cell count in BALF and inflammatory cytokine production in a steroid-insensitive murine model, where mice are sensitized to ovalbumin (OVA) and infected with *C. muridarum* and in a steroid-sensitive murine model, where mice are immunized by house dust mite (HDM)+Freund's adjuvant and challenged with HDM. Without hBD-2 treatment, animals develop asthma characterized by dramatically increased AHR, decreased Cdyn, inflammatory histological changes of the lung tissue, increased white blood cell count, in particular neutrophils, eosinophils and macrophages and increased concentration of inflammatory cytokines.

Because of these observations, the inventors also contemplate the use of defensins in general to treat inflammation in the lungs. Examples of conditions that can give rise to lung inflammation include sarcoidosis, lung cancer and various types of medical treatment that affect the host defence including but not limited to antimicrobial treatment, chemotherapy, immunotherapy, immunosuppressive therapy, and radiation therapy.

The inventors have demonstrated experimentally that defensins rebalance the immune system by completely normalizing cytokine levels thus preventing a cytokine storm contrary to current asthma treatment with e.g. interleukin antibodies, that knocks out a given cytokine or general immune suppression, which results in general suppression of the innate immune system. Therefore defensins represent a promising alternative to current treatments.

The inventors have further demonstrated that defensins are capable of exerting their effect in the lungs not only when administered directly into the lung but more importantly and surprisingly, when administered solely orally into the gut.

Oral administration in the treatment of an asthma attack as well as for maintenance treatment will facilitate the life of asthmatics across the world.

Therefore in one aspect, there is provided a method of treatment and/or prevention of inflammatory diseases of the respiratory system including rebalancing of the immune system, normalization of cytokine production and prevention of a cytokine storm, the method comprising oral or intrapulmonary administration of at least one defensin preferably wherein the subject suffers from asthma.

In other aspects there is provided a method for treatment and/or prevention of a disease selected from the group consisting of mild intermittent asthma, mild persistent asthma, moderate persistent asthma, severe persistent asthma, eosinophilic asthma, neutrophilic asthma, steroid refractory asthma, status asthmaticus, bronchiectasis, bronchitis, COPD, sarcoidosis, pneumonia and emphysema, lung fibrosis, preferably steroid refractory asthma, said method comprising administration of at least one defensin.

Further is provided methods of treatment and/or prevention of lung cancer in a subject, said method comprising administration of at least one defensin to said subject, and methods of reducing histological lung inflammation, perivascular and bronchiovascular inflammation, inflammatory cell count in bronchoalveolar lavage fluid, and/or inflammatory cytokine production in lung tissue homogenates in a subject in need thereof, said method comprising said method comprising administration of at least one defensin to said subject.

In a still further aspect, there is provided a method of reducing histological lung inflammation, inflammatory cell count in bronchoalveolar lavage fluid, rebalancing the immune system with normalization of inflammatory cytokine production in lung tissue homogenates and prevention/treatment of a cytokine storm in a subject in need thereof, said method comprising administration of at least one defensin to said subject.

In another aspect there is provided a method of increasing pulmonary compliance, of reducing airway hyper responsiveness, and/or in increasing the peak expiratory flow in a subject in need thereof, said method comprising administration of at least one defensin to said subject.

A method of increasing forced expiratory volume at 1 second (FEV1) and/or peak expiratory flow rate PEFR, or reducing PEFR variability in a subject in need thereof, said method comprising administration of at least one defensin to said subject.

By administering at least one defensin to a subject, gene richness, the number of phylae can be increased, butyrate and/or tryptophan production can be increased and acetate production from lung microbiota can be decreased in a subject in need thereof.

Further, there is provided a method of maintaining and/or stabilizing a normal microbiota in the lung, increasing the presence and abundance of key commensal bacteria and short chain fatty acid and/or butyrate and/or tryptophan producers in a subject in need thereof, said method comprising administration of at least one defensin to said subject.

In other aspects, the disclosure relates to a defensin polypeptide for use in a method of treatment according to any of the methods described herein and to use of a defensin polypeptide for the preparation of a medicament for the treatment of a disorder as defined herein.

DESCRIPTION OF DRAWINGS

FIG. 2. Schematic outline of the experimental set up for investigating the effects of mammalian β-defensins in a murine steroid-sensitive model of asthma, where the mice are immunized by house dust mite (HDM)+Freund's adjuvant and challenged with HDM.

\* indicates positions which have a single, fully conserved residue.

: indicates that one of the following 'strong' groups is fully conserved:

S,T,A; N,E,Q,K; N,H,Q,K; N,D,E,Q; Q,H,R,K; M,I,L,V; M,I,L,F; H,Y; F,Y,W.

• indicates that one of the following 'weaker' groups is fully conserved:

C,S,A; A,T,V; S,A,G; S,T,N,K; S,T,P,A; S,G,N,D; S,N,D, E,Q,K; N,D,E,Q,H,K; N,E,Q,H,R,K; V,L,I,M; H,F,Y.

Figures 3A, 3B, 4:
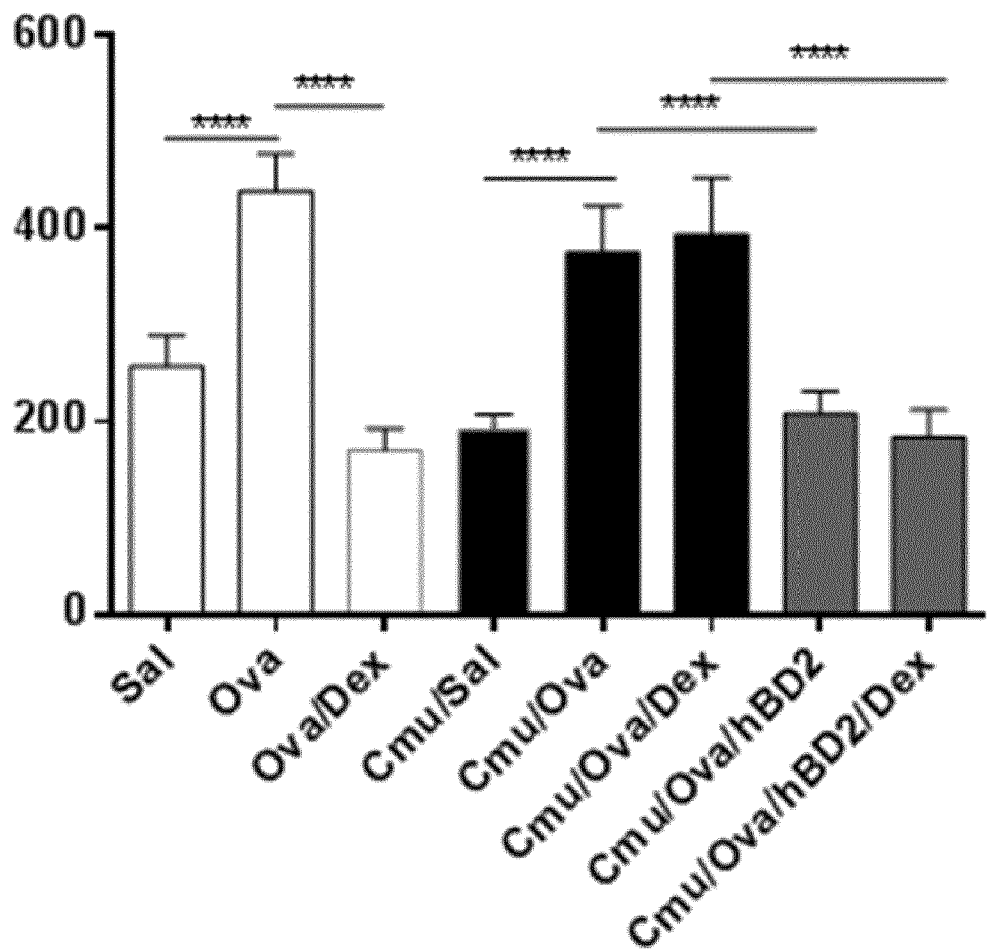
FIG. 3*a*. Clustal W (2.1) multiple sequence alignment of human beta defensin 1-4: In the Clustal W alignments.

FIG. 3*b*. Clustal alignment of HD5 and HD6.

FIG. 4: Airway hyper-responsiveness in the Ovalbumin/ *C. muridarum* murine steroid-insensitive asthma model following intranasal administration of hBD-2. Y-axis shows Rn—airway-specific resistance units (tidal volume of 8 mL/kg at a respiratory rate of 450 breaths/minute). **** indicates statistically significant differences using Mann Whitney test with a p-value of p<0.05

Figure 5A:
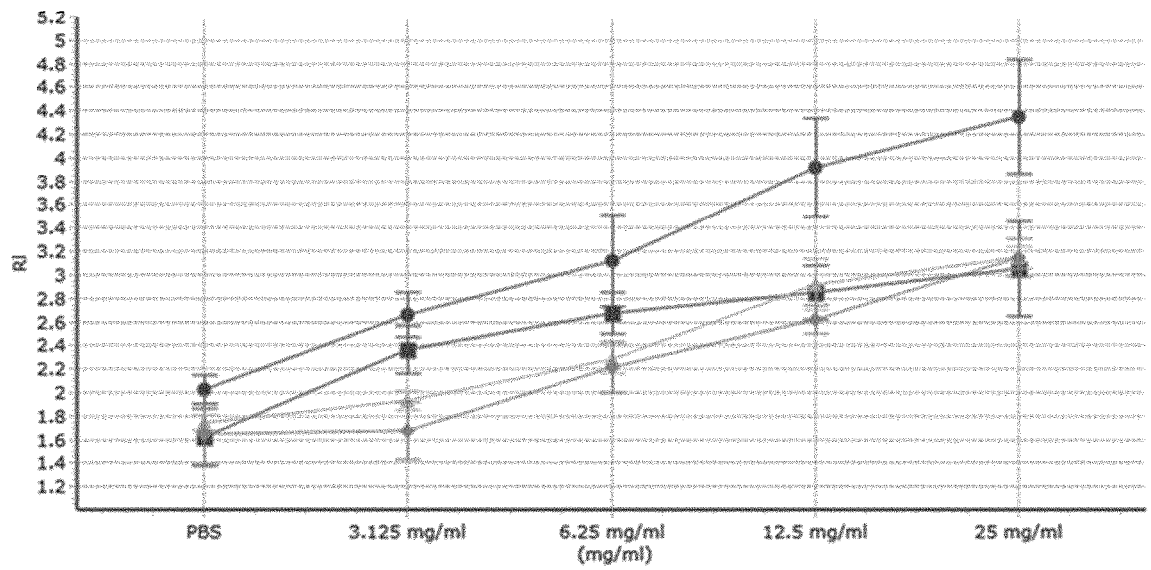
Figure 5B:
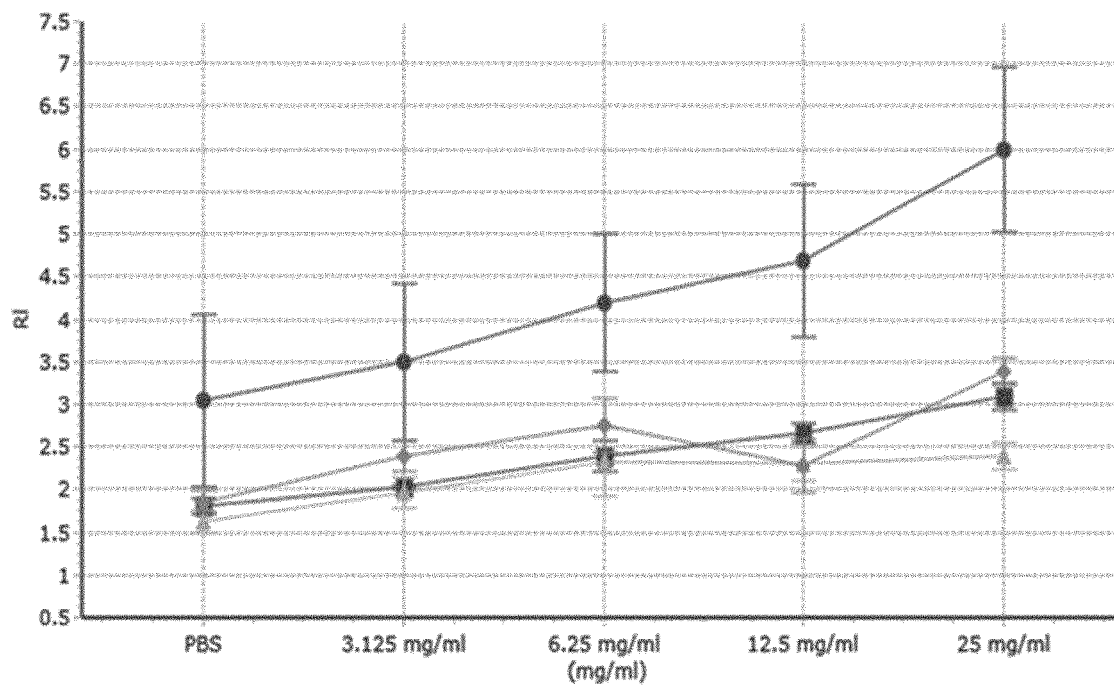

FIGS. 5a and 5b: Airway hyper responsiveness in the House Dust Mite murine steroid-sensitive asthma model following intranasal (FIG. 5a) and oral (FIG. 5b) administration of hBD-2 respectively. Saline is the non-challenged control. HDM/Vehicle is the House Dust Mite challenged control treated with vehicle. "hBD2 IN 1.2 mpk" is hBD2 administered intranasally at 1.2 mg/kg. 5 mpk is 5 mg/kg.

Legend, FIG. 5a: ●—Vehicle IN; ■—hBD2 IN 1.2 mpk; ▲—saline; ◆—hBD2 IN 5 mpk.

Legend, FIG. 5b: ●—HDM/Vehicle IN; ■—saline; ▲—HDM/dexamethasone; ◆—HDM/hBD2 1.2 mg/kg p.o.

Figure 6A:
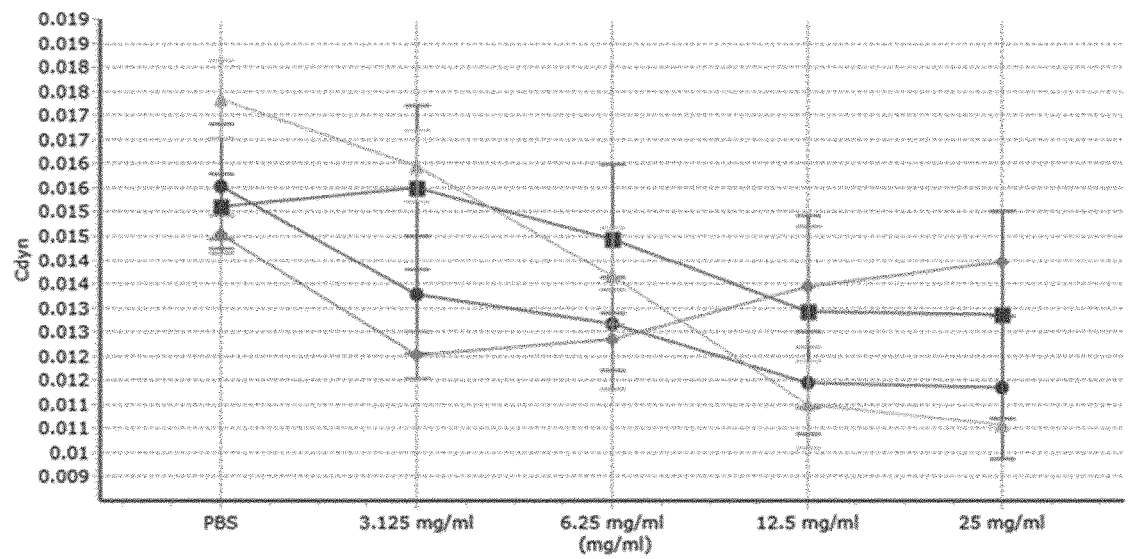
Figure 6B:
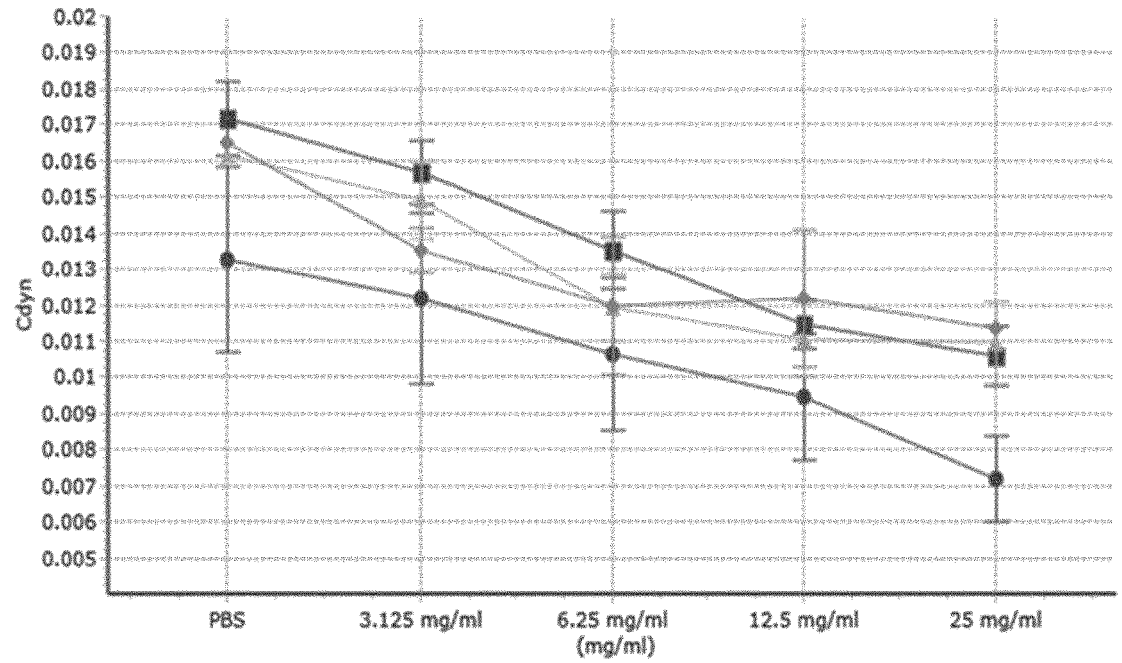

FIGS. 6a and 6b: Pulmonary compliance in the House Dust Mite murine steroid-sensitive asthma model following intranasal (FIG. 6a) and oral (FIG. 6b) administration of hBD-2 respectively.

Legend, FIG. 6a: ●—Vehicle IN; ■—hBD2 IN 1.2 mpk; ▲—saline; ◆—hBD2 IN 5 mpk.

Legend, FIG. 6b: ●—HDM/Vehicle IN; ■—saline; ▲—HDM/dexamethasone; ◆—HDM/hBD2 1.2 mg/kg p.o.

Figure 7:
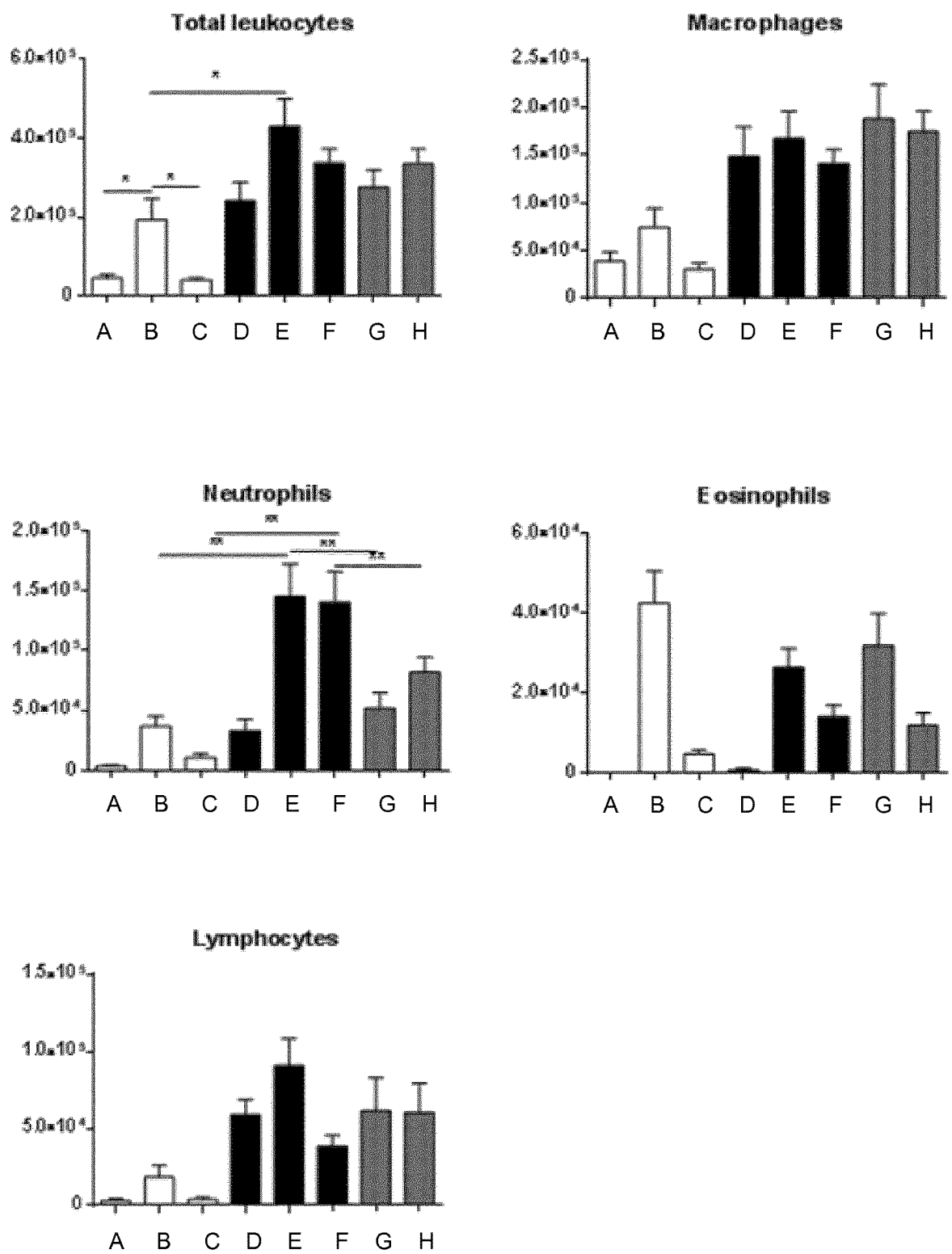

FIG. 7. Total and differential cell count in BALF in the Ovalbumin/C. muridarum murine steroid-insensitive asthma model following intranasal administration of hBD-2.

Figure Legend:
A: SPG/Sal
B: SPG/Ova
C SPG/Ova/Dex
D: Cmu/Sal
E: Cmu/Ova
F: Cmu/Ova/Dex
G: Cmu/Ova/hBD2
H: Cmu/Ova/hBD2/Dex
Treatment Groups

|  | D 0 | D 12 + 13 | D 14 | D 32 |  | D 33 + 34 |
|---|---|---|---|---|---|---|
| SPG/Sal | Sal IP | Ova IN | SPG IN | PBS IN | Ova IN |
| Cmu/Sal | Sal IP | Ova IN | Cmu IN | PBS IN | Ova IN |
| SPG/Ova | Ova IP | Ova IN | SPG IN | PBS IN | Ova IN |
| Cmu/Ova | Ova IP | Ova IN | Cmu IN | PBS IN | Ova IN |
| SPG/Ova/Dex | Ova IP | Ova IN | SPG In | Dex IN | Ova + Dex IN |
| Cmu/Ova/Dex | Ova IP | Ova IN | Cmu IN | Dex IN | Ova + Dex IN |
| Cmu/Ova/hBD-2 | Ova IP | Ova IN | Cmu IN | hBD2 IN | Ova + hBD2 IN |
| Cmu/Ova/hBD-2/Dex | Ova IP | Ova IN | Cmu IN | hBD2 + Dex IN | Ova + hBD2 + Dex IN |

Figure 8A:
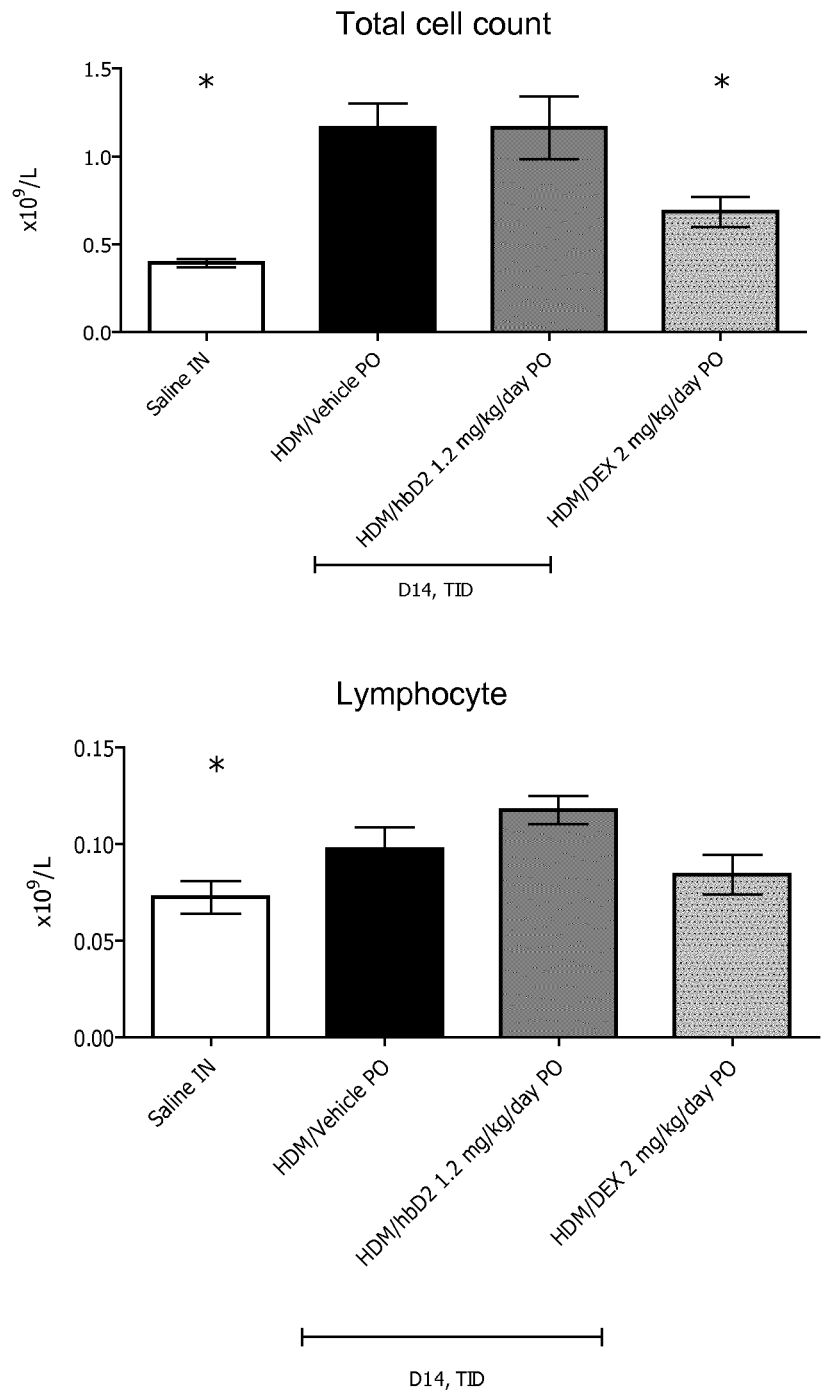
Figure 8A:
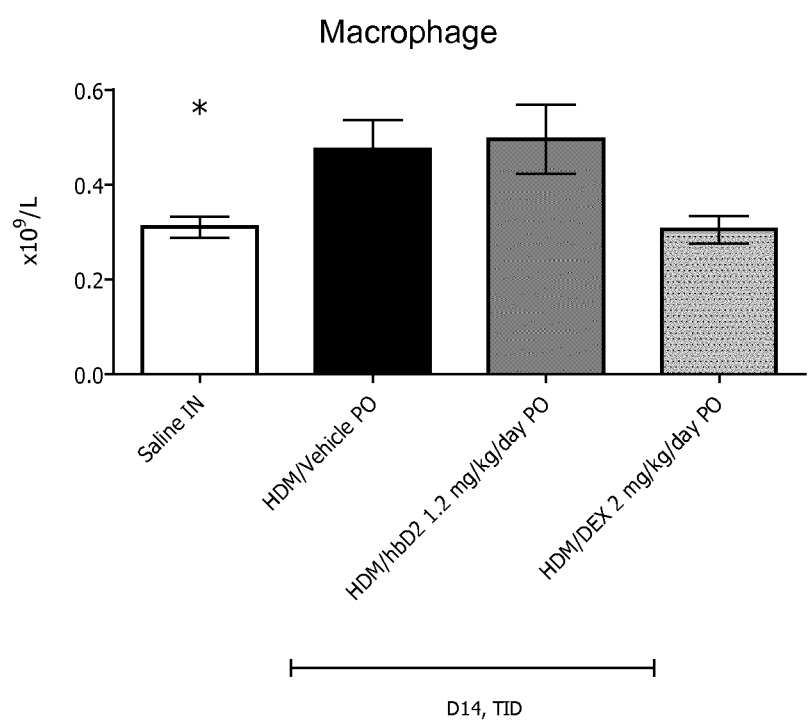
Figure 8A:
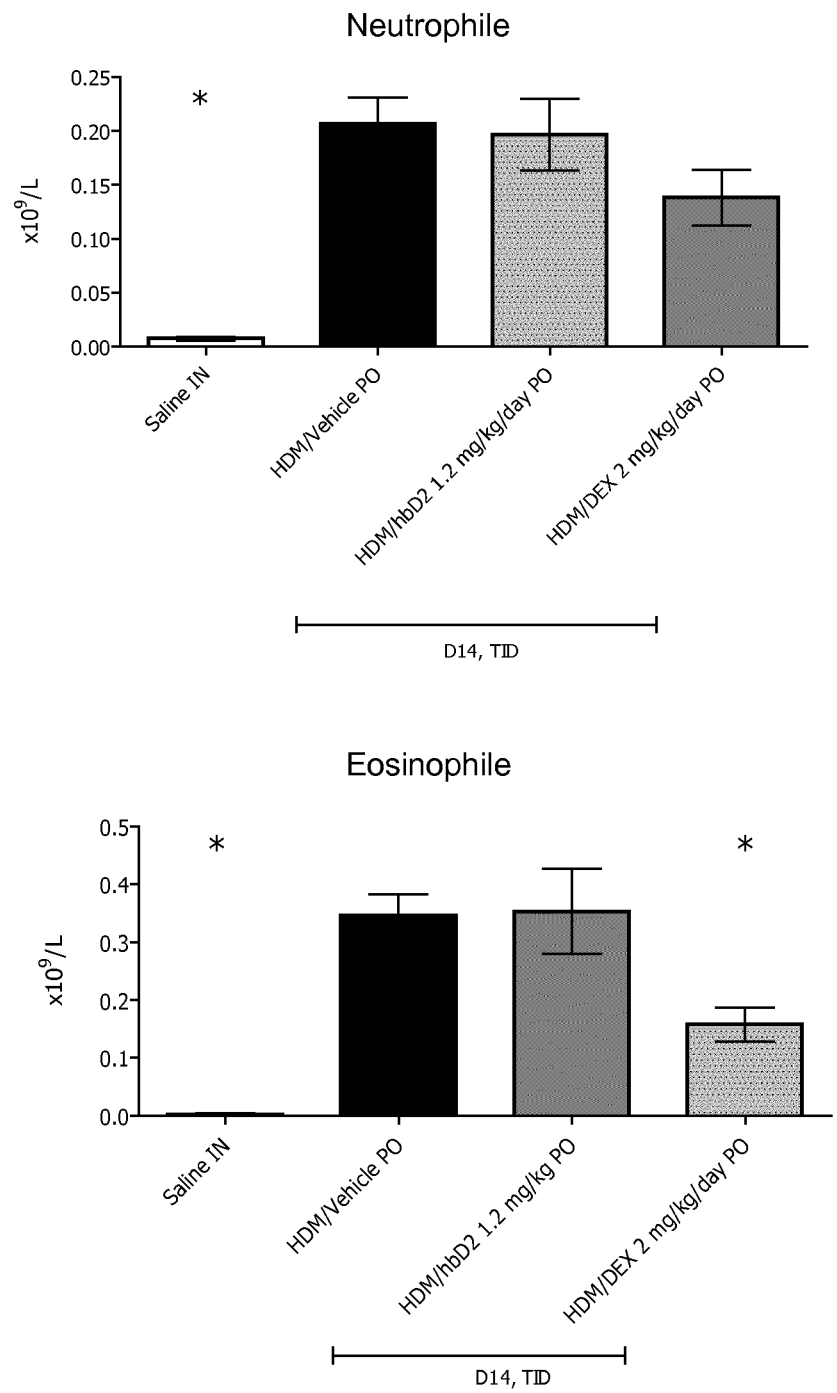
Figure 8B:
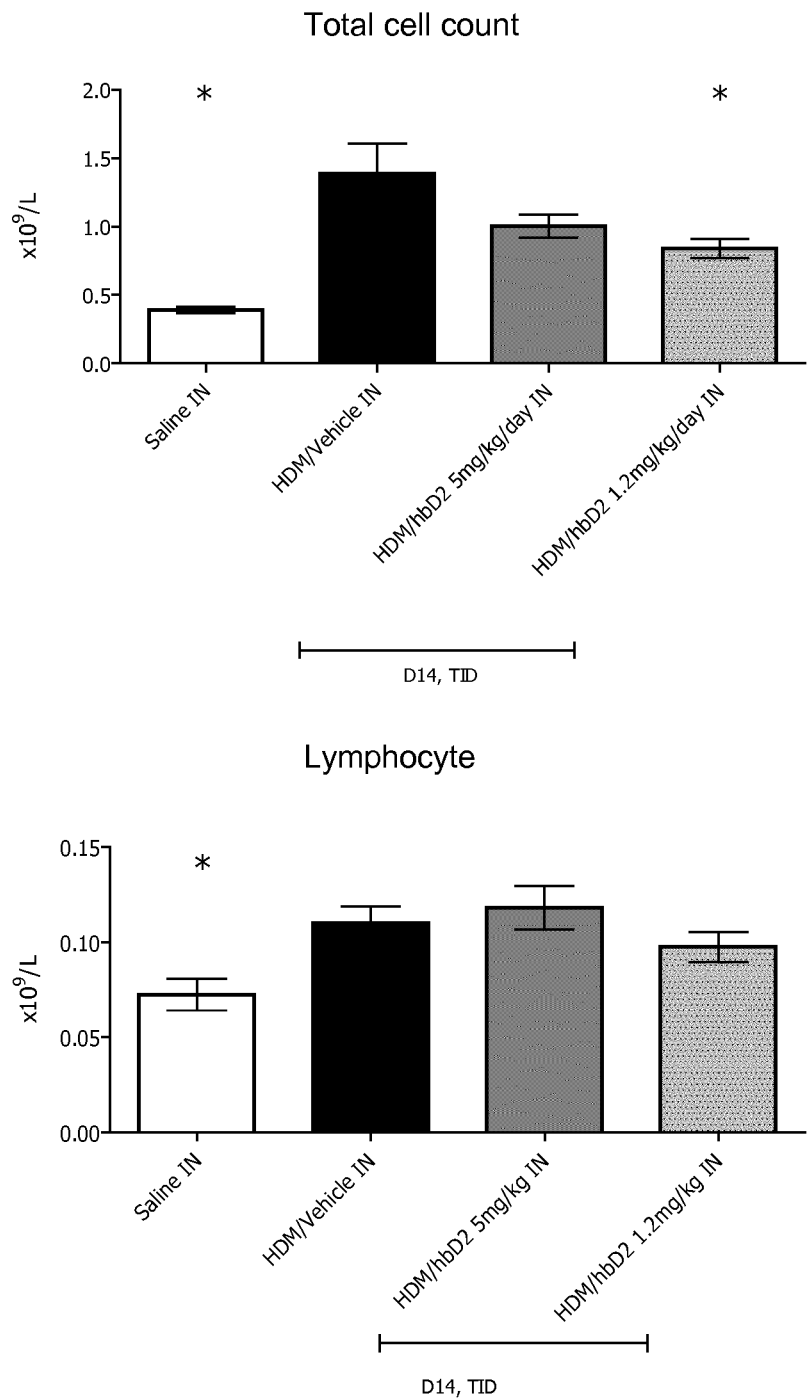
Figure 8B:
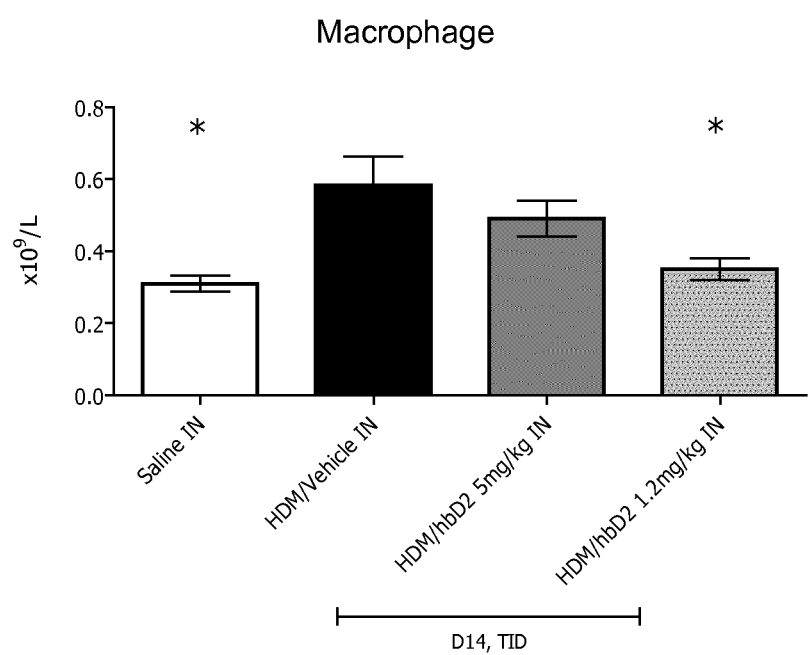
Figure 8B:
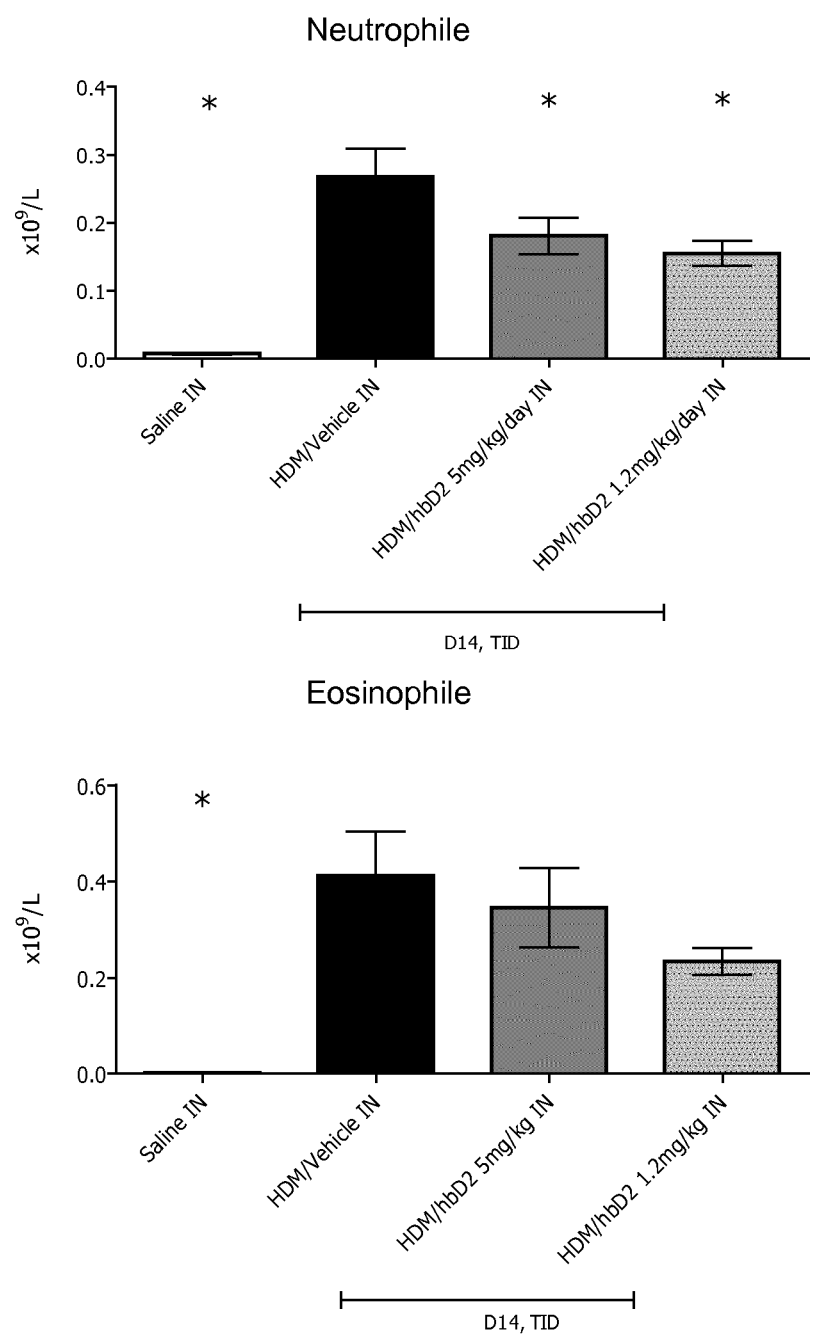

FIGS. 8a and 8b: Total and differential cell count in BALF in the House Dust Mite murine steroid-sensitive asthma model following intranasal and oral administration of hBD-2 respectively. FIG. 8a represent the animals treated peroral hBD2. FIG. 8b represent results from animals receiving intranasal hBD2. Results are shown as mean+/−SEM. *p<0.05 vs vehicle, unpaired test.

Figure legend. Saline IN is the unchallenged and untreated control. HDM/Vehicle represent the untreated but HDM challenged animals. HDM are the animals challenged with house dust mites. PO is peroral administration and IN is intranasal administration. Columns labelled * are statistically significantly different from the vehicle treated control.

FIG. 9-18. Cytokine concentrations of IFN-γ (FIG. 9), TNF-α (FIG. 10), IL-1β (FIG. 11), IL-4 (FIG. 12), IL-5 (FIG. 13), IL-6 (FIG. 14), IL-8 (FIG. 15), IL-9 (FIG. 16), IL-10 (FIG. 17) and IL-13 (FIG. 18) in the House Dust Mite murine steroid-sensitive asthma model following intranasal and oral administration of hBD-2 respectively. Each figure has data from the intranasal arm on the left and the peroral arm on the right. Results are shown in pg/mL as the mean+/−SEM. *p<0.05 vs. vehicle, Mann Whitney test.

Figure 19:
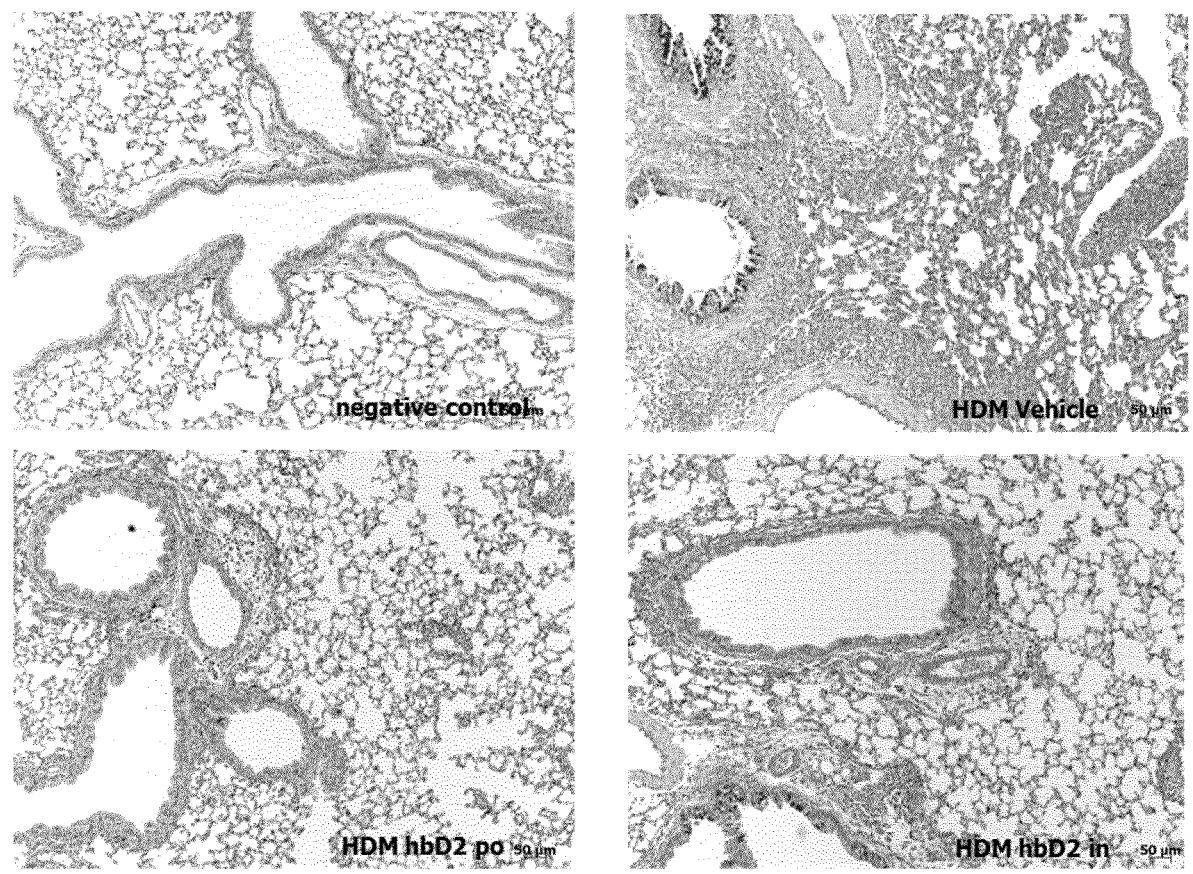

FIG. 19. Lung histology with H&E/PAS preparation in the House Dust Mite murine steroid-sensitive asthma model following intranasal and oral administration of hBD-2 respectively. Upper left panel: untreated and unchallenged control. Upper right panel: untreated and HDM challenged control. Lower left panel: HDM challenged treated with hBD2 PO. Lower right panel: HDM challenged treated with hBD2 IN. 50× enlargement.

Figure 20:
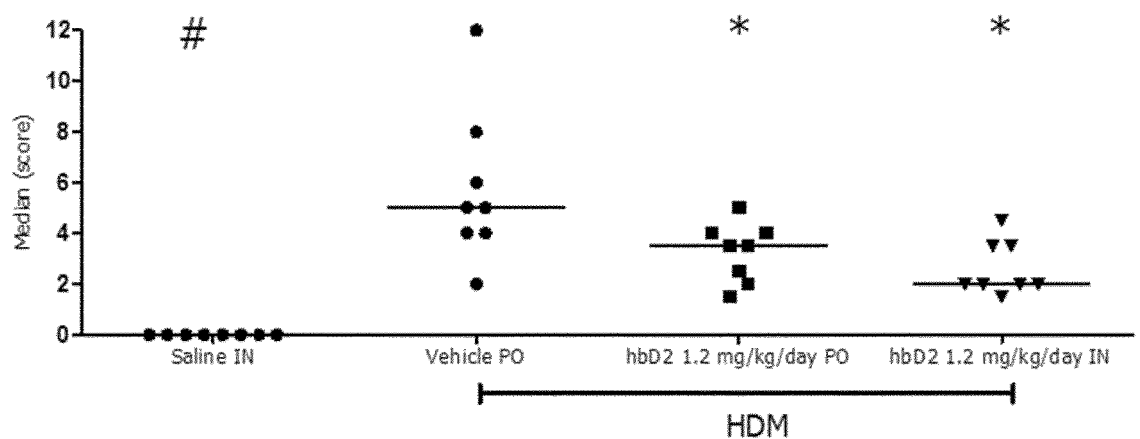

FIG. 20. Lung inflammation severity in the House Dust Mite murine steroid-sensitive asthma model following intranasal and oral administration of hBD-2 respectively.

*p<0.05 vs vehicle, Mann Whitney test p<0.05 vs vehicle, Wilcoxon Signed Rank Test.

Figure 21:
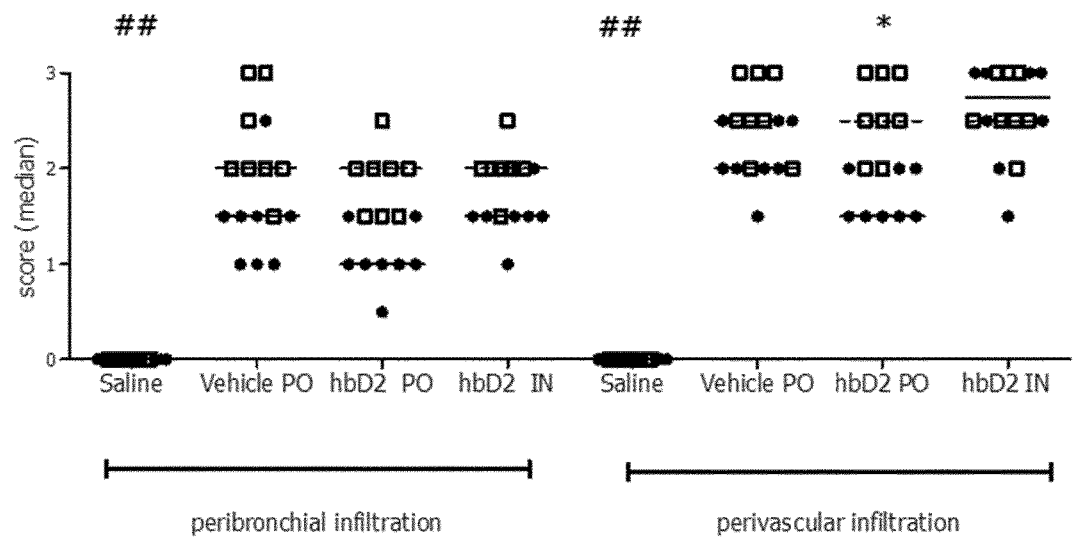

FIG. 21. Perivascular and peribronchial inflammation in the House Dust Mite murine steroid-sensitive asthma model following intranasal and oral administration of hBD-2 respectively. ◆ eosinophils; □ monocytes.

*p<0.05 vs vehicle for perivascular infiltration of eosinophils, Mann Whitney test p<0.05 vs vehicle for perivascular/peribronchial infiltration of eosinophils and monocytes, Wilcoxon Signed Rank Test.

Figure 22:
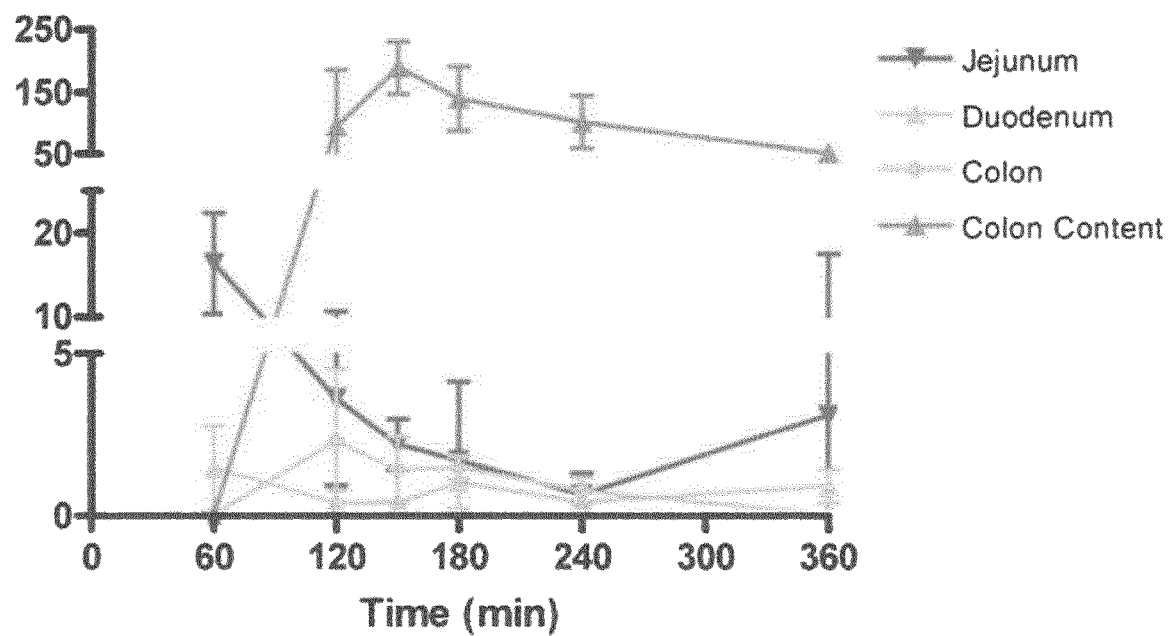

FIG. 22. Pharmacokinetic data following oral administration of 4 mg/kg hBD-2 to female NMRI mice. The Y-axis shows hBD2 in µg/g tissue. The results are given as group mean+/−SEM.

Figure 23:
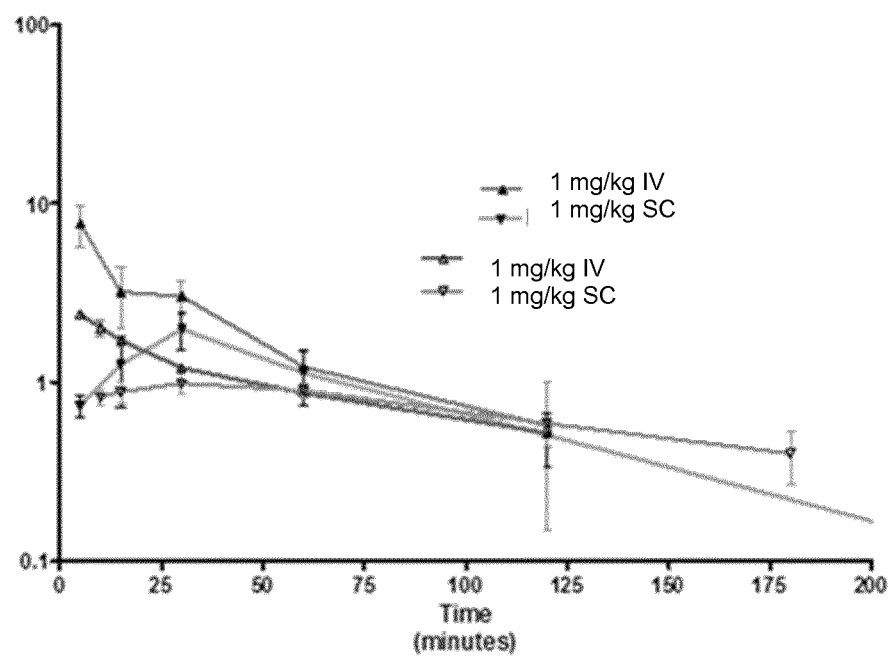

FIG. 23. Pharmacokinetic data for hBD-2 following subcutaneous and intravenous administration of 1 mg/kg respectively. The Y-axis shows hBD2 in µg/mL. The different curves represent different experiments and detection methods (HPLC and ELISA).

Figure 24:
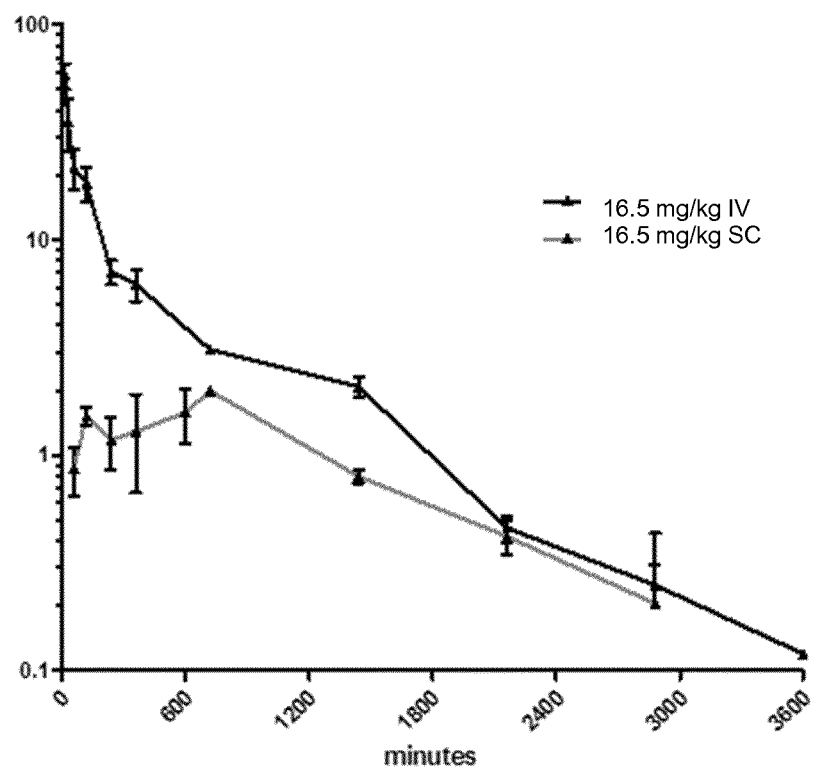

FIG. 24. Pharmacokinetic data for "hBD-2-albumin fusion N-terminal" following subcutaneous and intravenous administration of 16.5 mg/kg respectively. The Y-axis shows the concentration of the fusion protein in µg/mL. The results are the mean of 4 mice/sampling time+/−SD.

Figure 25:
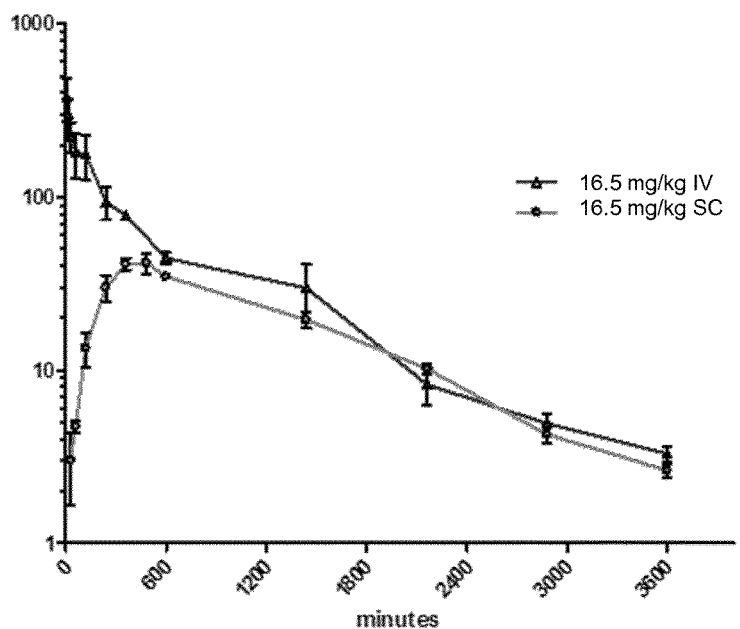

FIG. 25. Pharmacokinetic data for "hBD-2-albumin fusion C-terminal" following subcutaneous and intravenous administration of 16.5 mg/kg respectively. The Y-axis shows the concentration of the fusion protein in µg/mL. The results are the mean of 4 mice/sampling time+/−SD.

Figure 26:
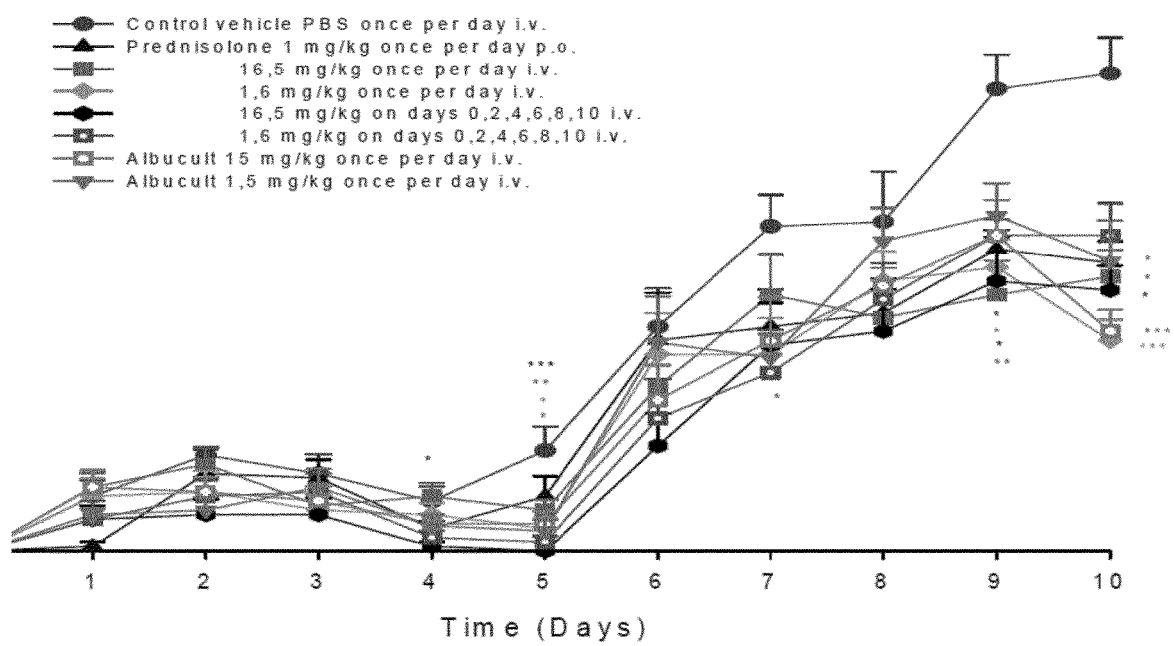

FIG. 26. Disease Activity Index score progression during the study with IV administration of "hBD-2-albumin fusion C-terminal". Results are shown as the mean+/− standard error of the mean for 9-10 animals per group. Significant differences from control (vehicle) group values at a given date are shown as *P<0.05; P<0.01; *P<0.001 (Kruskal-Wallis test for non-parametric data. Albucult® is a recombinant albumin available from NovoZymes NS. Where no compound is mentioned in the graph, the compound is hBD2-albumin fusion C-terminal.

FIG. 27. Histological score proximal colon of "hBD-2-albumin fusion C-terminal". Histological score of proximal colon samples. Results are shown as the mean±the standard error of the mean for n=9-10 animals per group. Significant differences from control (vehicle) group values at a given date are shown as ***P<0.001; *P<0.05 (Kruskal-Wallis Test+post-test of Dunn for non-parametric data). Albucult® is a recombinant albumin available from NovoZymes NS. Where no compound is mentioned in the graph, the compound is hBD2-albumin fusion C-terminal.

FIG. 28. Schematic outline of the experimental set up for investigating the effects of mammalian defensins in a murine steroid-sensitive model for prevention of asthma, where the mice are immunized by house dust mite (HDM)+Freund's adjuvant and challenged with HDM.

Figure 29:
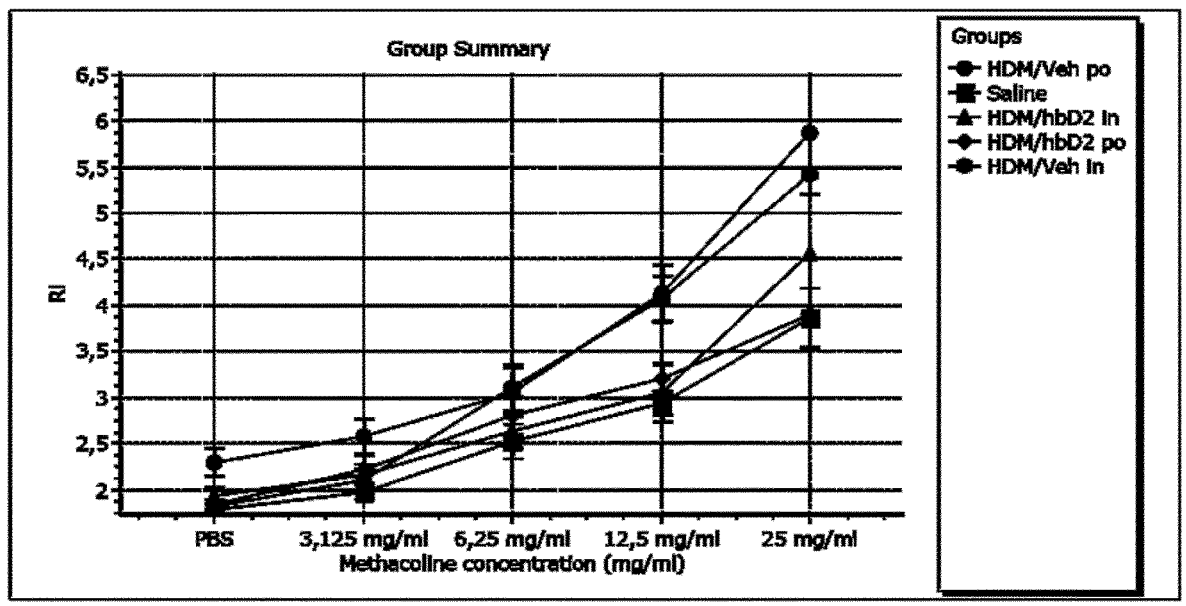

FIG. 29: Airway hyper responsiveness in the murine House Dust Mite steroid-sensitive asthma model following prophylactic intranasal and oral administration of hBD-2 respectively.

Figure 30:
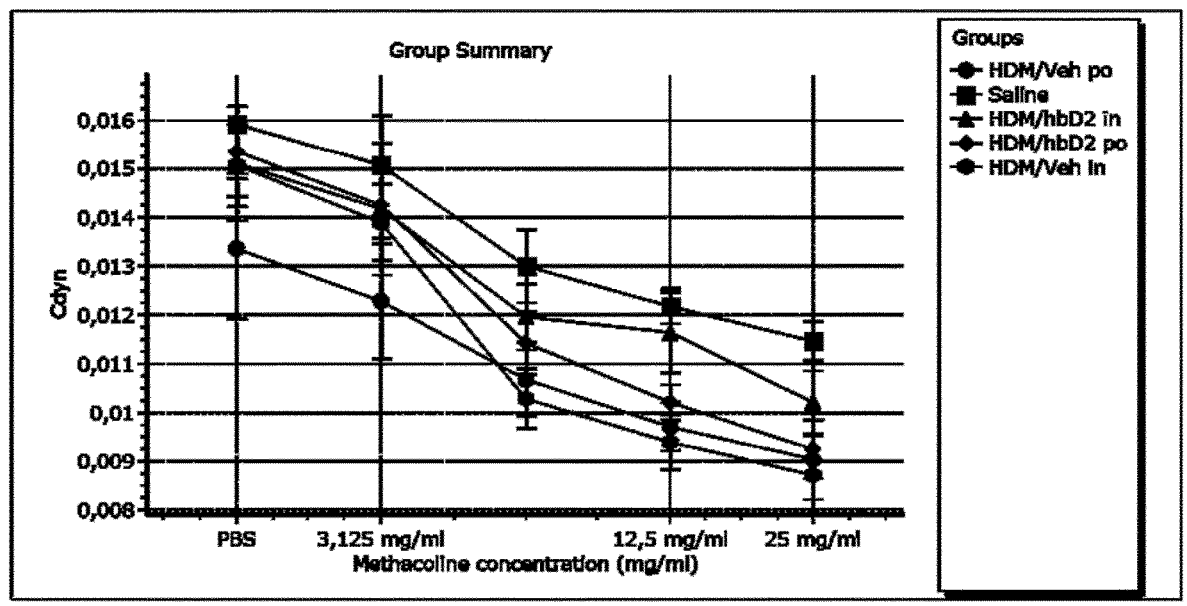

FIG. 30: Pulmonary compliance in the murine House Dust Mite steroid-sensitive asthma model following prophylactic intranasal and oral administration of hBD-2 respectively.

Figure 31:
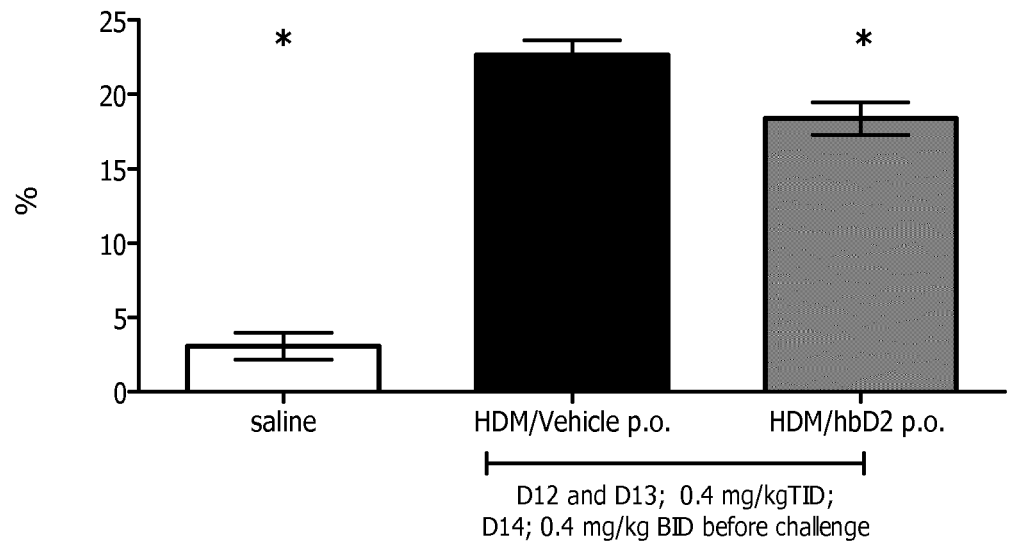
Figure 32:
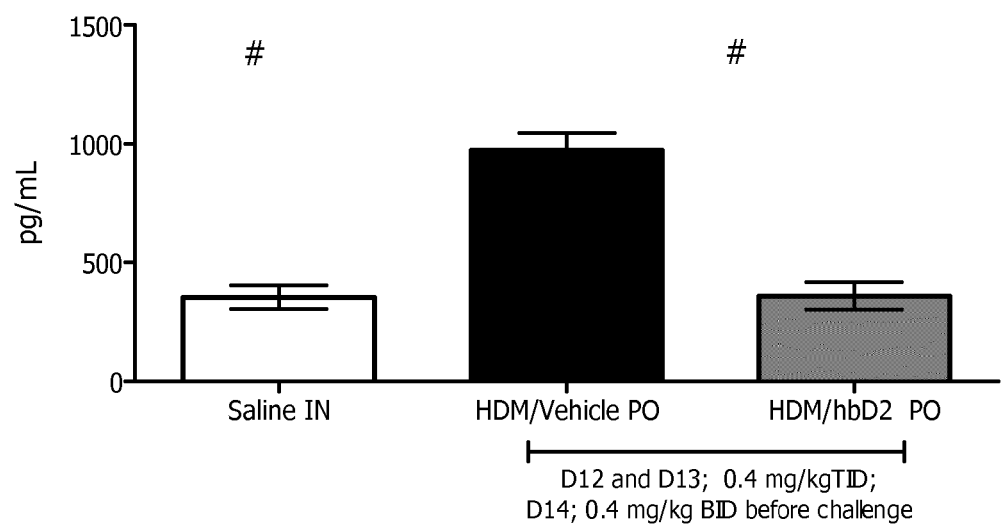
Figure 33:
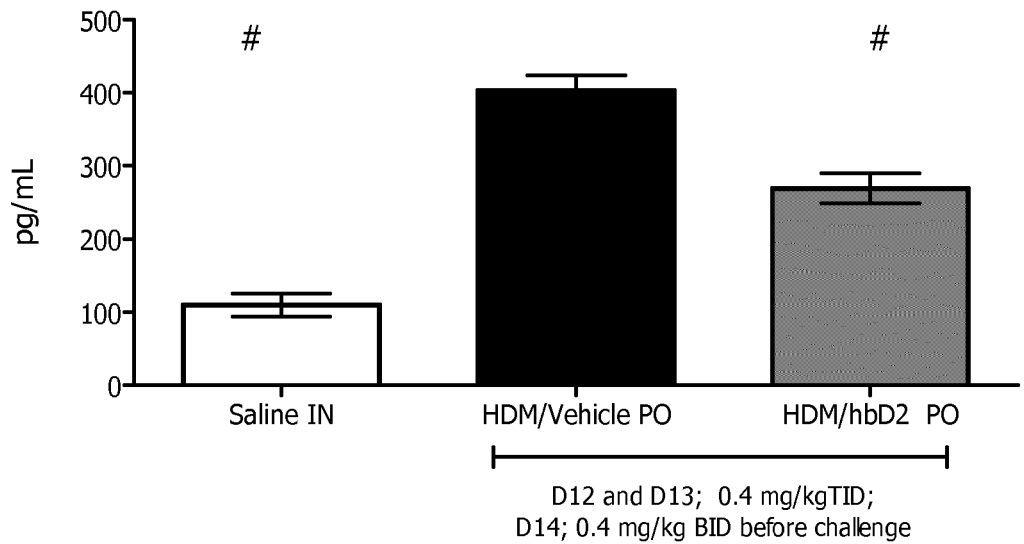
Figure 34:
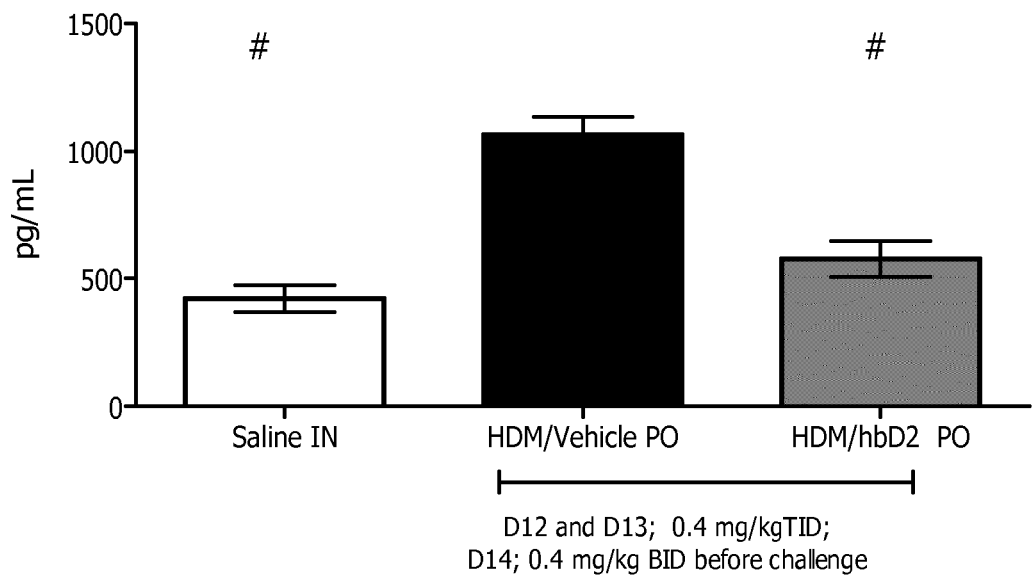
Figure 35:
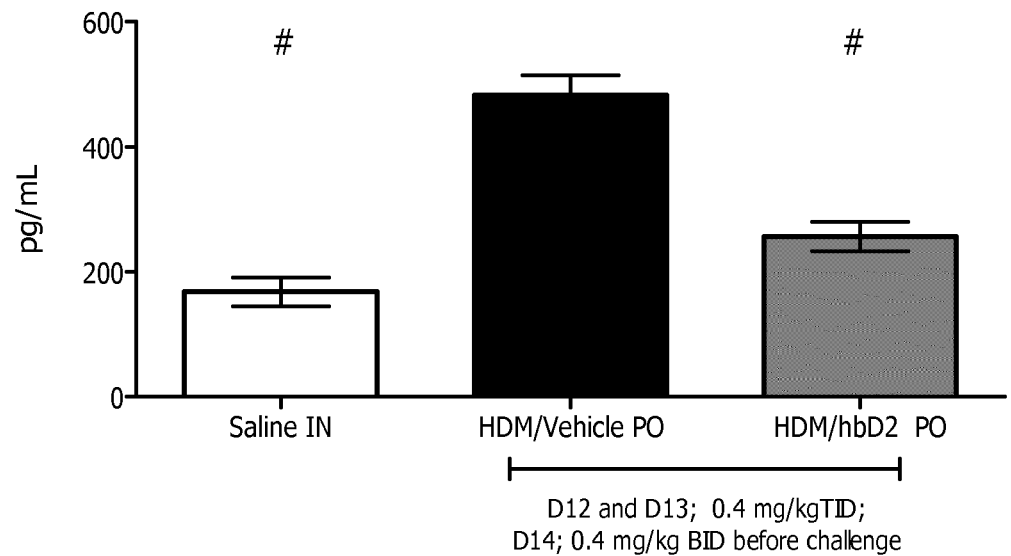
Figure 36:
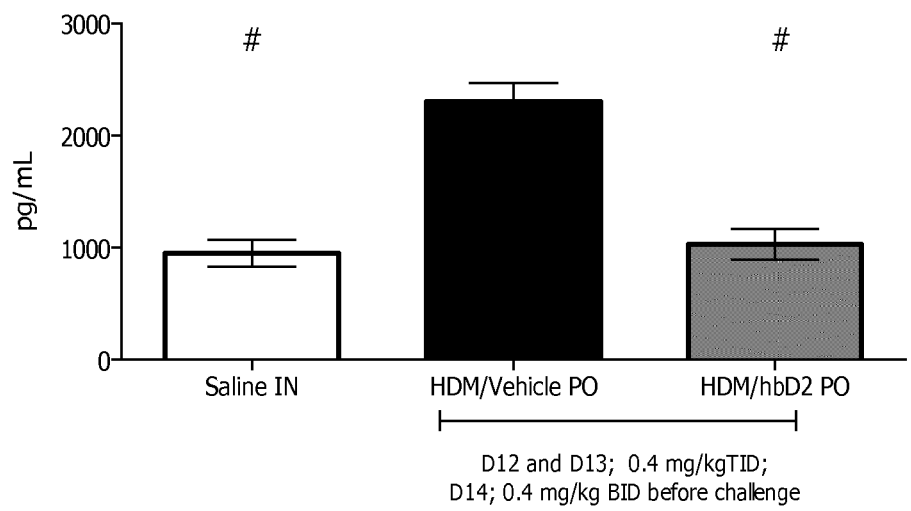
Figure 37:
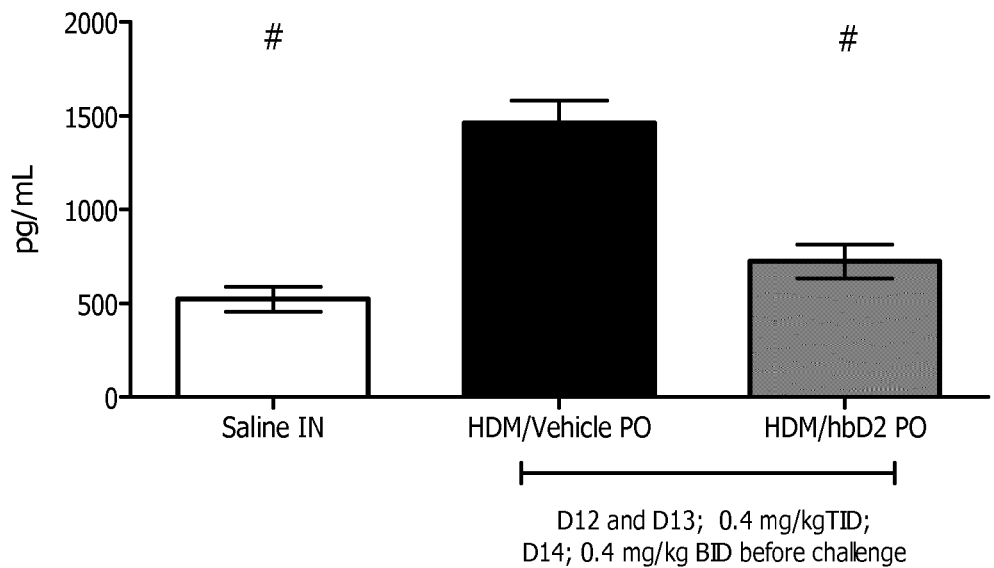

FIG. 31: Neutrophil cell count in BALF in the House Dust Mite murine steroid-sensitive asthma model following prophylactic oral administration of hBD-2. *p<0.05 vs vehicle, Mann Whitney test.

FIG. 32-37. Cytokine concentrations (pg/mL) of TNF-α (FIG. 32), IL-4 (FIG. 33), IL-5 (FIG. 34), IL-6 (FIG. 35), IL-9 (FIG. 36) and IL-13 (FIG. 37) in lung homogenate in the House Dust Mite murine steroid-sensitive asthma model following prophylactic oral administration of hBD-2. Results are shown as the mean+/−SEM.
*p<0.05 vs vehicle, Mann Whitney test.

Figure 38:
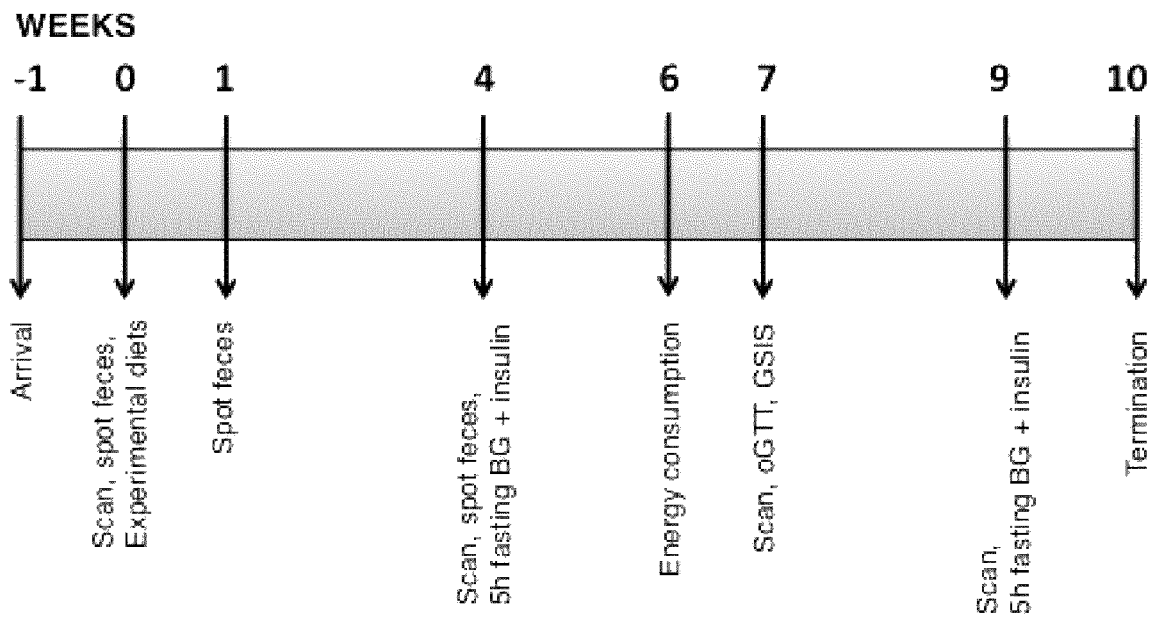
Figure 39:
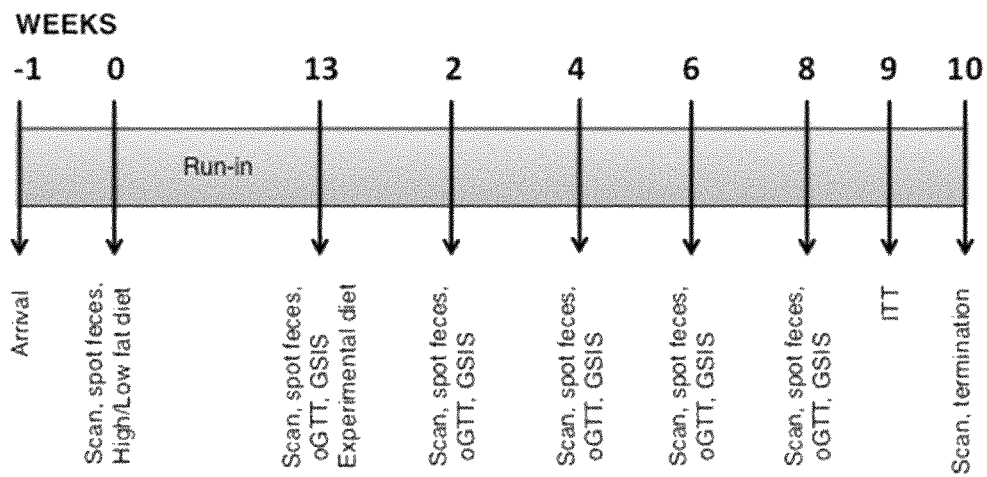

FIG. 38-39. Schematic outline of the experimental setup for investigating the effects of mammalian defensins (HD5, hBD2 and HD5+hBD2) on the composition of the microbiota in a high fat diet murine model.

Figure 40:
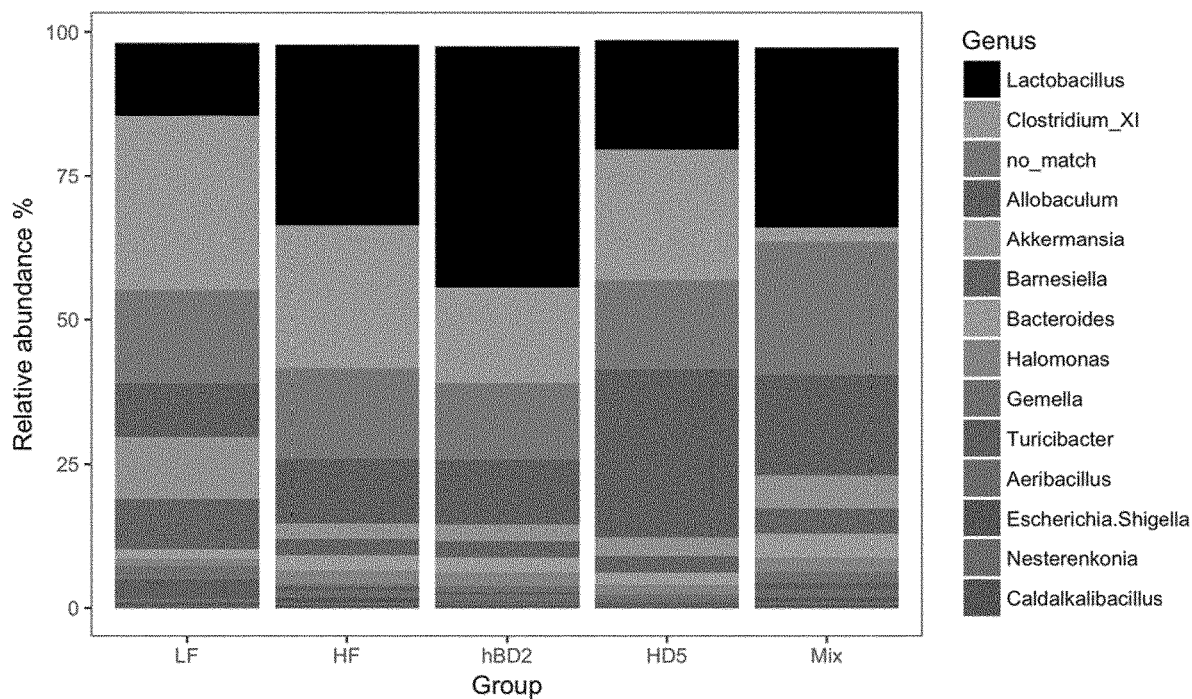

FIG. 40. Genus analysis of microbial abundance following prophylactic treatment with oral HD5, hBD2 and HD5+hBD2 in a murine high fat diet model.

Figure 41:
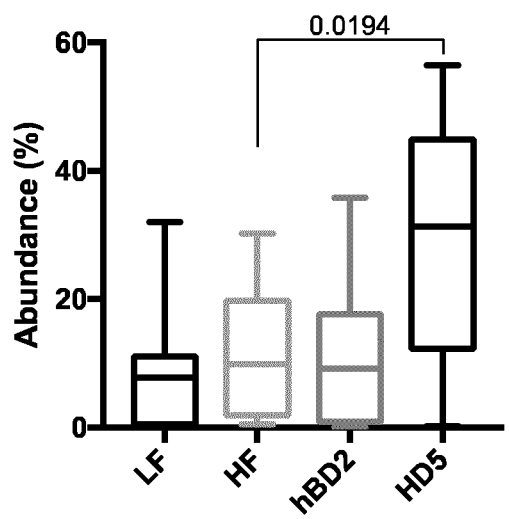

FIG. 41. Abundance of Allobaculum in the small intestine following prophylactic treatment with oral HD5 and hBD2 in a murine high fat diet model.

Figure 42:
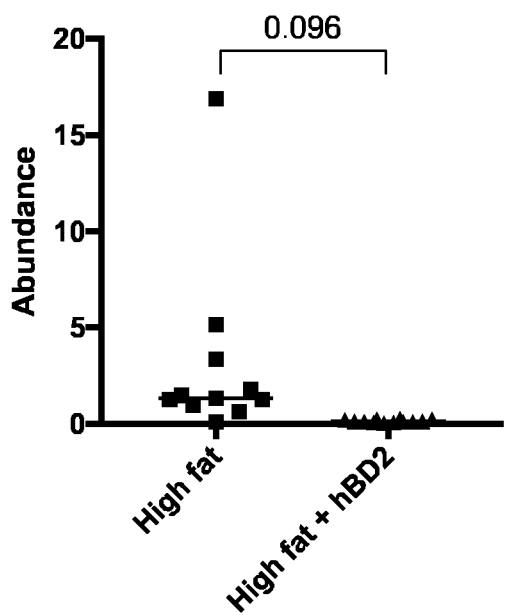

FIG. 42. Abundance of Lactobacillaceae in colon following prophylactic treatment with oral hBD2 in a murine high fat model.

Figure 43:
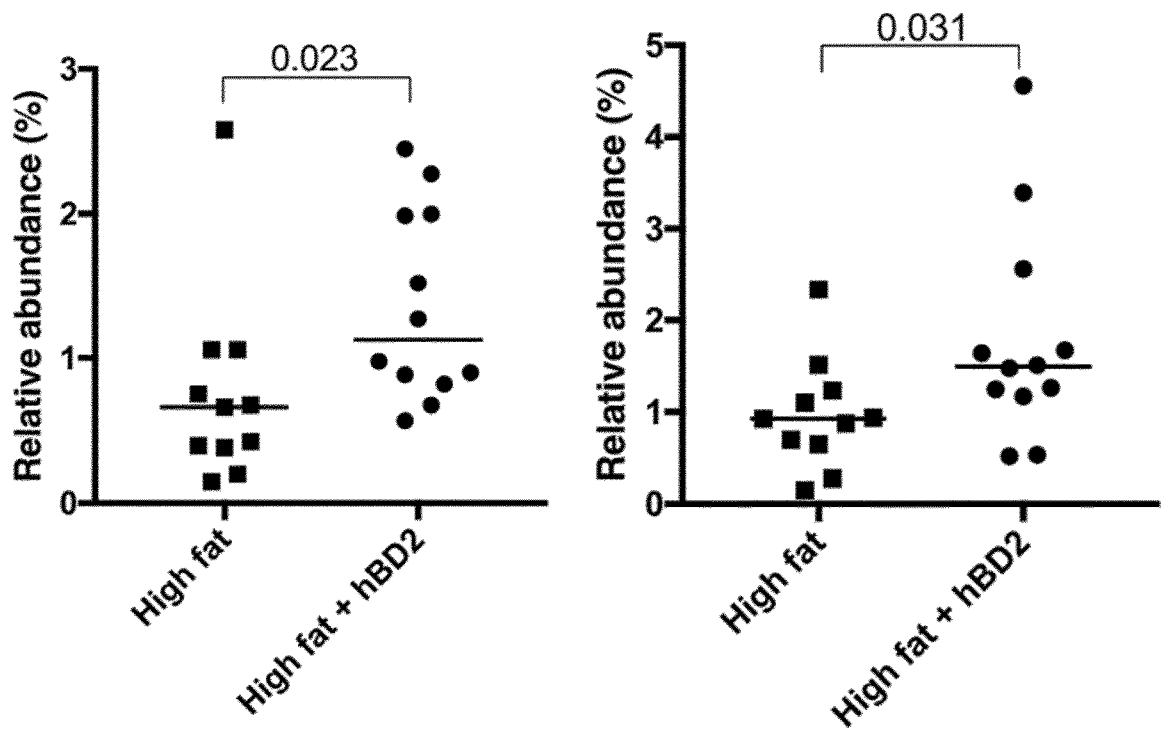

FIG. 43. Relative abundance of Barnesiella in colon following 4 (left panel) and 10 weeks (right panel) of prophylactic treatment with oral hBD2 in a murine high fat diet model.

Figure 44:
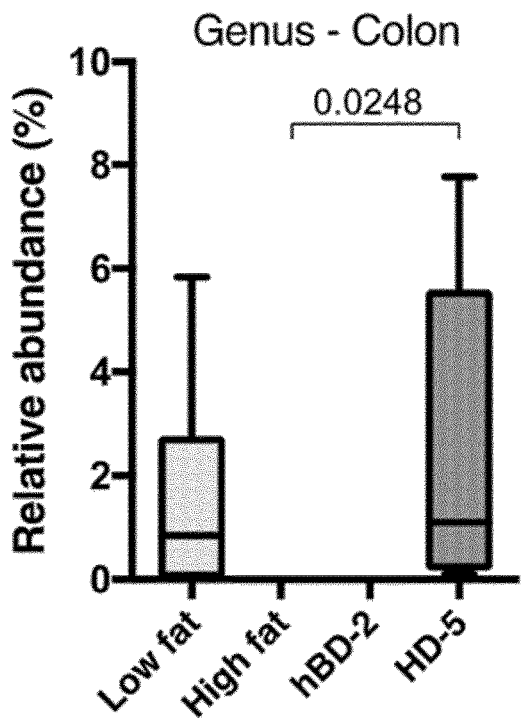

FIG. 44. Relative abundance of Alloprevotella in colon following therapeutic intervention with oral HD5 and hBD2 in a murine high fat diet model.

Figure 45:
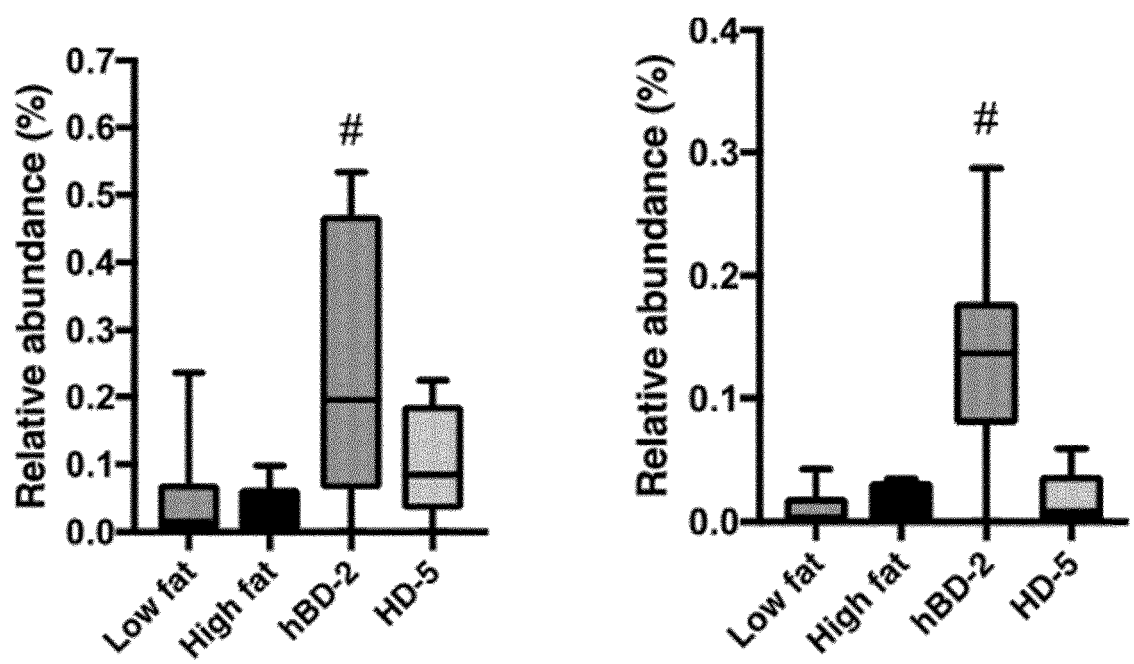

FIG. 45. Relative abundance of Bifidobacteriaceae in the small intestine (left panel) and colon (right panel) following therapeutic intervention with HD5 or hBD2 in a murine high fat diet model.

DETAILED DESCRIPTION

Definitions

Defensin: The term "defensin" as used herein refers to polypeptides belonging to the defensin class of antimicrobial peptides. Defensins represent one of the dominant innate host defences that serve to maintain a healthy microbiome and ward off potential pathogens (Wehkamp et al. et al., 2002 and Salzman et al., 2007). Defensins are peptides possessing antimicrobial activity against Gram positive and negative bacteria, fungi and archaea as well as exerting anti-inflammatory activity.

Human defensins are small cationic peptides divided into α- and β-defensins based on the topology of their three intramolecular cysteine disulphide bonds. α-defensins can be further subdivided into those expressed in neutrophil granules (HNP1-4) and those expressed by Paneth cells in the crypts of the small intestine (HD5 and HD6 or DEFA5 and DEFA6). β-defensins (DEFBn) are mainly produced by epithelial cells in various tissues and organs including the skin, eye, middle ear, mouth, trachea, lungs, gastrointestinal tract, urogenital system, kidneys, vagina, liver, pancreas and mammary glands. Examples of defensins include human intestinal alpha defensin 5 (HD5; SEQ ID NO: 5); human intestinal alpha defensin 6 (HD6; SEQ ID NO: 6); human neutrophil peptide 1 (HNP-1); human neutrophil peptide 2 (HNP-2); human neutrophil peptide 3 (HNP-3), all belonging to the alfa defensin class; and also human beta defensin 1 (hBD1; SEQ ID NO: 1); human beta defensin 2 (hBD2; SEQ ID NO: 2); human beta defensin 3 (hBD3; SEQ ID NO: 3); human beta defensin 4 (hBD4; SEQ ID NO: 4); and truncated human beta defensin 2 (SEQ ID NO:7). WO 2013/026794 documents that truncated hBD2 and non-truncated hBD2 have the same bioactivity.

Defensins are expressed as precursors and are processed by cleavage of the signal peptide and in some cases pro-peptides as well before secretion into the extracellular space. The best characterized members of the human β-defensin family are hBD1-4. Some of the human defensins e.g. hBD-1 are produced constitutively, whereas others e.g. hBD-2, hBD-3 and hBD-4 are induced by pro-inflammatory cytokines or exogenous microbial products. The above-identified sequences represent the predicted mature bioactive defensins. It will be understood by one of skill in the art that processing may differ from cell to cell and that the resulting secreted mature peptide may differ by one or two C- or N-terminal amino acids from the predicted sequences and still retain bioactivity.

Identity: The relatedness between two amino acid sequences or between two nucleotide sequences is described by the parameter "identity". The degree of identity between two amino acid sequences is determined using the Needleman-Wunsch algorithm (Needleman and Wunsch, 1970, J. Mol. Biol. 48: 443-453) as implemented in the Needle program of the EMBOSS package (Rice et al., 2000, http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows: (Identical Residues×100)/(Length of Alignment−Total Number of Gaps in Alignment).

Normal microbiota: The term "normal microbiota" is used herein to indicate a microbiota that is not dysbiotic. Normal microbiota is characterized by having large gene richness. Normal intestinal microbiota is characterized by comprising bacteria belonging to the genera *Bacteroidetes, Faecalibacterium, Roseburia, Blautia, Ruminococcus, Coprococcus, Bifidobacterium, Methanobrevibacter, Lactobacillus, Coprococcus, Clostridium, Akkermansia, Eubacterium*.

Normal lung microbiota is characterized by comprising bacteria belonging to the genera *Bacteroidetes, Firmicutes*, and Proteobacteria with the core microbiota consisting of

*Pseudomonas, Streptococcus, Prevotella, Fusobacteria, Veillonella, Haemophilus, Neisseria* and *Porphyromonas*

Treatment: The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering, reducing the active compounds to prevent or reduce the risk of the onset of symptoms or complications. The patient to be treated is preferably a mammalian, in particular a human being. The patients to be treated can be of various ages.

Patient: A patient is a subject, which has been diagnosed with a particular disorder such as an inflammatory disorder of the lungs or suffers from particular symptoms indicative of a disorder, such as an inflammatory disorder of the lungs. Mammalian Alfa Defensins and Mammalian Beta Defensins This disclosure relates to uses of mammalian alfa and/or beta defensins, such as human beta defensins, more preferably Hominidae, inter alia in the treatment of asthma, mild intermittent asthma, mild persistent asthma, moderate persistent asthma, severe persistent asthma, eosinophilic asthma, neutrophilic asthma, steroid refractory asthma, status asthmaticus, bronchiectasis and COPD.

In an embodiment, the mammalian alfa and/or beta defensins have a degree of identity of at least 80%, preferably at least 85%, more preferably at least 90%, and most preferably at least 95% to any of the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7. In another embodiment, a defensin differs from one of the SEQ ID NO: 1-7 by less than 10, such as less than 8, for example less than 5, such as less than 4, for example less than 3, such as less than 2 amino acids.

In a preferred embodiment, the human alfa defensins consist of (alfa defensin 5 (SEQ ID NO: 5) and/or alfa defensin 6 (SEQ ID NO: 6). In a preferred embodiment, the mammalian beta defensins consist of human beta defensin 1 (SEQ ID NO: 1), human beta defensin 2 (SEQ ID NO: 2), human beta defensin 3 (SEQ ID NO: 3), human beta defensin 4 (SEQ ID NO: 4) or truncated human beta defensin 2 (SEQ ID NO:7).

In a preferred embodiment, a human alfa defensin has a degree of identity of at least 80%, preferably at least 85%, more preferably at least 90%, and most preferably at least 95% to the amino acid sequence of SEQ ID NO: 5. In a preferred embodiment, the human mammalian alfa defensins consist of alfa defensin 5 (SEQ ID NO: 5). In a preferred embodiment, the human beta defensin has a degree of identity of at least 80%, preferably at least 85%, more preferably at least 90%, and most preferably at least 95% to the amino acid sequence of SEQ ID NO: 2. In a preferred embodiment, the human beta defensins consists of human beta defensin 2 (SEQ ID NO: 2) or truncated human beta defensin 2 (SEQ ID NO:7).

In yet another embodiment, the mammalian alfa defensins comprise of human alfa defensins and/or mouse alfa defensins, and functionally equivalent variants thereof. Preferably, the mammalian alfa defensin consist of human alfa defensin 5, human alfa defensin 6 and functionally equivalent variants thereof. More preferably, the mammalian alfa defensins consist of human alfa defensin 5, and functionally equivalent variants or orthologues thereof.

In yet a further embodiment, the mammalian beta defensins consist of human beta defensins and/or mouse beta defensins, and functionally equivalent variants thereof. Preferably, the mammalian beta defensins consist of human beta defensin 1, human beta defensin 2, human beta defensin 3, human beta defensin 4, and functionally equivalent variants thereof. More preferably, the mammalian beta defensins consist of human beta defensin 2, and functionally equivalent variants or orthologues thereof. In one embodiment, the methods comprise administration of an effective amount of at least one mammalian α-defensin to a subject in need of such treatment.

A "functionally equivalent variant" of a mammalian (e.g. human) alfa or beta defensin is a modified mammalian (e.g. human) alfa or beta defensin exhibiting approximatively the same effect on microbiota in the lung or the intestine as the parent mammalian (e.g. human) alfa and/or beta defensins. A functionally equivalent variant of a mammalian (e.g. human) defensin may comprise 1-5 amino acid modifications, preferably 1-4 amino acid modifications, more preferably 1-3 amino acid modifications, most preferably 1-2 amino acid modification(s), and in particular one amino acid modification, as compared to the mammalian (e.g. human) defensin amino acid sequence (e.g. any of SEQ ID NO 1-7). Preferably, for beta mammalian defensins, compared to human beta defensin 2, having SEQ ID NO 2 or truncated human beta defensin 2 (SEQ ID NO:7), and for alpha defensins compared to HD5 (SEQ ID NO 5). The term "modification" means herein any chemical modification of a mammalian (e.g. human) defensin. The modification(s) can be substitution(s), deletion(s) and/or insertions(s) of the amino acid(s) as well as replacement(s) of amino acid side chain(s); or use of unnatural amino acids with similar characteristics in the amino acid sequence. In particular the modification(s) can be amidations, such as amidation of the C-terminus. Preferably, amino acid modifications are of a minor nature, that is conservative amino acid substitutions or insertions that do not significantly affect the folding and/or activity of the polypeptide; single deletions; small amino- or carboxyl-terminal extensions; or a small extension that facilitates purification by changing net charge or another function, such as a poly-histidine tag, an antigenic epitope or a binding domain. In one embodiment the small extension, such as a poly-histidine tag, an antigenic epitope or a binding domain is attached to the mammalian (e.g. human) alfa or beta defensin through a small linker peptide of up to about 20-25 residues and said linker may contain a restriction enzyme cleavage site.

The Clustal W alignments in FIG. 3 can be used to predict which amino acid residues can be substituted without substantially affecting the biological activity of the protein. The sequences were aligned using Clustal W 2.1 (http://www.geno,me.jp/tools/clustalw/) and the following settings: Gap Open Penalty:10, Gap Extension Penalty: 0.05, Weight Transition: NO, Hydrophilic Residues for Proteins: GPSNDQE, Hydrophilic Gaps: YES, Weight Matrix: BLOSUM (for PROTEIN). Substitutions within the following group (Clustal W, 'strong' conservation group) are to be regarded as conservative substitutions:

S,T,A; N,E,Q,K; N,H,Q,K; N,D,E,Q; Q,H,R,K; M,I,L,V; M,I,L,F; H,Y; F,Y,W. Substitutions within the following group (Clustal W, 'weak' conservation group) are to be regarded as semi-conservative substitutions: —C,S, A; A,T,V; S,A,G; S,T,N,K; S,T,P,A; S,G,N,D; S,N,D,E,Q,K; N,D,E,Q,H,K; N,E,Q,H,R,K; V,L,I,M; H,F,Y.

Examples of conservative substitutions are substitutions made within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill (1979). The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in a mammalian alfa and/or beta defensin can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., activity against an airway hyper responsiveness or suppression cytokines e.g. TNF-alpha activity) to identify amino acid residues that are critical to the activity of the molecule. See also, Hilton et al., 1996, *J. Biol. Chem.* 271: 4699-4708. The identities of essential amino acids can also be inferred from analysis of identities with polypeptides which are related to mammalian alfa and/or beta defensins (see Clustal W alignment in FIG. 3).

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, Gene 46:145; Ner et al., 1988, *DNA* 7:127). When the result of a given substitution cannot be predicted with certainty, the derivatives may be readily assayed according to the methods described herein above to determine the presence or absence of biological activity.

Long-Acting Defensins

The half-life of an α- or β-defensin may be extended by fusing or conjugating the α- or β-defensin with another moiety or molecule i.e. constructing a long acting biologically active α- or β-defensin linked to a pharmaceutically acceptable molecule providing an in vivo plasma half-life of the α- or β-defensin, which is increased substantially compared to the in vivo plasma half-life of the un-conjugated α- or β-defensin administered in the same manner as the conjugated α- or β-defensin.

A long acting biologically active α- or β-defensin comprising a mammal α-defensin or analog thereof or a mammal β-defensin or analog thereof linked to a pharmaceutically acceptable molecule selected from a molecule having binding to neonatal Fc receptor (FcRn), transferrin, albumin (HAS), XTEN® or PEG, a homo-amino acid polymer (HAP), a proline-alanine-serine polymer (PAS), or an elastin-like peptide (ELP), hyaluronic acid, a negatively charged highly siasylated peptide such as the carboxy-terminal peptide (CTP) of chorionic gonadotropin (CG) β-chain, human IgG, and $CH_3(CH_2)_nCO-$ wherein n is 8 to 22.

The α- or β-defensin analogue may also be of non-mammalian origin, and may be selected from small organic molecules, peptides, polypeptides and proteins.

The α- or β-defensin agonist may be linked to the pharmaceutically acceptable molecule in various ways as described in the prior art literature, such as without limitation chemical coupling through a bifunctional linker, gene technologically by coupling the N-terminal or C-terminal of the defensin, such as α-defensin or β-defensin, to the pharmaceutically acceptable molecule, such as albumin or albumin analog. In particular, the N-terminal of albumin or an albumin analogue, e.g. human albumin, can be coupled to the C-terminal of an α-defensin or β-defensin, or the N-terminal of an α- or β-defensin; or the C-terminal of albumin, e.g. human albumin, can be coupled to the C-terminal of an α-defensin or β-defensin, or the N-terminal of α- or β-defensin. A linker sequence can be inserted between the albumin and the α- or β-defensin chain. The α- or β-defensin agonist may be linked to the pharmaceutically acceptable molecule through a stable linker or a more labile linker. Several linkers are known in the art, including bifunctional PEG molecules (e.g. see Paige et. al Pharmaceutical Research, vol. 12, no. 12, 1995), hydrolysable linkers (Shechter et al. Bioconjugate Chem. 2005, 16: 913-920 and International Journal of Peptide Research and Therapeutics, Vol. 13, Nos. 1-2, June 2007 and WO2009095479), PDPH and EMCH see e.g. in WO2010092135. In the special case where chemical conjugation (linking of two or more molecules) of the α- or β-defensin agonist, to the pharmaceutically acceptable molecule, strongly reduce the functional α- or β-defensin activity, it may be preferable to use a more labile linker that can release the functional α- or β-defensin agonist.

Half-life extension may also be accomplished through acylation of the peptide backbone with a spacer e.g. γ-L-glutamyl spacer and a C-18 fatty di-acid chain to Lysine. The fatty di-acid site chain and the spacer mediate a strong but reversible binding to albumin, slowing release from the injection site and reducing renal clearance.

Methods and Uses

Human beta defensin 2 is found to be able to reduce airway hyper responsiveness; increase pulmonary compliance; reduce lung inflammation; reduce BALF neutrophil-, eosinophil- and macrophage count as well as rebalance the immune system with normalization of IFN-γ, TNF-α, IL-4, IL-5, IL-6, IL-8, IL-9, IL-10 and IL-13 concentrations preventing a cytokine storm; thus showing potent activity as a medicament for prevention or treatment of inflammatory conditions of the lungs, such as asthma and COPD.

Surprisingly it has been found that parenteral and oral administration of defensins is effective to treat inflammatory conditions of the lung. This is unexpected, as it is known that hBD2 is not absorbed from the gut, as demonstrated in example 3 of the current disclosure. An advantage of this observation is that patients with compromised breathing capacity can take their defensin medicament orally. It is also expected that severely ill patients such as patients in medical ventilators and status asthmaticus patients can be treated by parenteral administration of at least one defensin.

Therefore in one aspect the disclosure relates to methods for treatment of an inflammatory lung condition by parenteral or oral administration of at least one defensin. Preferably the administration is oral. Oral and parenteral administration is advantageous for patients with compromised breathing or patients undergoing medical ventilation.

In another aspect there is provided methods for treatment of mild intermittent asthma, mild persistent asthma, moderate persistent asthma, severe persistent asthma, eosinophilic asthma, neutrophilic asthma, steroid refractory asthma, status asthmaticus, pneumonia, bronchiectasis, COPD, sarcoidosis, lung fibrosis or lung cancer by administering an effective amount of a mammalian defensin to a subject in need of such treatment. These conditions can be treated by intrapulmonary administration, oral, or parenteral administration. Preferably, the administration is intrapulmonary or oral.

The provided methods can treat or prevent lung inflammation by reducing migration of white blood cells e.g. neutrophils, eosinophils and macrophages in BALF.

Administration of hBD2 has proven to be effective in reducing in particular neutrophils and macrophages in BALF.

The methods may also rebalance the immune system, normalizing cytokine production of e.g. IFN-γ, TNF-α, IL-4, IL-5, IL-6, IL-8, IL-9, IL-10, and IL-13 in lung tissue homogenate thus preventing or treating a cytokine storm in a subject affected by one of the said conditions as described herein. Preferably, the method of treatment results in reduced cytokine production wherein the cytokine is IFN-γ, TNF-α, IL-4, IL-5, IL-6, IL-9, IL-10, or IL-13. In particular the methods may reduce the amount of IFN-γ, TNF-α, IL-4, IL-5, IL-9 and IL-13. The amount of cytokines can be determined in a lung biopsy or in BALF.

Further the methods may reduce airway hyperresponsiveness and increase pulmonary compliance in a subject affected by one of the said conditions as described herein. The provided methods can treat or prevent lung inflammation by changing bacterial phenotypes through a change at the transcriptional level as well as structure and composition of the lung bacterial flora or the lung metabolome of a subject affected by one of the said conditions as described herein.

Without being bound by theory the effects observed using oral administration may be ascribed to a change in the gut microflora and gut metabolome that may have an effect on the lungs through the so-called gut-lung axis.

Chronic lung disorders such as asthma, COPD and cystic fibrosis all exhibit a component of intestinal disease manifestation indicating that there is a vital cross talk between these two mucosal sites of the human body and a variety of respiratory diseases have been associated with a dysbiosis not only of the airway microbiota but also the intestinal microbiota (Marsland et al, 2015). Caesarian birth reduces the diversity and alters the composition of the intestinal microbiota early in life and is at the same time linked to a predisposition toward asthma during childhood (Jakobsson et al, 2014). Early life exposure to environmental microorganisms has been found to be protective against asthma (Ege et al, 2011) whereas early life as well as prenatal antibiotic exposure increases the risk of allergic asthma (Marra et al 2009). The inverse relationship between childhood infections and the development of asthma and allergies has been recognized for years, giving rise to the "hygiene hypothesis"; that a decrease in infectious exposures early in life results in deranged tolerance and increased autoimmune pathology (Wills-Karp et al, 2001). A complementary hypothesis is that perturbations in gastrointestinal microbiota composition due to antibiotic use and poor diet (low fiber, high sugar) in westernized areas have disrupted gastrointestinal microbiome-mediated mechanisms of mucosal tolerance.

Commensal microbes calibrate innate and adaptive immune responses and impact activation thresholds for pathogenic stimulations, in large part by producing small molecules that mediate host-microbial interactions (Donia and Fishback, 2015). While the epithelial barrier ensures that microorganisms are largely confined to the gut, microbial metabolites can penetrate the epithelial barrier, allowing them to enter and accumulate in the host circulatory system where they are sensed by immune cells (Dorrestein et al, 2014). Trompette et al 2013 demonstrated in mice that fermentable fibers in the diet changed the composition not only of the gut but also the lung microbiota in particular the ratio of Firmicutes to Bacteroidetes, the latter leading to increased local and systemic levels of Short Chain Fatty Acids, which in turn influenced Dendritic Cell hematopoiesis and functionality thus shaping the immunological environment in the lung and influencing the severity of allergic inflammation. Schirmer et al further demonstrated in the Human Functional Genomics Project that inter-individual variation in cytokine response is linked to specific microbial organisms as well as microbial functions. The majority of detected associations were both cytokine and stimulus specific, suggesting that the immune system recognizes and interacts with microbial organisms and products with high specificity and that these microbial factors are associated with a particular immunological phenotype. TNF-α and IFN-γ production capacity appeared to be more strongly influenced by the microbiome, whereas other cytokines such as IL-1β, IL-6 and Th17 derived IL-17 and IL-22 exhibited fewer, but more specific, associations with the gut microbiota.

A further aspect provides methods for prevention or treatment of mild intermittent asthma, mild persistent asthma, moderate persistent asthma, severe persistent asthma, eosinophilic asthma, neutrophilic asthma, steroid refractory asthma, status asthmaticus, pneumonia, bronchiectasis, COPD or lung cancer by administering an effective amount of an α- and/or β-defensin orally and/or a β-defensin to a subject in need of such treatment. In a preferred embodiment the asthma is steroid refractory asthma. In one embodiment, the administration is oral, buccal, sublingual, rectal, vaginal, intratracheal, intrapulmonary, intranasal, intracranial, subcutaneous, intravenous, dermal or transdermal. Preferably the administration is oral or intrapulmonary. Oral administration may be advantageous for patients with compromised breathing or undergoing medical ventilation.

Further provided are methods for treatment of asthma, mild intermittent asthma, mild persistent asthma, moderate persistent asthma, severe persistent asthma, eosinophilic asthma, neutrophilic asthma, steroid refractory asthma, status asthmaticus, bronchiectasis and COPD by administering an effective amount of an α- and/or a β-defensin parenterally, such as subcutaneously or intravenously to a subject in need of such treatment.

The methods of treatment described herein can be treated by administration of a composition comprising at least one mammalian α- and/or β-defensin in combination with either glucocorticoids, β-agonists, leukotriene receptor antagonists, theophylline, antibiotics, rifaximin, chemo- or immunotherapy, immunosuppressants, prebiotics, probiotics, tryphophane, short chain fatty acids, HNP-1, HNP-2, HNP-3, HNP-4, cathelicidin, lactoferin, lactoferricin, lysozyme, faecal transplants or a combination of these. The defensins described herein can be used to alleviate one or more symptoms of antibiotics, chemotherapy, radiation therapy, immunotherapy, or immunosuppressive therapy. The defensins can be administered separately or together with one or more of these therapies. The defensins can also be administered together with other medicaments which can be used to treat asthma.

Importantly, the disclosed methods can be used for treatment, prevention or normalization of a dysbiotic microbiota/metabolome in the lung of a subject that has undertaken and/or is undertaking an antibiotic treatment or chemotherapy or immunotherapy or immunosuppressive therapy or radiation therapy, or another treatment that has negative effects on the lung or intestinal microbiota.

Normalizing the lung microbiota may include stimulating the population of lung bacteria belonging to the genera Bacteroidetes, Firmicutes, and Proteobacteria with the core microbiota consisting of *Pseudomonas, Streptococcus, Prevotella, Fusobacteria, Veillonella, Haemophilus, Neisseria* and *Porphyromonas*.

Normalizing the lung microbiota may also involve changing the metabolome to one that produces relatively more tryptophane and/or butyrate and relatively less acetate.

The subject to be treated may have asthmatic symptoms <2 times per week, such as daily symptoms, such as continuous symptoms.

The subject to be treated may have asthmatic attacks of varying intensity, such as attacks affecting activity, such as attacks limiting physical activity, and/or asthmatic symptoms at night >2 times per month, such as >2 times a week that may last for days, such as frequent night time symptoms.

In one embodiment the subject to be treated has a forced expiratory volume at 1 second (FEV1)<80%, such as a FEV1 of 60-80%, such as a FEV1<60% of the predicted value.

Furthermore, the subject may have a peak expiratory flow rate PEFR with a variability of >20%, such as PEFR variability of 20-30%, such as a PEFR variability >30%, such as a PEFR variability >60%.

The subject in need of the treatment provided by the disclosed methods may present one or more of the following symptoms before treatment:

Mild Intermittent:
Symptoms <2 times a week
Asymptomatic and normal peak flow rate (PEFR) between attacks
Attacks are brief with varying intensity
Night time symptoms <2 times a month
Forced expiratory flow at 1 second (FEV1) or PEFR >80% of prediction
PEFR variability<20%

Mild persistent:
Symptoms >2 times a week, but <1 time a day
Exacerbations may affect activity
Night time symptoms >2 times a month
FEV1>80% of predicted
PEFR variability between 20% and 30%

Moderate persistent:
Daily symptoms
Use of short-acting beta agonists daily
Attacks affect activity
Exacerbations >2 times a week and may last for days
Night-time symptoms >1 time a week
FEV1 greater than 60% but less than 80% of predicted
PEFR variability>30%

Severe persistent:
Continual symptoms
Limited physical activity
Frequent exacerbations
Frequent night-time symptoms
FEV1<60% of predicted
PEFR variability>60%

In one embodiment, the treatment results in an improvement of at least one symptom so that a treated subject changes from severe persistent to moderate persistent, mild persistent, or mild intermittent. The treatment may result in an improvement of symptoms to that a treated subject changes from moderate persistent, to mild persistent, or mild intermittent, or from mild persistent to mild intermittent.

In other embodiments, defensins are used to treat inflammation of the lungs in connection with lung cancer. The lung cancer may be a small cell lung cancer or a non-small cell lung cancer (NSCLC). The NSCLC can be selected from adenocarcinoma, squamous-cell carcinoma, large-cell carcinoma, and bronchioloalveolar carcinoma. It is expected that administration of one or more defensins to a lung cancer patient can ameliorate one or more inflammatory symptoms of the disease or one or more side-effects of cancer therapy. The side effects of cancer therapy can be a side effect of radiation, chemotherapy, immunotherapy, or surgery. By improving the host defense of the lungs it is also expected that administration of at least one α- and/or β-defensin may reduce growth of tumor cells.

In Vitro Synthesis

Mammalian alfa defensins and mammalian beta defensins may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like. Chemical linking may be provided to various peptides or proteins comprising convenient functionalities for bonding, such as amino groups for amide or substituted amine formation, e.g. reductive amination, thiol groups for thioether or disulphide formation, carboxyl groups for amide formation, and the like. If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Mammalian alfa defensins and mammalian beta defensins, or functional equivalents thereof, may also be isolated and purified in accordance with conventional methods of recombinant synthesis. Recombinant synthesis may be performed using appropriate expression vectors and a eukaryotic or prokaryotic expression system. A solution may be prepared of the expression host and the media and the defensins present purified using HPLC, exclusion chromatography, gel electrophoresis, affinity chromatography, or other purification technique. Methods for recombinant expression of human beta defensin-2 in *E. coli* are disclosed in WO 2010/007166 (Novozymes).

The mammalian alfa and beta defensins may also be induced by administration of the corresponding mRNA.

Dosages

A mammalian alfa defensin and a mammalian beta defensin, such as a human alfa defensin and a human beta defensin, are preferably employed in pharmaceutical compositions in an amount which is effective to treat lung inflammation in general or for treatment of mild intermittent asthma, mild persistent asthma, moderate persistent asthma, severe persistent asthma, eosinophilic asthma, neutrophilic asthma, steroid refractory asthma, status asthmaticus, bronchiectasis, COPD or lung cancer preferably with acceptable toxicity to the patient. A mammalian alfa defensin and a mammalian beta defensin, such as a human alfa defensin and a human beta defensin, are also preferably employed in pharmaceutical compositions in an amount which is effective to maintain a normal microbiota composition in the lung and/or the intestine or to treat or normalize a dysbiotic microbiota in the lung and/or the intestine, preferably with acceptable toxicity to the patient in need of the treatment.

For such treatments, the appropriate dosage will, of course, vary depending upon, for example, the chemical nature and the pharmacokinetic data of a compound used, the individual host, the mode of administration and the nature and severity of the conditions being treated.

However, in general, for satisfactory results in mammals, for example humans, an indicated daily dosage of a human alfa defensin is preferably from about 0.1 mg HD5/kg body weight to about 10 mg HD5/kg body weight, more preferably from about 0.5 mg HD5/kg body weight to about 10 mg HD5/kg body weight; such as 1 mg HD5/kg body weight to 10 mg HD5/kg body weight, more preferably from about 1.2 mg HD5/kg body weight to about 10 mg HD5/kg body weight, preferably from about 1.2 mg HD5/kg body weight to about 5 mg HD5/kg body weight, even more preferably 1.2 mg HD5/kg body weight, for example, administered in divided doses up to one, two or three times a day.

In one embodiment an indicated daily dosage of a human beta defensin is preferably from about 0.1 mg hBD-2/kg body weight to about 10 mg hBD-2/kg body weight, more preferably from about 0.5 mg hBD-2/kg body weight to about 10 mg hBD-2/kg body weight; such as 1 mg hBD-2/kg body weight to 10 mg hBD-2/kg body weight, more preferably from about 1.2 mg hBD-2/kg body weight to about 10 mg hBD-2/kg body weight, preferably from about 1.2 mg hBD-2/kg body weight to about 5 mg hBD-2/kg body weight, even more preferably 1.2 mg hBD-2/kg body weight, for example, administered in divided doses up to one, two or three times a day.

When two different defensins are administered in one dosage, the dosage may comprise equal or approximately equal amounts of the two defensins determined on a weight basis or on a molar basis. The ratio may also differ so that the ratio of alpha defensin to beta-defensin varies from 10:1 to 1:10, such as 5:1 to 1:5, for example 2:1 to 1:2 determined on a weight or molar basis.

The compounds of preferred embodiments can be administered to mammals, for example humans, by similar modes of administration at similar dosages than conventionally used.

In one embodiment, methods are provided as described herein, wherein the daily dosage is between 0.1 and 10 mg defensin/kg, such as between 0.5 and 5 mg defensin/kg, such as between 1 and 2 mg defensin/kg, such as 1.2 mg defensin/kg per day.

In certain embodiments, the pharmaceutical compositions of preferred embodiments can include a mammalian alfa defensin and/or a mammalian beta defensin, such as a human alfa defensin and/or a human beta defensin, in an amount of about 0.5 mg or less to about 1500 mg or more per unit dosage form, preferably from about 0.5, 0.6, 0.7, 0.8, or 0.9 mg to about 150, 200, 250, 300, 350, 400, 450, 500, 600, 700, 800, 900, or 1000 mg, and more preferably from about 1, 2, 3, 4, 5, 6, 7, 8, 9, 10, 15, 20, or 25 mg to about 30, 35, 40, 45, 50, 55, 60, 65, 70, 75, 80, 85, 90, 95, or 100 mg. In certain embodiments, however, lower or higher dosages than those mentioned above may be preferred. Appropriate concentrations and dosages can be readily determined by one skilled in the art. In certain embodiments, the pharmaceutical compositions of preferred embodiments include a mammalian alfa defensin, such as a human alfa defensin. In other embodiments, the pharmaceutical compositions of preferred embodiments include a mammalian beta defensin, such as a human beta defensin. In further embodiments, the pharmaceutical compositions of preferred embodiments include a mammalian alfa defensin and a mammalian beta defensin, such as a human alfa defensin and a human beta defensin, wherein the alfa and the beta defensins are present in equal amounts on a molarity basis or on a mg/mL basis.

In one embodiment, the mammalian alfa and/or beta defensin is administered at least once daily, such as at least twice daily, for example at least 3 times daily or continuously.

In one embodiment, the mammalian alfa and/or beta defensin is administered intravenously by continuous infusion or intrapulmonary by continuous mechanical ventilation in a patient on an external ventilator.

Formulations for Oral or Parenteral Administration

Mammalian alfa and beta defensins can be employed therapeutically in compositions formulated for administration by any conventional route. In one embodiment, the administration of at least one mammalian β-defensin, according to the disclosed methods, is generally intranasal. Intranasal administration is normal for pulmonary drug delivery.

In one embodiment, the administration of at least one mammalian α-defensin and/or at least one mammalian β-defensin, according to the disclosed methods, is oral.

In one embodiment, the administration of at least one mammalian α-defensin and/or at least one mammalian β-defensin, according to the disclosed methods, is subcutaneous or intravenous.

Within some embodiments, compositions, of preferred embodiments may be formulated as a lyophilizate, utilizing appropriate excipients that provide stability as a lyophilizate, and subsequently after rehydration. Pharmaceutical compositions containing a mammalian alfa defensin and/or a mammalian beta defensin, such as a human alfa defensin and/or a human beta defensin, can be manufactured according to conventional methods, e.g., by mixing, granulating, coating, dissolving or lyophilizing processes. In a preferred embodiment, pharmaceutical compositions containing a mammalian alfa defensin and/or a mammalian beta defensin are formulated as a sterile and isotonic solution.

Pharmaceutically acceptable carriers and/or diluents are familiar to those skilled in the art. For compositions formulated as liquid solutions, acceptable carriers and/or diluents include saline and sterile water should be included, and the composition may optionally include antioxidants, buffers, bacteriostats, and other common additives.

The disclosed compound may be formulated in a wide variety of formulations for oral administration. Solid form preparations may include powders, tablets, drops, capsules, cachets, lozenges, and dispersible granules. Other forms suitable for oral administration may include liquid form preparations including emulsions, syrups, elixirs, aqueous solutions, aqueous suspensions, toothpaste, gel dentifrice, chewing gum, or solid form preparations which are intended to be converted shortly before use to liquid form preparations, such as solutions, suspensions, and emulsions.

The disclosed compound may be formulated in a wide variety of formulations for intranasal, subcutaneous or intravenous administration. The formulation can contain (in addition to a mammalian alfa defensin and/or a mammalian beta defensin, and other optional active ingredients) carriers, fillers, disintegrators, flow conditioners, sugars and sweeteners, fragrances, preservatives, stabilizers, wetting agents, emulsifiers, solubilizers, salts for regulating osmotic pressure, buffers, diluents, dispersing and surface-active agents, binders, lubricants, and/or other pharmaceutical excipients as are known in the art. One skilled in this art may further formulate mammalian alfa defensins and mammalian beta defensins in an appropriate manner, and in accordance with accepted practices, such as those described in Remington's Pharmaceutical Sciences, Gennaro (1990).

A mammalian alfa defensin and a mammalian beta defensin, such as a human alfa defensin and a human beta defensin, can be used alone, or in combination therapies with one, two, or more other pharmaceutical compounds or drug substances, for example with glucocorticoids, β-agonists, leukotriene receptor antagonists, theophylline, antibiotics, Chemo- or Immune therapy or a combination of these and/or with one or more pharmaceutically acceptable excipient(s).

Airway Administration

Airway administration may be used for administering the compositions of the disclosure. By intrapulmonary administration is meant topical administration to the lungs. When used herein the terms "intratracheal, intrabronchial or intra alveolar administration" include all forms of such administration whereby a defensin is applied into the trachea, the bronchi or the alveoli, respectively, whether by instillation of a solution of a defensin, by applying a defensin in a powder form, or by allowing a defensin to reach the relevant part of the airway by inhalation of a defensin as an aerosolized or nebulized solution or suspension or inhaled powder or gel, with or without added stabilizers or other excipients.

Methods of intrabronchial/alveolar administration include, but are not limited to, bronchoalveolar lavage (BAL) according to methods well known to those skilled in the art, using as a lavage fluid a physiologically acceptable composition in which a defensin has been dissolved or indeed by any other effective form of intrabronchial administration including the use of inhaled powders containing defensins in dry form, with or without excipients, or the direct application of a defensin, in solution or suspension or powder form during bronchoscopy. Methods for intratracheal administration include, but are not limited to, blind tracheal washing with a similar solution of dissolved defensins or a defensin suspension, or the inhalation of nebulized fluid droplets containing dissolved defensins or a defensin suspension obtained by use of any nebulizing apparatus adequate for this purpose.

In another embodiment, intratracheal, intrabronchial or intra alveolar administration does not include inhalation of the product but the instillation or application of a solution of a defensin or a powder or a gel containing defensin into the trachea or lower airways.

Other preferred methods of administration may include using the following devices:
1. Pressurized nebulizers using compressed air/oxygen mixture
2. Ultrasonic nebulizers
3. Electronic micropump nebulizers
4. Metered dose inhaler (MDI)
5. Dry powder inhaler systems (DPI), The aerosol may be delivered via a) facemasks or b) via endotracheal tubes in intubated patients during mechanical ventilation (device 1, 2 and 3). The devices 4 and 5 can also be used by the patient without assistance provided that the patient is able to self-activate the aerosol device.

Preferred concentrations for a solution comprising a defensin and/or functional homologues or variants of a defensin are in the range of from about 0.1 µg to 1000 µg per ml solution, such as in the range of from about 0.1 µg to 250 µg per ml solution.

Pharmaceutical Composition for Intrapulmonary Administration

Pharmaceutical compositions or formulations for use in the present disclosure include defensin in combination with, preferably dissolved in, a pharmaceutically acceptable carrier, preferably an aqueous carrier or diluent, or carried to the lower airways as a pegylated preparation or as a liposomal or nanoparticle preparation administered as an aerosol via inhalation, or as a lavage fluid administered via a bronchoscope as a bronchoalveolar lavage or as a blind intratracheal wash or lavage. A variety of aqueous carriers may be used, including, but not limited to 0.9% saline, buffered saline, physiologically compatible buffers and the like. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution prior to administration In one embodiment a freeze-dried defensin preparation may be pre-packaged for example in single dose units. In an even more preferred embodiment the single dose unit is adjusted to the patient.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

The formulations may contain pharmaceutically acceptable carriers and excipients including microspheres, liposomes, microcapsules, nanoparticles or the like. Conventional liposomes are typically composed of phospholipids (neutral or negatively charged) and/or cholesterol. The liposomes are vesicular structures based on lipid bilayers surrounding aqueous compartments. They can vary in their physiochemical properties such as size, lipid composition, surface charge and number and fluidity of the phospholipids bilayers. The most frequently used lipid for liposome formation are: 1,2-Dilauroyl-sn-Glycero-3-Phosphocholine (DLPC), 1,2-Dimyristoyl-sn-Glycero-3-Phosphocholine (DMPC), 1,2-Dipalmitoyl-sn-Glycero-3-Phosphocholine (DPPC), 1,2-Distearoyl-sn-Glycero-3-Phosphocholine (DSPC), 1,2-Dioleoyl-sn-Glycero-3-Phosphocholine (DOPC), 1,2-Dimyristoyl-sn-Glycero-3-Phosphoethanolamine (DMPE), 1,2-Dipalmitoyl-sn-Glycero-3-Phosphoethanolamine (DPPE), 1,2-Dioleoyl-sn-Glycero-3-Phosphoethanolamine (DOPE), 1,2-Dimyristoyl-sn-Glycero-3-Phosphate (Monosodium Salt) (DMPA), 1,2-Dipalmitoyl-sn-Glycero-3-Phosphate (Monosodium Salt) (DPPA), 1,2-Dioleoyl-sn-Glycero-3-Phosphate (Monosodium Salt) (DOPA), 1,2-Dimyristoyl-sn-Glycero-3-[Phospho-rac-(1-glycerol)] (Sodium Salt) (DMPG), 1,2-Dipalmitoyl-sn-Glycero-3-[Phospho-rac-(1-glycerol)] (Sodium Salt) (DPPG), 1,2-Dioleoyl-sn-Glycero-3-[Phospho-rac-(1-glycerol)] (Sodium Salt) (DOPG), 1,2-Dimyristoyl-sn-Glycero-3-[Phospho-L-Serine] (Sodium Salt) (DMPS), 1,2-Dipalmitoyl-sn-Glycero-3-[Phospho-L-Serine] (Sodium Salt) (DPPS), 1,2-Dioleoyl-sn-Glycero-3-[Phospho-L-Serine] (Sodium Salt) (DOPS), 1,2-Dioleoyl-sn-Glycero-3-Phosphoethanolamine-N-(glutaryl) (Sodium Salt) and 1,1',2,2'-Tetramyristoyl Cardiolipin (Ammonium Salt). Formulations composed of DPPC in combination with other lipids or modifiers of liposomes are preferred e.g. in combination with cholesterol and/or phosphatidylcholine.

Long-circulating liposomes are characterized by their ability to extravasate at body sites where the permeability of the vascular wall is increased. The most popular way of producing long-circulating liposomes is to attach hydrophilic polymer polyethylene glycol (PEG) covalently to the outer surface of the liposome. Some of the preferred lipids are: 1,2-Dipalmitoyl-sn-Glycero-3-Phosphoethanolamine-N-[Methoxy(Polyethylene glycol)-2000] (Ammonium Salt), 1,2-Dipalmitoyl-sn-Glycero-3-Phosphoethanolamine-N-[Methoxy(Polyethylene glycol)-5000] (Ammonium Salt), 1,2-Dioleoyl-3-Trimethylammonium-Propane (Chloride Salt) (DOTAP).

Possible lipids applicable for liposomes are supplied by Avanti, Polar Lipids, Inc, Alabaster, Ala. Additionally, the liposome suspension may include lipid-protective agents which protect lipids against free-radical and lipid-peroxidative damage on storage. Lipophilic free-radical quenchers, such as alpha-tocopherol and water-soluble iron-specific chelators, such as ferrioxianine, are preferred.

A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028, all of which are incorporated herein by reference. Another method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15-60 minute period with agitation. The size distribution of the resulting multilamellar vesicles can be shifted toward smaller sizes by hydrating the lipids under more vigorous agitation conditions or by adding solubilizing detergents such as deoxycholate.

Micelles are formed by surfactants (molecules that contain a hydrophobic portion and one or more ionic or otherwise strongly hydrophilic groups) in aqueous solution.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with IV injection such as, TWEEN-80, PLURONIC F-68, n-octyl-beta-D-glucopyranoside, and the like. In addition, phospholipids, such as those described for use in the production of liposomes, may also be used for micelle formation.

EXAMPLES

Example 1

Figure 1:
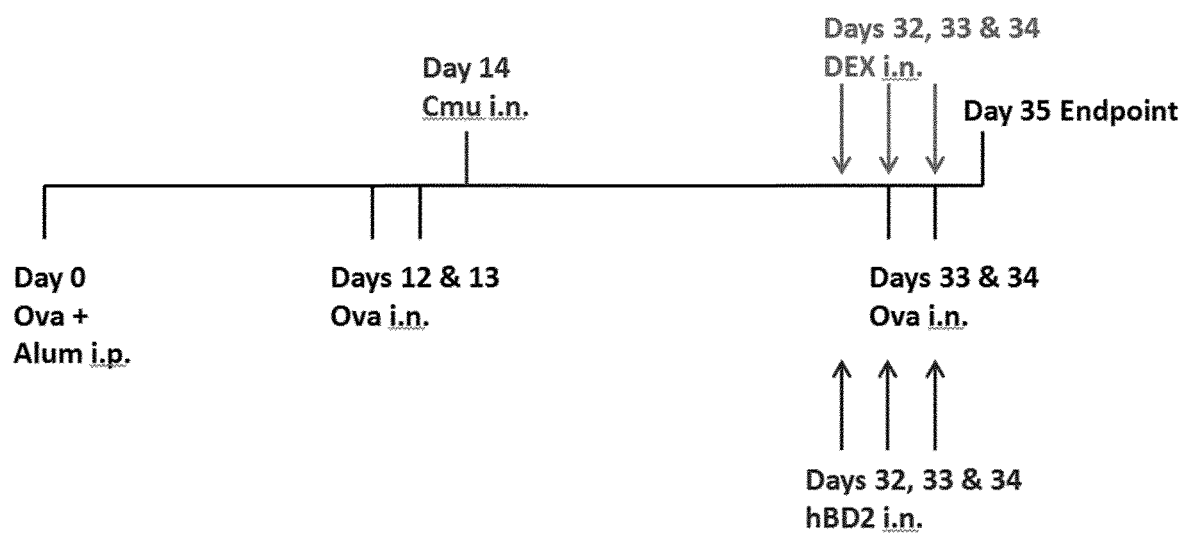
FIG. 1. Schematic outline of the experimental setup for investigating the effects of mammalian β-defensins in a murine steroid-insensitive model of asthma, where the mice are sensitized by Ovalbumin and infected with *C. muridarum* (Essilfie et al., 2015).

To determine and assess the efficacy of mammalian β-defensins in a murine, infection induced, severe, steroid-insensitive, neutrophilic, allergic airways disease model of asthma (FIG. 1).
Materials and Methods
Treatment Regimen:

Female 6-8 weeks old BALB/c mice were intraperitoneally (IP) sensitized to ovalbumin 50 µg with the adjuvant alum 1 mg in 200 µL 0.9% saline. Mice were intranasally (IN) challenged with Ova on day 12-13 and day 33-34 (10 µg in 50 µL sterile saline). On day 14, mice were inoculated IN with the natural mouse pathogen *Chlamydia muridarum* (Cmu: 100 inclusion forming units, ATCCVR-123, 30 µL sucrose phosphate glutamate buffer (SPG). Dexamethasone (DEX) was administered IN (2 mg/kg; 50 µL phosphate buffered saline (PBS)) on day 32-34 with Ova challenges. hBD-2 was administered IN (5 mg/kg; 50 µL phosphate buffered saline) on day 30, 32 and 34.

Drugs administered through intranasal delivery to mice are expected to reach the lungs via the airways and is an art-recognized model of intrapulmonary administration.
Test:

Airway inflammation: Differential leucocyte counts were obtained from May-Grunwald Giemsa stained BALF cells, using a light microscope.

Lung function: AHR was measured by anaesthetized, cannulated mice using the Scireq Flexivent FX1 system. Data are represented as airway resistance at 10 mg/kg methacholine and as dose responsive curves.
Results
Airway Inflammation:

The Ova sensitized and *C. muridarum* infected mice developed a highly statistically significant increase of total leucocytes, macrophages, lymphocytes, neutrophils and to a lesser extent eosinophils. The IN hBD-2 treated group showed a complete normalization of neutrophil count and to a lesser extent lymphocytes, whereas macrophages and eosinophils did not change. The IN hBD-2 plus DEX group showed complete normalization of eosinophils, but aside from this no additive effect was observed (FIG. 7).
Lung Function:

The Ova sensitized mice (Ova) had a greater AHR compared with Saline (Sal) (non-asthmatic) controls. The difference is statistically highly significant. The IN hBD-2 treated group (Cmu/Ova/hBD2) showed a completely normalized AHR on par with the Saline control group. The IN hBD-2 plus DEX group showed a completely normalized AHR on par with the Saline control group but DEX did not seem to have an additive effect (FIG. 4).

Conclusion: the example demonstrates that intranasally administered hBD2 can completely normalize airway hyperresponsiveness and neutrophil count in BALF in a known steroid-refractory animal model of asthma.

Example 2

To determine and assess the efficacy of IN versus Oral administered mammalian β-defensins in a murine house dust mite/Freunds complete adjuvant driven model of allergic asthma (FIG. 2).

Materials and Methods

Treatment Regime:

Female 7-10 weeks old BALB/c mice were randomly allocated into 7 study groups one day prior to study start and subcutaneously (SC) sensitized to house dust mite (100 μg HDM in 200 μL saline plus Freunds complete adjuvant in 0.9% saline). Mice were then intranasally (IN) challenged with HDM on day 14 (HDM 25 μg in 50 μL of saline). Dexamethasone was administered orally (1 mg/kg BID; 50 μL phosphate buffered saline (PBS)) on day 14. hBD-2 was administered IN or orally (1.7 mg/kg TID IN; 0.4 mg/kg TID IN; 0.4 mg/kg TID orally, 50 μL phosphate buffered saline) on day 14. The initial dose was administered 60 minutes prior to challenge, and the subsequent doses approximately 6 hours apart.

Tests:

Airway inflammation: At 48 hours post challenge, bronchoalveolar lavage was performed washing the lungs with 3 volumes of cold PBS (0.4; 0.3 and 0.3 mL, total 1 mL). Total and differential leucocyte cell counts were determined on an automated haematological analyser Sysmex XT-2000iV.

Lung function: Starting 48 hours after HDM challenge, measurements of lung resistance and lung compliance were carried out after methacholine challenge (3.125 MCH1; 6.25 MCH2; 12.5 MCH3 and 25 mg/mL MCH4) by anaesthetized, cannulated mice using DSI's Buxco Finepoint RC system. Data are represented as airway resistance at 10 mg/kg methacholine and as dose responsive curves.

Lung sampling for cytokine analysis: After completion of every BAL, lungs were removed from the thorax, snap frozen in liquid nitrogen and stored frozen at −80 degrees Celcius until analysis of cytokine concentration of IL-1β, TNF-α, IL-6, IL-10 and IFNγ by ELISA.

Results

An increase of lung resistance values and decrease of pulmonary compliance values in HDM-challenged vehicle treated animals in comparison to saline-challenged (non-asthmatic) mice was observed. An inflammatory response in both vehicle-treated groups of mice (oral and intranasal) was induced by a single HDM challenge 14 days post sensitization with HDM and adjuvant. It was characterized by a statistically significant increase in total cell, eosinophil, neutrophil, macrophage and lymphocyte counts in BALF ($p<0.05$) when compared to saline-challenged controls. Also, analysis of concentration of five cytokines IL-1β, TNF-α, IL-6, IL-10 and IFN-γ in lung tissue homogenates revealed significantly higher levels in HDM-challenged animals compared to saline-challenged controls.

Dexamethasone treatment significantly inhibited total cell and eosinophil counts but not neutrophil, macrophage and lymphocyte counts in BALF. In accordance with the cellular data, dexamethasone did not influence levels of IL-1β, TNF-α, IL-6, IL-10 and IFN-γ in lung tissue homogenates as compared to HDM/vehicle control. However, it influenced AHR measurements related to eosinophil counts. Obtained results indicate that this model is steroid resistant to a certain degree.

Figure 9:
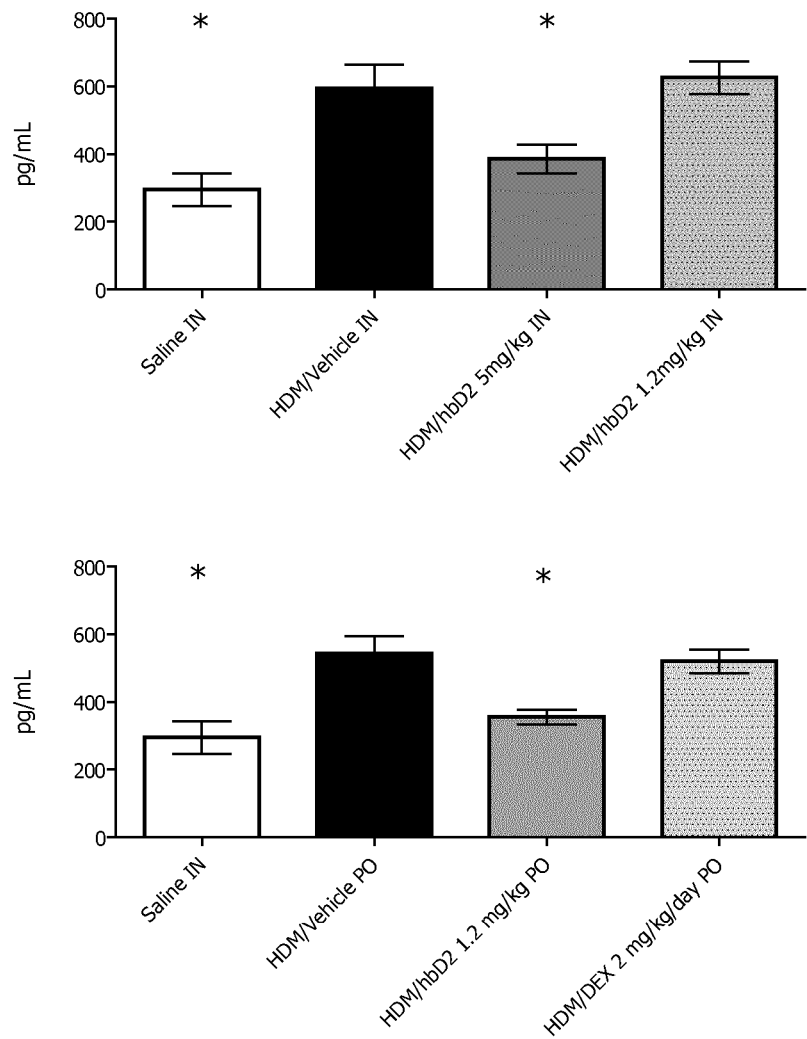
Figure 10:
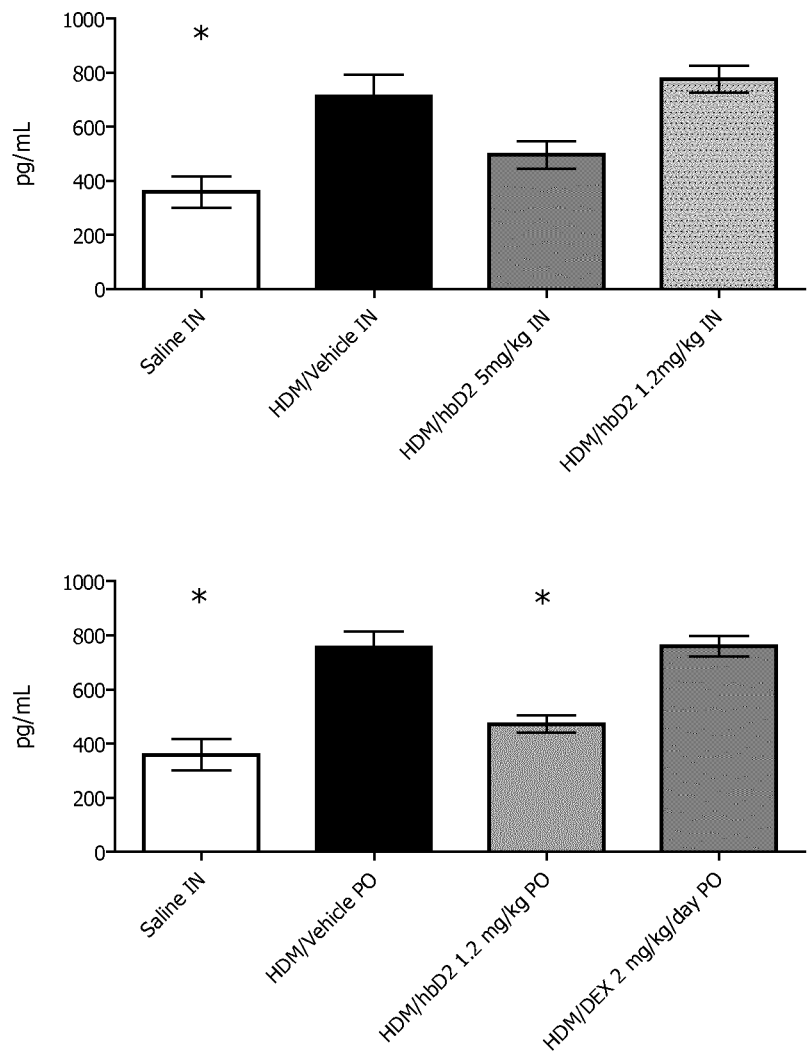
Figure 11:
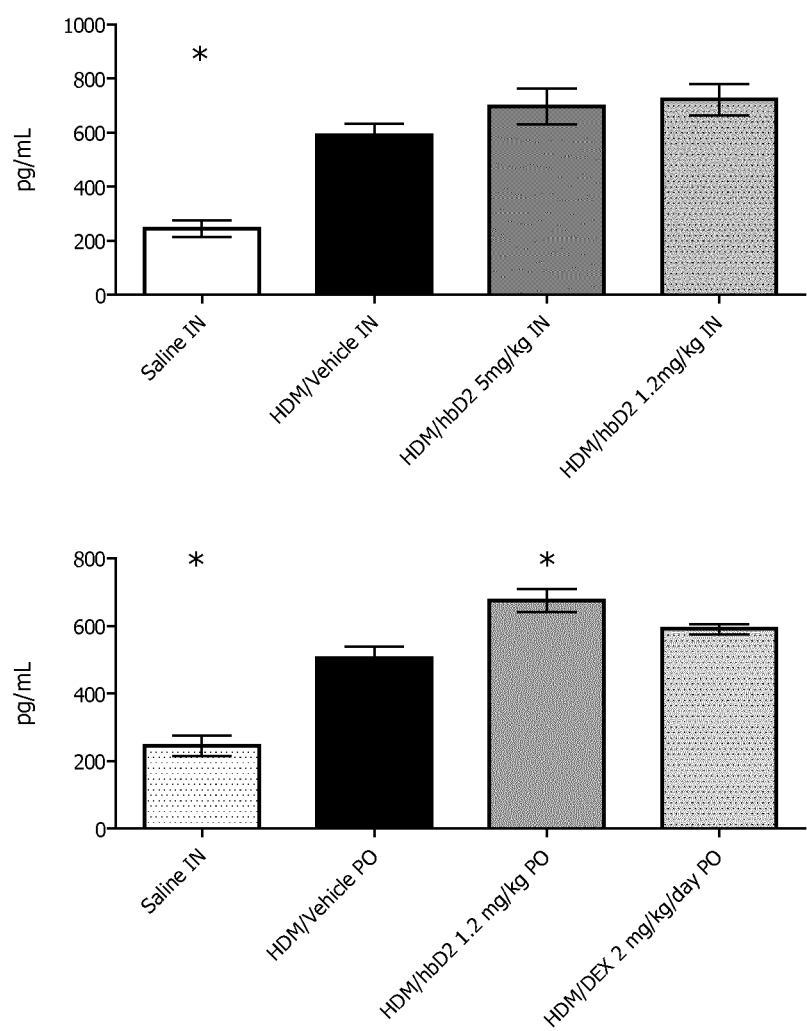

Test item hBD-2, both after oral and intranasal application TID, on day 14, effectively inhibited increase of airway resistance (FIGS. 5a and 5b) and decrease of pulmonary compliance (FIGS. 6a and 6b) as compared to HDM challenged vehicle treated animals. More prominent effect was observed on some measured parameters after intranasal application, such as cellular influx in BALF, where both doses (0.4 mg/kg/day TID and 1.7 mg/kg/day TID) significantly inhibited neutrophil counts, while the steroid standard dexamethasone failed to inhibit them. Similar significant effects were observed on IL-6, IL-10 and IFN-γ cytokine levels in lung tissue homogenates with both dosing routes (FIG. 9, 14, 17). Perorally administered hBD2 significantly reduced TNF-α (FIG. 10), while the intranasally administered hBD2 was not significantly different from the control. FIG. 11 shows the effect on IL-1β.

Conclusion: All obtained results indicate clear anti-inflammatory effects of hBD-2 in the house dust mite/Freunds complete adjuvant driven mouse model of allergic asthma.

Surprisingly, orally administered hBD2 was also effective in treating asthma and reducing inflammation in asthmatic mice.

Example 3

To determine and assess the efficacy of IN versus Oral mammalian β-defensins in a murine house dust mite/Freunds complete adjuvant driven model of allergic asthma (FIG. 2).

Materials and Methods

Treatment regime: Female 7-10 weeks old BALB/c mice randomly allocated into 4 study groups one day prior to study start were subcutaneously (SC) sensitized to house dust mite (100 μg HDM in 200 μL saline plus Freund's complete adjuvant in 0.9% saline). Mice were intranasally (IN) challenged with HDM on day 14 (HDM 25 μg in 50 μL of saline). hBD-2 was administered IN or orally (0.4 mg/kg TID IN; 0.4 mg/kg TID orally, 50 μL phosphate buffered saline) on day 14. The initial dose was administered 60 minutes prior to challenge, and the subsequent doses approximately 6 hours apart.

Tests:

Lung tissue sampling: Lungs were removed from the thorax, snap frozen in liquid nitrogen and stored frozen at −80 degrees Celsius until analysis of cytokine concentration of IL-4, IL-5, IL-8 (KC), IL-9 and IL-13 by ELISA.

Lungs were inflated in situ in 10% buffered formalin, removed from thorax, placed individually in 10% buffered formalin, paraffin embedded in toto, sectioned and H&E/PAS stained.

Blood Sampling

All terminal blood samples were collected via jugular vein bleeds. Blood was sampled to Li-heparin tubes, put on ice and immediately centrifuged at 4° C. Plasma was separated and stored at −80° C. until the potential SCFA analysis.

Lung Tissue Sampling

The lungs were exposed and excised by gently opening the thorax and by cutting down either side of the sternum and ribs and trimming back. Lungs from first 6 animals per group were removed from thorax, snap frozen in liquid nitrogen and stored frozen at −80° C. until analysis of cytokine concentration by ELISA.

Lungs from other 8 animals per group were inflated in situ with 10% buffered formalin, removed from thorax, placed individually in 10% buffered formalin, paraffin embedded in toto, sectioned and H&E/PAS stained. The paraffin blocks were retained for the IHC analysis.

Read-Outs

Histopathology (H&E; PAS) (N=8/group; total N=32)
Cytokines in lung tissue homogenates (IL-4, IL-5, KC, IL-9 and IL-13) (N=6/group; total N=24)

Histopathology

Cellular influx (mononuclears, eosinophils, neutrophils) was assessed semi-quantitatively on H&E stained slides separately for peri-bronchial/bronchiolar and perivascular space as follows:

| 0 | absent |
|---|---|
| 1 | few scattered inflammatory cells |
| 2 | larger aggregates |
| 3 | marked accumulation of cells |

Overall score for inflammation was calculated as sum of all individual scores.

Goblet cell metaplasia, separately at a level of large airways and distal airways, was assessed at PAS-stained slides as follows:

| 0 | no mucus containing cells along basement membrane |
|---|---|
| 1 | few positive cells along basement membrane with less than 75% of the cytoplasm stained |
| 2 | few positive cells along basement membrane with more than 75% of the cytoplasm stained |
| 3 | numerous positive cells along basement membrane with less than 75% of the cytoplasm stained |
| 4 | numerous positive cells along basement membrane with more than 75% of the cytoplasm stained |

Statistical Evaluation

Data was processed using MS Excel. Statistical analysis was performed using GraphPad Prism software (version 5.04). Differences between groups are considered statistically significant when $p<0.05$.

Statistical analysis of selected histological score-values data were performed using median and non-parametric Mann-Whitney test.

Results

An inflammatory response in both vehicle-treated groups of mice (oral and intranasal) was induced by a single HDM challenge 14 days post sensitization with HDM and adjuvant. It was characterized by a statistically significant increase in concentration of five cytokines IL-4, IL-5, IL-8, IL-9 and IL-13 in lung tissue homogenates and by severe histological inflammatory changes of lung tissue in HDM-challenged animals compared to saline-challenged controls.

Figure 12:
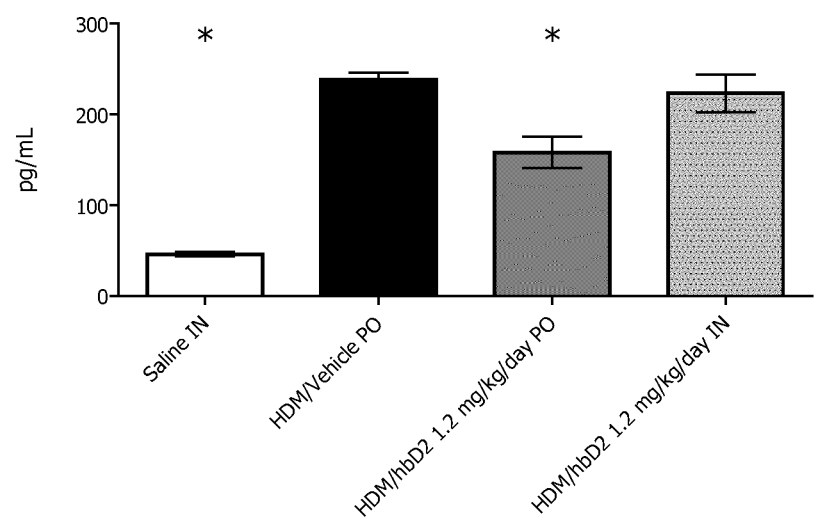
Figure 13:
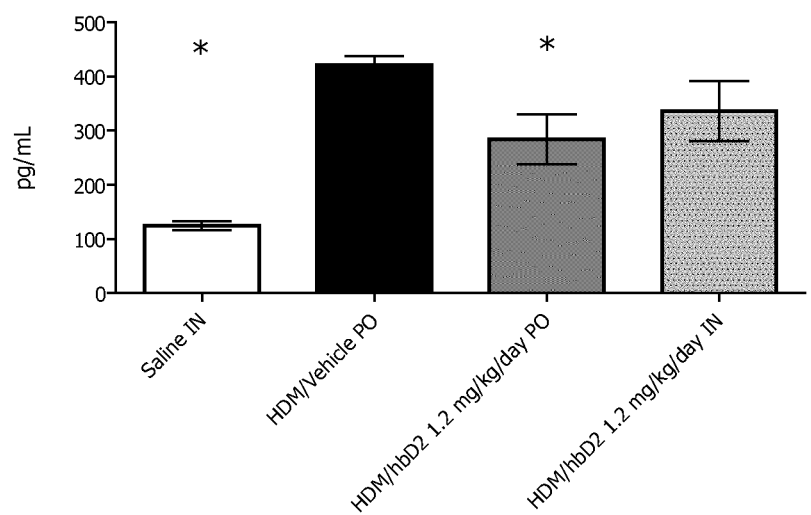
Figure 14:
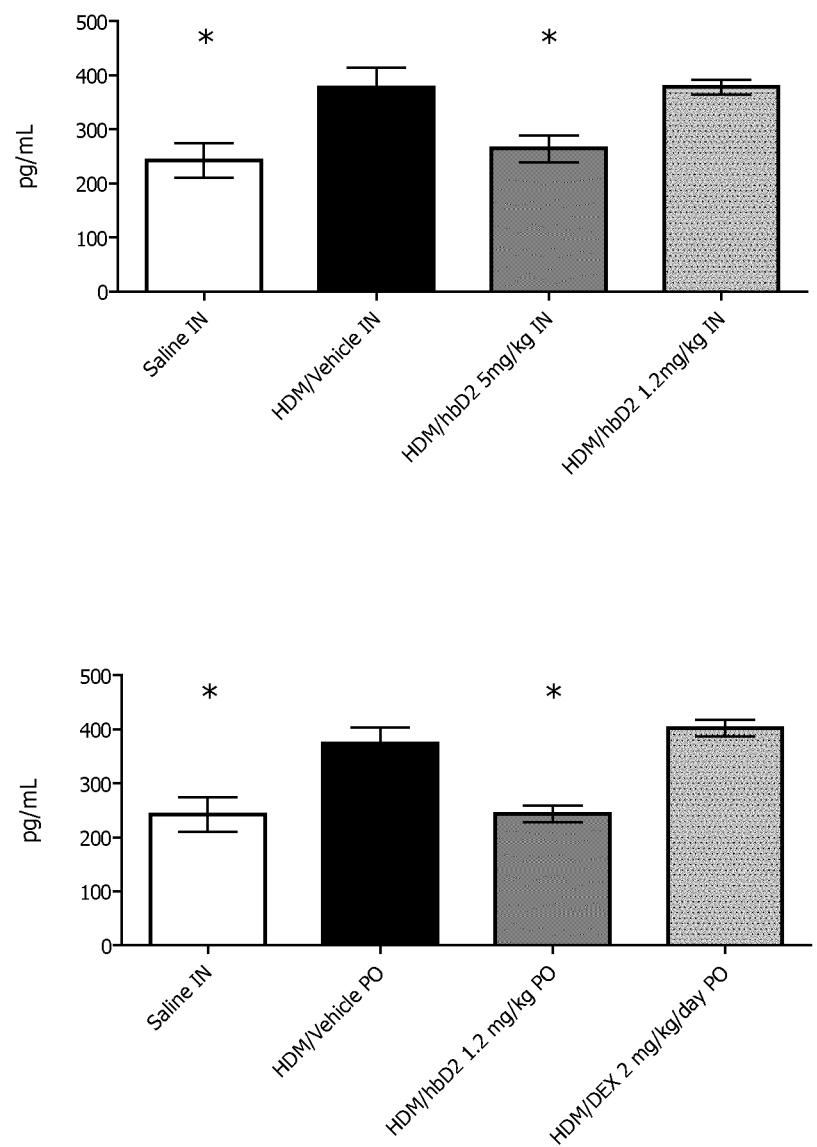
Figure 15:
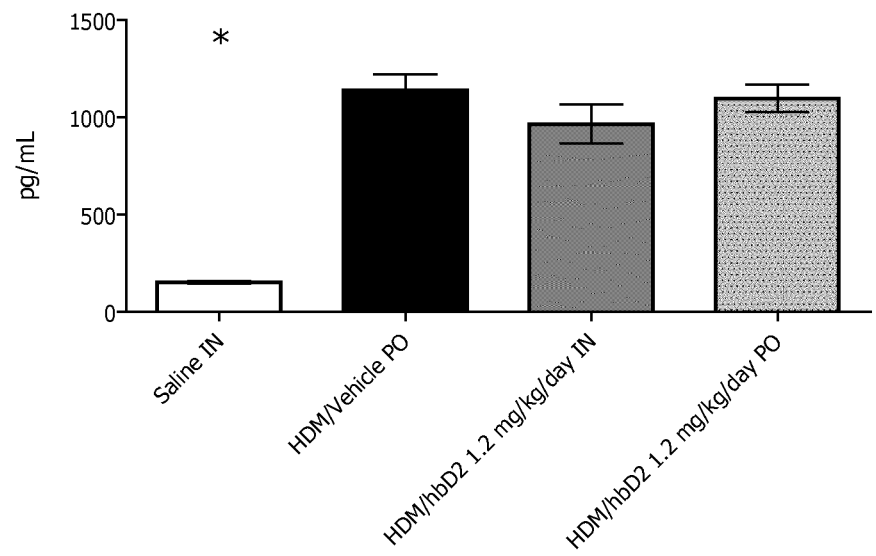
Figure 16:
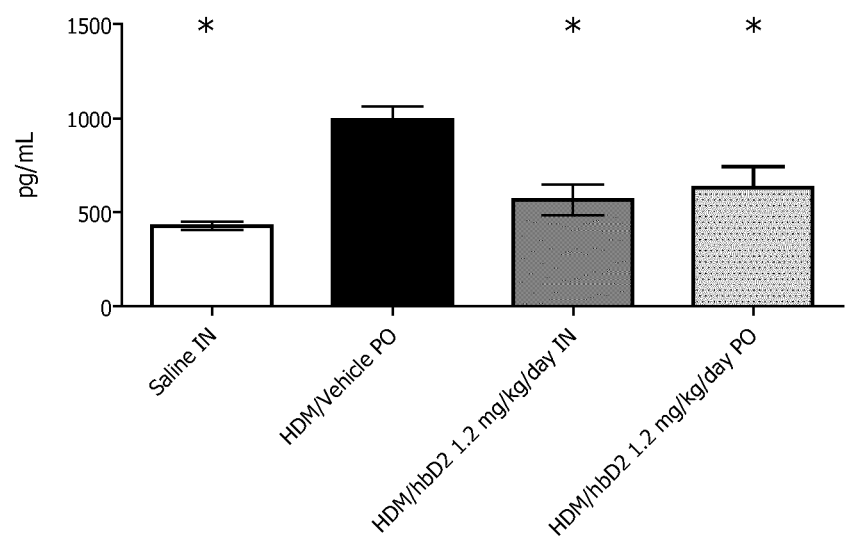
Figure 18:
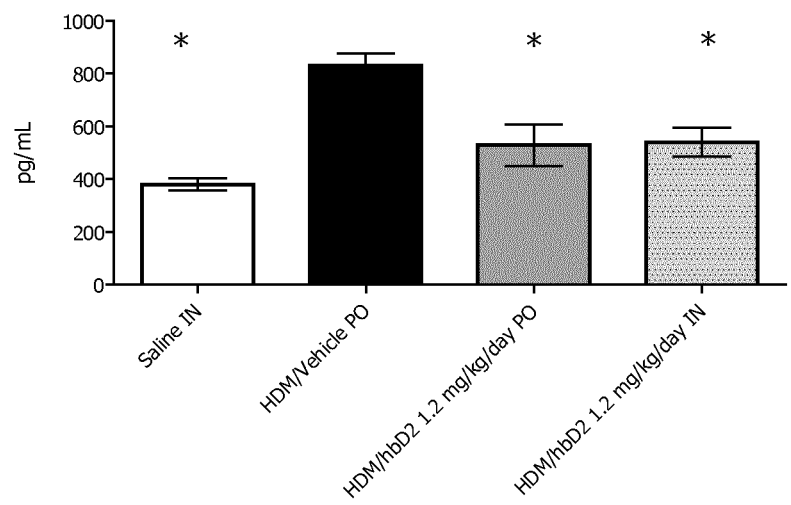

Test item hBD-2, both after oral and intranasal application TID, on day 14, effectively inhibited increase in histological inflammation of lung tissue as compared to HDM challenged vehicle treated animals (FIG. 19, 20, 21). Similar significant effects were observed on IL-4, IL-5, IL-8, IL-9 and IL-13 cytokine levels in lung tissue homogenates with both dosing routes (FIG. 12, 13, 15, 16, 18).

Conclusion: All obtained results indicate clear anti-inflammatory effects of hBD-2 in the house dust mite/Freunds complete adjuvant driven mouse model of allergic asthma. The effects were obtained using both intranasal and oral administration of hBD-2.

Example 4

Pharmacokinetic study to establish pharmacokinetic profile of hBD-2 following single oral gavage of 4 mg/kg administration to NMRI mice.

Materials and Methods

Treatment Regimen:

21 female NMRI mice were dosed by oral gavage 5 ml/kg using a gavage tube and a 1 ml syringe according to the individual body weight obtained on the day of dosing. Urine was strived sampled at random time points by gently massaging the inguinal area of the abdomen. The first blood sample was taken using a submandibular sampling method. The second blood sample was collected from Isoflurane anaesthetized mice. Intestinal samples were taken after euthanasia. The abdomen of each mouse was opened and three sections of the intestines were sampled.

Results hBD-2 could not be detected by HPLC in any of the serum or urine samples as all values were below the detection level of <10 pg/ml. This indicates that hBD-2 is not systemically available after oral dosing of 4 mg/kg in mice (FIG. 22).

Example 5

To investigate and compare the pharmacokinetic profile of hBD-2 fused to the C-terminal (molecular weight 71.336 Da) or N-terminal (molecular weight 71.666 Da) of human serum albumin following subcutaneous or intravenous administration of a molar equivalent to 1 mg/kg hBD-2 (molecular weight 66437 Da) to NMRI female mice.

Material and Methods

Treatment Regimen:

The animals were dosed 10 ml/kg of stock concentration of 1.65 mg/ml according to the individual body weight (300 µL for a 30 gram mouse). First blood sample was taken using a submandibular sampling method and the second following Isoflurane anaesthesia and euthanasia.

Results hBD-2 showed a half-life of 1 hour and the two fused proteins a half-life of 12 hours. AUC was changed dramatically. Renal clearances were also changed from 10 ml/min for hBD-2 to 0.5-2.2 ml/min for the two fused molecules (FIG. 23, 24, 25).

The example demonstrates that the half life of hBD2 can be extended markedly by C- or N-terminal conjugation to albumin.

Example 6

To determine and assess the anti-inflammatory effect of "hBD-2-albumin fusion N-terminal" in an acute 10-day Dextran Sodium Sulphate (DSS) induced colitis model in mice.

Material and Methods

Treatment Regimen:

"hBD-2-albumin N-terminal" was administered intravenously via the tail vein or subcutaneously with the use of a sterile 25G needle in a dosing volume of 10 ml/kg body weight. The animals received 1 dose daily for 10 executive days. The active control Dexamethasone (DEX) was given subcutaneously at a dose of 1 mg/kg in a dosing volume of 10 ml/kg body weight OD.

Results

Treatment with "hBD-2-albumin N-terminal" resulted in a significant inhibition of the disease activity index (DAI) when administered daily at a dose of 1.65 mg/kg via the intravenous route ($p<0.05$). Additionally, on day 10 a significant inhibition of the DAI score was also observed when the "hBD-2-albumin N-terminal" was administered daily at a dose of 1.65 mg/kg and at a dose of 125 mg/kg subcutaneously respectively ($p<0.05$).

Administration of dextran sodium sulphate resulted in a significant inflammation and injury of the colonic tissue as evidenced after histological examination. Treatment with "hBD-2-albumin N-terminal" did not result in any statistically significant reduction of this histological damage, but similarly the active control DEX failed to significantly reduce histological injury.

The results further showed a significant increase in body weight on day 7 in the animals treated with "hBD-2-albumin N-terminal" despite a transient fall in body weight on days 2 and 3. In contrast the DEX treated animals displayed a very significant decrease in body weight from day 5 onwards ($p<0.01$).

The example demonstrates the hBD2-albumin fusion N-terminal is biologically active in an animal model of an inflammatory condition.

Example 7

To determine and assess the anti-inflammatory effect of "hBD-2-albumin fusion C-terminal" in an acute 10-day Dextran Sodium Sulphate (DSS) induced colitis model in mice.

Material and Methods

Treatment Regimen:

"hBD-2-albumin C-terminal" was administered intravenously via the tail vein or subcutaneously with the use of a sterile 25G needle in a dosing volume of 10 ml/kg body weight. The animals received 1 dose daily for 10 executive days. The active control Prednisolone (Pred) was given orally by gavage at a dose of 1 mg/kg in a dosing volume of 10 ml/kg body weight OD.

Results

Treatment with "hBD-2-albumin C-terminal" resulted in a significant inhibition of the DAI when administered daily at a dose of 1.6 mg/kg via the intravenous route ($p<0.05$).

Additionally "hBD-2-albumin C-terminal" resulted in a significant inhibition of the DAI when administered on alternative days 0, 2, 4, 6, 8 and 10 at a dose of 1.6 mg/kg via the intravenous route ($p<0.05$) (FIG. 26). Daily treatment with Pred resulted in a significant inhibition of the DAI on day 9 ($p<0.05$).

Administration of dextran sodium sulphate resulted in a significant inflammation and injury of the colonic tissue as evidenced after histological examination. Treatment with "hBD-2-albumin C-terminal" at a dose of 1.6 mg/kg resulted in a statistically significant reduction of this histological damage ($p<0.05$). Similarly, daily treatment with "hBD-2-albumin C-terminal" at a dose of 1.6 mg/kg and of 16.5 mg/kg on days 0, 2, 4, 6, 8, and 10 resulted in a significant reduction of the histological damage to the colon ($p<0.01$) (FIG. 27). Treatment with the active control Pred failed to significantly reduce histological injury in the proximal part of the colon but did reduce the injury in the distal colon ($p<0.01$).

The results further showed a significant increase in body weight in the animals treated with "hBD-2-albumin C-terminal" ($p<0.05$).

The example demonstrates the hBD2-albumin fusion C-terminal is biologically active in an animal model of an inflammatory condition.

Example 8

Sequences

| SEQ ID | Name | Sequence |
|---|---|---|
| 1 | hBD1 | DHYNCVSSGGQCLYSACPIFTKIQGTCYRGKAKCCK |
| 2 | hBD2 | GIGDPVTCLKSGAICHPVFCPRRYKQIGTCGLPGTKCCKKP |
| 3 | hBD3 | GIINTLQKYYCRVRGGRCAVLSCLPKEEQIGKCSTRGRKCCRRKK |
| 4 | hBD4 | ELDRICGYGTARCRKKCRSQEYRIGRCPNTYACCLRK |
| 5 | HD5 | ATCYCRTGRCATRESLSGVCEISGRLYRLCCR |
| 6 | HD6 | AFTCHCRRSCYSTEYSYGTCTVMGINHRFCCL |
| 7 | Truncated hBD2 | PVTCLKSGAICHPVFCPRRYKQIGTCGLPGTKCCKKP |

Example 9

To determine and assess the efficacy of prophylactic treatment with IN versus Oral mammalian β-defensins in a murine house dust mite driven model of allergic asthma.

Materials and Methods

Treatment Regime:

Female 7-10 weeks old BALB/c mice were randomly allocated into 5 study groups one day prior to study start and subcutaneously (SC) sensitized to house dust mite (100 μg HDM in 200 μL saline plus Freund's complete adjuvant in 0.9% saline). The mice were treated with hBD-2 orally and intranasally respectively at a dose of 1.2 mg/kg/day (0.4 mg/kg TID) starting on day 12 in the morning and continued TID at approximately 6 hours intervals. The last dose was administered on day 14 one hour prior to challenge. The total number of doses were 8 doses or a total of 2 mg/kg hBD-2. Mice were then intranasally (IN) challenged with HDM on day 14 (HDM 25 μg in 50 μL of saline).

Tests:

Airway inflammation: At 48 hours post challenge, bronchoalveolar lavage was performed washing the lungs with 3 volumes of cold PBS (0.4; 0.3 and 0.3 mL, total 1 mL). Total and differential leucocyte cell counts were determined on an automated haematological analyser Sysmex XT-2000iV.

Lung function: Starting 48 hours after HDM challenge, measurements of lung resistance and lung compliance were carried out after methacholine challenge (3.125 MCH1; 6.25 MCH2; 12.5 MCH3 and 25 mg/mL MCH4) by anaesthetized, cannulated mice using DSI's Buxco Finepoint RC system. Data are represented as airway resistance at 10 mg/kg methacholine and as dose responsive curves.

Lung sampling for cytokine analysis: After completion of every BAL, lungs were removed from the thorax, snap frozen in liquid nitrogen and stored frozen at −80 degrees Celcius until analysis of cytokine concentration of TNF-α, IL-4, IL-5, IL-6, IL-9, IL-13 and IL-33 in lung homogenate by ELISA.

Results

An increase of lung resistance values and decrease of pulmonary compliance values in HDM-challenged vehicle treated animals in comparison to saline-challenged (non-asthmatic) mice was observed. An inflammatory response in both vehicle-treated groups of mice (oral and intranasal) was induced by a single HDM challenge 14 days post sensitization with HDM. It was characterized by a statistically significant increase in total cell, eosinophil, neutrophil, macrophage and lymphocyte counts in BALF ($p<0.05$) when compared to saline-challenged controls. Also, analysis of concentration of seven cytokines TNF-$\alpha$, IL-4, IL-5, IL-6, IL-9, IL-13 and IL-33 in lung tissue homogenates revealed significantly higher levels in HDM-challenged animals compared to saline-challenged controls.

hBD-2, both after oral and intranasal application TID, administered from day 12 to day 14 (a total of 2.0 mg/kg in 8 administrations), effectively preserved a normal lung function inhibiting the increase of airway resistance (FIG. 29) and the decrease of pulmonary compliance (FIG. 30) as compared to HDM challenged vehicle treated animals. An effect on cellular influx in BALF was observed after oral application, that significantly inhibited neutrophil counts (FIG. 31), but otherwise immune cells migrated into BALF as normally observed in asthma, but importantly the cytokine storm often observed in asthma and the basis for an asthma attack was prevented with a complete normalization of cytokine concentrations in lung tissue homogenates especially after oral administration of hBD-2. TNF-$\alpha$, IL-4, IL-5, IL-6, IL-9 and IL-13 cytokine levels following oral administration are shown in FIGS. 32-37. There was a trend towards lowering of TNF-$\alpha$, IL-4, IL-5, IL-6, IL-9 and IL-13 following intranasally administered hBD-2, but this was not statistically significantly different from the control. Conclusion: All obtained results indicate clear prophylactic, preventive and anti-inflammatory effects of hBD-2 in the house dust mite driven mouse model of allergic asthma.

Example 10

Protection and preservation of gut microbiota by prophylactic treatment with defensins.
Mice:
Mice were housed in trios, 4 cages per group. Feed intake was registered daily just before lights were turned off at 6 µm. Individual mice were subjected to experimental procedures in altered order both group and cage wise. Mice were kept at room temperature under a 12-hour light/dark cycle at SPF standard conditions. The treatment regime is described in FIG. 38.
Diets:
For dosing, the average weight was estimated to be 25 grams per mouse. Mice eat approximately 3 grams of feed per mouse per day.
Treatment Regime:
Mice were fed either a high fat diet (HFD) or a low fat (LF) control diet. The HFD contained 4 subgroups; 1 hBD2, 1 HD5, 1 hBD2/HD5 and 1 standard HFD without supplementation of defensins. Defensin concentration was 1.2 mg hBD2 per kg mouse per day. HD5 was given in equimolar concentration to hBD2. The combinatory group was given 50% hBD2+50% HD5, hence a total amount of defensins equivalent to the remaining test groups.
Tests:
Microbial analyses were carried out to study the microbiota of the intestine.
Longitudinal 16S characterization was conducted on 4 paired samples from 60 mice, 240 samples in total. Each mouse was sampled prior to diet change, 1 week post diet change, 4 weeks post diet change and at termination, thus ensuring a thorough characterization of the faecal microbiota as a result of defensin treatment.

Results
Microbiota.
hBD2 affected primarily the microbial presence, whereas HD5 and hBD2+HD5 affected primarily the microbial abundance. FIG. 40 shows the relative abundance of species in the different treatment groups and illustrate the profound effect of hBD2 and HD5 on intestinal flora. A statistically significant increase of abundance of Allobaculum was seen in the small intestine following prophylaxis with HD5 ($p<0.02$; FIG. 41). Allobaculum is a short chain fatty acid producing species. Short chain fatty acids play an important role in regulating colonic Treg cell homeostasis mediated via GPCR43. A statistically significant increase in abundance of Barnesiella in the colon was observed following prophylactic treatment with hBD2 ($p<0.03$; FIG. 43). Barnesiella is a bacteria that is able to eliminate and protect against the intestinal dominance of antibiotic-resistant pathogenic bacteria that can be observed in hospitalized patients. The abundance of Barnesiella corresponds with the amount of several immunoregulatory cells. The higher the level of Barnesiella in the colon, the more marginal zone B cells and invariant natural killer T cells enumerated in the spleen and liver. In the development of colitis in IL-10-/- mice, higher levels of a Barnesiella phylotype correlated with lower activity levels of the disease. A trend towards lower abundance of Lactobacillaceae was observed in colon following prophylactic treatment with hBD2 ($p=0.1$; FIG. 42).

Conclusion: Lung as well as intestinal microbiota seems to play an important role in asthma the latter through the gut-lung axis. Defensins' profound influence on the presence and abundance of key commensal bacteria and colonic T cell homeostasis could explain the lung effects observed in allergic asthmatic mice following oral treatment with defensins but also the difference between lung effects observed following intranasal versus oral administration. This example 10 demonstrates that both alpha and beta defensins, specifically HD5 and hBD2 have a profound influence on the microbiota composition in terms of number of species present as well as overall number of bacteria and thus seem to protect and preserve a healthy microbiota. More specifically defensins seem to promote Short Chain Fatty Acid producing bacteria, SCFA that play a key role in colonic Treg cell homeostasis.

Example 11. Treatment of Dysbiosis by Interventional Treatment with Defensins

Mice and Diets.
The experiment elucidates the effect of hBD2 and HD5 on the microbiota in diet-induced obese mice. A run-in period of 13 weeks where mice were fed a very HFD (60% energy from fat) preceded the intervention. Only mice meeting the criteria of a minimum of 12 gram weight gain (approximately 50% of initial bodyweight) during the run-in period were included in the final analyses. Mice that did not meet these criteria stayed in their respective cages as hierarchy 'keepers'. They were exposed to all experimental tests, but excluded from the analyses.
Treatment Regimen.
Before the intervention all mice were MR scanned. Cages of mice were allocated to experimental groups based on their fat mass. All subsequent measures were paired with data from the same mouse before the intervention. A LFD (low fat diet) reference group was running in parallel. As controls for the intervention 2 additional groups were included: 1 very HFD and 1 LFD. Experimental mice stayed on the very HFD during the intervention. The mice were on the experimental diet for 10 weeks. They were co-housed throughout the experiment, 4 mice per cage, 3 cages per group. All tests ran over 3 days, 1 cage per group per day. The treatment regime is shown in FIG. 39.

Tests.

Microbial analyses were carried out to study the microbiota of the intestine. Longitudinal 16S characterization was conducted on 4 paired samples from 60 mice, 240 samples in total. Each mouse was sampled prior to diet change, 1 week post diet change, 4 weeks post diet change and at termination, thus ensuring a thorough characterization of the faecal microbiota as a result of defensin treatment.

Results

Microbiota.

Both defensins were shown to have a profound influence on the bacterial presence as well as bacterial absence. HD5 increased the abundance of Alloprevotella statistically significantly in the colon (p<0.02) (FIG. 44) whereas hBD2 had no influence on Alloprevotella abundance. hBD2 dramatically and statistically significant increased the relative abundance of Bifidobacteriaceae both in the small intestine and in the colon (p<0.0001 and p<0.04 respectively; FIG. 45). There was a trend towards HD5 increasing the abundance of Bifidobacteriaceae in the small intestine (FIG. 45). Lung as well as intestinal microbiota seems to play an important role in asthma the latter through the gut-lung axis. Defensins profound influence on the presence and abundance of key commensal bacteria and colonic T cell homeostasis could explain the lung effects observed in allergic asthmatic mice following oral treatment with defensins but also the difference between lung effects observed following intranasal versus oral administration.

Conclusion: This example 11 demonstrates that both alpha and beta defensins, specifically hBD2 and HD5, have a profound influence on the microbiota composition in terms of number of species present as well as overall number of bacteria and thus seem to protect and preserve a healthy microbiota. More specifically defensins seem to promote Short Chain Fatty Acid producing bacteria, SCFA that play a key role in colonic Treg cell homeostasis.

REFERENCES

Bouloukaki, I. et al., 2011. Sputum and nasal lavage lung-specific biomarkers before and after smoking cessation. BMC Pulmonary Medicine 11: 35
Charlson, E. S. et al. 2011. Topographical continuity of bacterial populations in the healthy human respiratory tract. Am J Respir Crit Care Med 184: 957-963.
Cosmi, L et al., 2011. TH17 cells: new players in asthma pathogenesis. Allergy 66: 989-998.
Donia, M. S. and Fischbach, M. A. 2015. Small molecules from the human microbiota. Science 349, 1254766
Dorrestein, P. C. et al., 2014. Finding the missing links among metabolites, microbes, and the host. Immunity 40: 824-832.
Ege, M. J. et al., 2011. Exposure to environmental microorganisms and childhood asthma. NEJM 364: 701-709.
Essilfie, A. et al., 2015. Macrolide therapy suppresses key features of experimental steroid-sensitive and steroid-insensitive asthma. Thorax 70: 458-467.
Fletcher, C. and Peto, R. 1977. The natural history of chronic airflow obstruction. BMJ: 1: 1645-1648.
Hansbro, P. M. et al, 2004. Role of atypical bacterial infection on the lung in predisposition/protection of asthma. Pharmacol Ther 101: 193-210
Hansbro, P. M. et al., 2011. Cytokine/anti-cytokine therapy—novel treatments for asthma? BJP 163: 81-95.
Hilty, M. et al., 2010. Disordered microbial communities in asthmatic airways. PLoS ONES, e8578
Hogg, J. C. et al. 2004. The nature of small-airway obstruction in chronic obstructive pulmonary disease. NEJM: 350: 2645-2653.
Jakobsson, H. E. et al. 2014. Decreased gut microbiota diversity, delayed Bacteroidetes colonization and reduced Th1 responses in infants delivered by Caesarian section. Gut 63: 559-566.
Marra, F. et al., 2009. Antibiotic use in children is associated with increased risk of asthma. Pediatrics 123: 1003-1010.
Marsland, B. J. et al., 2015. The gut-lung axis in respiratory disease. Annals ATS 12: S150-156
Penders, J. et al., 2007. The role of the intestinal microbiota in the development of atopic disorders. Allergy 2007: 1223-1236
Salzman N H, Underwood M A and Bevins C L, 2007. Paneth cells, defensins, and the commensal microbiota: a hypothesis on intimate interplay at the intestinal mucosa. Semin Immunol 19(2):70-83.
Schirmer, M. et al., 2016. Linking the human gut microbiome to inflammatory cytokine production capacity. Cell 167: 1125-1136
Trompette, A. et al., 2013. Gut microbiota metabolism of dietary fiber influences allergic airway disease and hematopoiesis. Nature Medicine 20: 159-168.
Wehkamp J, et al., 2002. Innate immunity and colonic inflammation: enhanced expression of epithelial alpha-defensins. Dig Dis Sci. 47(6):1349-55.
Wills-Karp, M. et al., 2001. The germless theory of allergic disease: revisiting the hygiene Hypothesis. Nat Rev Immunol (1): 69-75.
WO 2010/007166
WO 92/06204
WO 95/17413
WO 95/22625
U.S. Pat. No. 5,223,409
WO 2013/007596

The invention claimed is:

1. A method for prevention of inflammatory diseases of the respiratory system selected from asthma, bronchiectasis, chronic obstructive pulmonary disorder (COPD) or emphysema, the method comprising oral administration of human beta-defensin 2 (hBD2) (SEQ ID NO: 2) or N-terminally truncated hBD2 by 1-4 amino acids to a subject in need thereof.

2. The method of claim 1, wherein said asthma is mild intermittent asthma, mild persistent asthma, moderate persistent asthma, severe persistent asthma, eosinophilic asthma, neutrophilic asthma, steroid refractory asthma or status asthmaticus.

3. The method according to claim 1, wherein the administration is oral.

4. The method according to claim 1, wherein hBD2 and HD5 are administered.

5. The method according to claim 1, further comprising increasing gene richness, increasing the number of phylae, increasing butyrate production and/or tryptophan production, or decreasing acetate production of or from lung microbiota.

6. The method according to claim 1, wherein the subject has
   a. asthmatic symptoms more than 2 times per week;
   b. asthmatic attacks at varying intensity;
   c. asthmatic symptoms at night more than 2 times per month;
   d. a forced expiratory volume at 1 second (FEV1) less than 80; or
   e. a peak expiratory flow rate (PEFR) with a variability of more than 20%.

7. The method according to claim 1, wherein the defensin is administered in combination with one or more glucocorticoids, β-agonists, leukotriene receptor antagonists, theophylline, antibiotics, rifaximin, immunosuppressants, chemo- or immune therapy, prebiotics, probiotics, tryptophane, fatty acids, HNP-1, HNP-2, HNP-3, HNP-4, cathelicidin, lactoferrin, lactoferricin, lysozyme, fecal transplants or any combination thereof.

8. The method according to claim 1, wherein said defensin is administered at a dosage of 0.1 mg to 10 mg defensin/kg per day.

9. The method according to claim 1, wherein said defensin is administered every other day.

10. The method according to claim 1, wherein said defensin is administered daily.

11. The method according to claim 1, wherein the subject is a dog, cat, horse, pig, cow, sheep, goat or poultry.

12. A method for preventing allergic inflammation in the lung of a subject, comprising oral administration of hBD2 (SEQ ID NO: 2) or N-terminally truncated hBD2 by 1-4 amino acids to a subject in need thereof, wherein said administration prevents an allergic inflammation in the lung, and wherein said administration reduces airway hyperresponsiveness or increases pulmonary compliance in said subject.

13. A method for preventing allergic inflammation in the lung of a subject, comprising oral administration of hBD2 (SEQ ID NO: 2) or N-terminally truncated hBD2 by 1-4 amino acids to a subject in need thereof, wherein said administration prevents an allergic inflammation in the lung, and wherein said administration reduces white blood cell count in bronchio-alveolar-lavage-fluid (BALF) in said subject.

14. A method for preventing allergic inflammation in the lung of a subject, comprising oral administration of hBD2 (SEQ ID NO: 2) or N-terminally truncated hBD2 by 1-4 amino acids to a subject in need thereof, wherein said administration prevents an allergic inflammation in the lung, and wherein said administration prevents or reduces cytokine storm in said individual.

* * * * *

SEQUENCE LISTING

```
<160> NUMBER OF SEQ ID NOS: 7

<210> SEQ ID NO 1
<211> LENGTH: 36
<212> TYPE: PRT
<213> ORGANISM: Homo sapiens

<400> SEQUENCE: 1

Asp His Tyr Asn Cys Val Ser Ser Gly Gly Gln Cys Leu Tyr Ser Ala
1               5                   10                  15
```

Cys Pro Ile Phe Thr Lys Ile Gln Gly Thr Cys Tyr Arg Gly Lys Ala
                    20                  25                  30

Lys Cys Cys Lys
        35

<210> SEQ ID NO 2
<211> LENGTH: 41
<212> TYPE: PRT
<213> ORGANISM: Homo sapiens

<400> SEQUENCE: 2

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
                20                  25                  30

Pro Gly Thr Lys Cys Cys Lys Lys Pro
            35                  40

<210> SEQ ID NO 3
<211> LENGTH: 45
<212> TYPE: PRT
<213> ORGANISM: Homo sapiens

<400> SEQUENCE: 3

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
                20                  25                  30

Cys Ser Thr Arg Gly Arg Lys Cys Cys Arg Arg Lys Lys
            35                  40                  45

<210> SEQ ID NO 4
<211> LENGTH: 37
<212> TYPE: PRT
<213> ORGANISM: Homo sapiens

<400> SEQUENCE: 4

Glu Leu Asp Arg Ile Cys Gly Tyr Gly Thr Ala Arg Cys Arg Lys Lys
1               5                   10                  15

Cys Arg Ser Gln Glu Tyr Arg Ile Gly Arg Cys Pro Asn Thr Tyr Ala
                20                  25                  30

Cys Cys Leu Arg Lys
            35

<210> SEQ ID NO 5
<211> LENGTH: 32
<212> TYPE: PRT
<213> ORGANISM: Homo sapiens

<400> SEQUENCE: 5

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu Cys Cys Arg
                20                  25                  30

<210> SEQ ID NO 6
<211> LENGTH: 32
<212> TYPE: PRT
<213> ORGANISM: Homo sapiens

<400> SEQUENCE: 6

```
Ala Phe Thr Cys His Cys Arg Arg Ser Cys Tyr Ser Thr Glu Tyr Ser
1               5                   10                  15

Tyr Gly Thr Cys Thr Val Met Gly Ile Asn His Arg Phe Cys Cys Leu
                20                  25                  30

<210> SEQ ID NO 7
<211> LENGTH: 37
<212> TYPE: PRT
<213> ORGANISM: Homo sapiens

<400> SEQUENCE: 7

Pro Val Thr Cys Leu Lys Ser Gly Ala Ile Cys His Pro Val Phe Cys
1               5                   10                  15

Pro Arg Arg Tyr Lys Gln Ile Gly Thr Cys Gly Leu Pro Gly Thr Lys
                20                  25                  30

Cys Cys Lys Lys Pro
            35
```